(12) United States Patent
Myers

(10) Patent No.: US 8,617,241 B2
(45) Date of Patent: Dec. 31, 2013

(54) DOUBLE BUNDLE ACL REPAIR

(75) Inventor: Thomas H. Myers, Marietta, GA (US)

(73) Assignees: IMDS Corporation, Providence, UT (US); Thomas H. Myers, Marietta, GA (US)

(*) Notice: Subject to any disclaimer, the term of this patent is extended or adjusted under 35 U.S.C. 154(b) by 150 days.

(21) Appl. No.: 12/751,072

(22) Filed: Mar. 31, 2010

(65) Prior Publication Data

US 2010/0249930 A1   Sep. 30, 2010

Related U.S. Application Data

(60) Provisional application No. 61/164,980, filed on Mar. 31, 2009.

(51) Int. Cl.
*A61F 2/08* (2006.01)

(52) U.S. Cl.
USPC ............................................. 623/13.14

(58) Field of Classification Search
USPC ............. 623/13.11–13.2, 16.11; 606/99, 228, 606/232, 233, 321, 323
See application file for complete search history.

(56) References Cited

U.S. PATENT DOCUMENTS

| | | | | |
|---|---|---|---|---|
| 3,176,316 A | * | 4/1965 | Bodell | 623/13.19 |
| 4,411,027 A | * | 10/1983 | Alexander et al. | 623/13.18 |
| 4,662,886 A | * | 5/1987 | Moorse et al. | 623/13.15 |
| 4,772,286 A | | 9/1988 | Goble et al. | |
| 4,773,910 A | * | 9/1988 | Chen et al. | 623/13.2 |
| 4,792,336 A | * | 12/1988 | Hlavacek et al. | 623/13.18 |
| 4,932,972 A | * | 6/1990 | Dunn et al. | 623/13.19 |
| 5,004,474 A | * | 4/1991 | Fronk et al. | 623/13.14 |
| 5,112,335 A | | 5/1992 | Cazenave | |
| 5,234,430 A | * | 8/1993 | Huebner | 606/60 |
| 5,306,301 A | | 4/1994 | Graf | |
| RE34,871 E | * | 3/1995 | McGuire et al. | 606/99 |
| 5,423,819 A | * | 6/1995 | Small et al. | 606/232 |
| 5,425,766 A | * | 6/1995 | Bowald | 623/13.18 |
| 5,505,735 A | * | 4/1996 | Li | 623/13.14 |
| 5,562,669 A | * | 10/1996 | McGuire | 623/13.12 |
| 5,575,819 A | * | 11/1996 | Amis | 623/13.13 |
| 5,645,588 A | | 7/1997 | Graf | |

(Continued)

FOREIGN PATENT DOCUMENTS

| CA | 2181179 | 7/1995 |
|---|---|---|
| WO | WO9519141 | 7/1995 |

OTHER PUBLICATIONS

Basdekis George, Christel Pascal, Anne Francois. Validation of the Position of the Femoral Tunnels in Anatomic Double-Bundle ACL Reconstruction with 3-D CT Scan. Knee Surg Sports Traumatol Arthrosc (2009) 17:1089-1094.

(Continued)

*Primary Examiner* — Alvin Stewart
(74) *Attorney, Agent, or Firm* — G. Jo Hays; James Larson; James M. Pinkston

(57) ABSTRACT

A system for single tunnel, double bundle anterior cruciate ligament reconstruction includes implant constructs and instruments. The implant constructs provide a combination of cortical fixation and bone tunnel aperture fixation. The implant constructs separate a graft into distinct bundles. The instruments are used to prepare shaped bone tunnels to receive the implant constructs and graft bundles. Methods for reconstructing the antero-medial and postero-lateral bundles of the anterior cruciate ligament may rely on single femoral and tibial tunnels and a single strand of graft.

14 Claims, 40 Drawing Sheets

(56) References Cited

U.S. PATENT DOCUMENTS

| | | | |
|---|---|---|---|
| 5,681,320 A | 10/1997 | McGuire | |
| 5,709,683 A * | 1/1998 | Bagby | 623/16.11 |
| 5,899,938 A * | 5/1999 | Sklar et al. | 623/13.14 |
| 5,961,520 A * | 10/1999 | Beck et al. | 606/232 |
| 5,984,966 A * | 11/1999 | Kiema et al. | 623/13.14 |
| 6,001,100 A * | 12/1999 | Sherman et al. | 606/232 |
| 6,001,106 A * | 12/1999 | Ryan et al. | 606/102 |
| 6,022,356 A | 2/2000 | Noyes et al. | |
| 6,056,752 A * | 5/2000 | Roger | 623/13.12 |
| 6,099,530 A * | 8/2000 | Simonian et al. | 606/75 |
| 6,099,568 A * | 8/2000 | Simonian et al. | 623/13.11 |
| 6,110,207 A * | 8/2000 | Eichhorn et al. | 623/13.14 |
| 6,129,762 A * | 10/2000 | Li | 623/13.11 |
| 6,193,754 B1 * | 2/2001 | Seedhom | 623/13.11 |
| 6,221,107 B1 * | 4/2001 | Steiner et al. | 623/13.14 |
| 6,235,057 B1 * | 5/2001 | Roger et al. | 623/13.12 |
| 6,264,694 B1 * | 7/2001 | Weiler | 623/13.14 |
| 6,283,996 B1 * | 9/2001 | Chervitz et al. | 623/13.14 |
| 6,355,066 B1 * | 3/2002 | Kim | 623/13.14 |
| 6,379,361 B1 * | 4/2002 | Beck et al. | 606/323 |
| 6,440,134 B1 * | 8/2002 | Zaccherotti et al. | 606/62 |
| 6,497,726 B1 * | 12/2002 | Carter et al. | 623/13.17 |
| 6,517,578 B2 * | 2/2003 | Hein | 623/13.13 |
| 6,517,579 B1 | 2/2003 | Paulos et al. | |
| 6,533,802 B2 * | 3/2003 | Bojarski et al. | 606/232 |
| 6,554,862 B2 * | 4/2003 | Hays et al. | 623/13.14 |
| 6,579,295 B1 * | 6/2003 | Supinski | 623/13.14 |
| 6,632,245 B2 | 10/2003 | Kim | |
| 6,652,560 B1 * | 11/2003 | Gerke et al. | 606/232 |
| 6,716,234 B2 | 4/2004 | Grafton | |
| 6,723,099 B1 * | 4/2004 | Goshert | 606/329 |
| 6,780,187 B2 * | 8/2004 | Supinski | 623/13.14 |
| 6,887,271 B2 * | 5/2005 | Justin et al. | 623/13.14 |
| 6,893,462 B2 * | 5/2005 | Buskirk et al. | 623/13.17 |
| 6,902,578 B1 * | 6/2005 | Anderson et al. | 623/16.11 |
| 6,923,810 B1 * | 8/2005 | Michelson | 606/247 |
| 6,932,841 B2 * | 8/2005 | Sklar et al. | 623/13.14 |
| 7,001,390 B2 * | 2/2006 | Gebhardt et al. | 606/151 |
| 7,008,451 B2 * | 3/2006 | Justin et al. | 623/13.14 |
| 7,025,786 B2 * | 4/2006 | Goble et al. | 623/13.14 |
| 7,137,996 B2 * | 11/2006 | Steiner et al. | 623/13.14 |
| 7,141,066 B2 * | 11/2006 | Steiner et al. | 623/13.12 |
| 7,201,773 B2 * | 4/2007 | Steiner et al. | 623/13.14 |
| 7,235,074 B1 * | 6/2007 | Sklar | 606/53 |
| 7,309,356 B2 * | 12/2007 | Steiner | 623/13.14 |
| 7,326,247 B2 | 2/2008 | Morgan | |
| 7,329,281 B2 * | 2/2008 | Hays et al. | 623/13.14 |
| 7,335,230 B2 * | 2/2008 | Goulet et al. | 623/13.17 |
| 7,338,531 B2 * | 3/2008 | Ellis et al. | 623/23.74 |
| 7,347,872 B2 * | 3/2008 | Goulet et al. | 623/13.17 |
| 7,468,074 B2 * | 12/2008 | Caborn et al. | 623/13.14 |
| 7,500,983 B1 | 3/2009 | Kaiser et al. | |
| 7,530,990 B2 * | 5/2009 | Perriello et al. | 606/232 |
| 7,695,503 B1 | 4/2010 | Kaiser et al. | |
| 7,727,278 B2 * | 6/2010 | Olsen et al. | 623/13.12 |
| 7,763,071 B2 * | 7/2010 | Bianchi et al. | 623/13.12 |
| 7,776,077 B2 | 8/2010 | Kaiser et al. | |
| 7,819,898 B2 | 10/2010 | Stone et al. | |
| 7,942,914 B2 * | 5/2011 | Cerundolo | 606/321 |
| 7,963,983 B2 * | 6/2011 | Cerundolo | 606/321 |
| 7,967,843 B2 | 6/2011 | Kaiser | |
| 7,967,861 B2 * | 6/2011 | Montgomery et al. | 623/13.15 |
| RE42,526 E * | 7/2011 | Reiser et al. | 623/13.14 |
| 8,007,533 B2 * | 8/2011 | Zhukauskas et al. | 623/13.14 |
| 8,048,158 B2 * | 11/2011 | Hays et al. | 623/13.14 |
| 8,192,490 B2 * | 6/2012 | Baird et al. | 623/13.14 |
| 8,226,716 B2 * | 7/2012 | Mckernan et al. | 623/13.17 |
| 8,435,294 B2 | 5/2013 | Montgomery | |
| 2003/0216780 A1 | 11/2003 | Fitts et al. | |
| 2004/0153153 A1 | 8/2004 | Elson | |
| 2004/0243132 A1 | 12/2004 | Whittaker et al. | |
| 2005/0159812 A1 * | 7/2005 | Dinger et al. | 623/13.14 |
| 2006/0052787 A1 * | 3/2006 | Re et al. | 606/72 |
| 2006/0247642 A1 * | 11/2006 | Stone et al. | 606/73 |
| 2006/0247790 A1 * | 11/2006 | McKay | 623/23.44 |
| 2007/0156151 A1 | 7/2007 | Guan et al. | |
| 2007/0218424 A1 | 9/2007 | Vuorisalo | |
| 2007/0225805 A1 * | 9/2007 | Schmieding | 623/13.14 |
| 2007/0250166 A1 * | 10/2007 | McKay | 623/17.11 |
| 2008/0119929 A1 | 5/2008 | Schmieding | |
| 2008/0234819 A1 | 9/2008 | Schmieding | |
| 2009/0036927 A1 * | 2/2009 | Vestgaarden | 606/247 |
| 2009/0131986 A1 * | 5/2009 | Lee et al. | 606/247 |
| 2009/0157119 A1 * | 6/2009 | Hale | 606/247 |
| 2010/0049258 A1 | 2/2010 | Dougherty | |
| 2010/0049319 A1 | 2/2010 | Dougherty | |
| 2010/0249930 A1 * | 9/2010 | Myers | 623/13.14 |
| 2011/0009885 A1 | 1/2011 | Graf et al. | |
| 2011/0137416 A1 | 6/2011 | Myers | |
| 2012/0059469 A1 * | 3/2012 | Myers et al. | 623/13.14 |

OTHER PUBLICATIONS

Cha Peter, Brucker Peter, West Robin, Zelle Boris, Yagi Masayoshi, Kurosaka Masahiro, Fu Freddie. Arthroscopic Double-Bundle Anterior Cruciate Ligament Reconstruction: An Anatomic Approach, Techinical Notes: Arthroscopy vol. 21, No. 10, Oct. 2005: pp. 1275-1277.

Duthon VB, Barea C, Abrassart S, Fasel JH, Fritschy D, Menetrey J. Anatomy of the anterior cruciate ligament. Knee Surgery Sports Traumatoloty Arthroscopy 2006;14(3):204-213.

Fu FH, Lo MY, Lo MS, Pombo MW, Singleton R. Anatomic double-bundle ACL reconstruction: patient information handout / frequently asked questions. Department of Orthopedic Surgery, University of Pittsburgh. Not formally published. No date.

Freddie H. Fu, C. Benjamin. Anterior Cruciate Ligament Reconstruction Using Quadruple Hamstring. Operative Techniques in Orthopaedics, vol. 9 No. 4 (Oct. 1999): pp. 264-272.

Hara K, Mochizuki T, Sekiya I, Yamaguchi K, Akita K, Muneta T. Anatomy of normal human anterior cruciate ligament attachments evaluated by divided small bundles. The American Journal of Sports Medicine 2009;37(12):2386-2391.

Marshall JL, Warren RF, Wickiewicz TL, Reider B. The Anterior Cruciate Ligament: A Technique of Repair and Reconstruction, Clinical Orthopaedics and Related Research No. 143 Sep. 1979 pp. 97-106.

Masaaki Takahashi, Mitsuhito Doi, Masashi Abe, Daisuke Suzuki, Akira Nagano. Anatomical Study of the Femoral and Tibial Insertions of the Anteromedial and Posterolateral Bundles of Human Anterior Cruciate Ligament. Am J Sports Med 2006 34: 787.

Mitsuhito Doi, Masaaki Takahashi, Masashi Abe, Daisuke Suzuki, Akira Nagano. Lateral Radiographic Study of the Tibial Sagital Insertions of the Anteromedial and Posterolateral Bundles of Human Anterior Cruciate Ligament. Knee Surg Sports Traumatol (2009) 17: 347-351.

Mochizuki T, Muneta T, Nagase T, Shirasawa SI, Akita KI, Sekiya I. Cadaveric knee observation study for describing anatomic femoral tunnel placement for two-bundle anterior cruciate ligament reconstruction. Arthroscopy 2006;22(4):356-361.

Craig D. Morgan, Divid Caborn. Anatomic Graft Fixation Using a Retrograde Biointerference Screw for Endoscopic Anterior Cruciate Ligament. Reconstruction: Single-Bundle and 2-Bundle Techniques. Techniques in Orthopaedis 20(3): 297-302 2005.

Petersen W, Zantop T. Anatomy of the anterior cruciate ligament with regard to its two bundles. Clinical Orthopedics and Related Research 2007;454:35-47.

Ranawat A, Fu FH. Double bundle ACL reconstruction restores anatomy, kinematics. Orthopedics Today 2007;27:94.

Joel T. Rohrbough, Russell F. Warren, Thomas Wickiewicz. Posterior Cruciate Ligament Reconstruction: Single Versus Double-Bundle Technique. Techiniques in Orthopaedics 16(2): 119-126 2001.

Tallay Andras, Lim Mui-Hong, Bartlett John. Anatomical Study of the Human Anterior Cruciate Ligament Stum's Tiial Insertion Footprint. Knee Surg Sports Traumatol Arthrosc (2008) 16:741-746.

Tan JI, Chang PCC, Mitra AK, Tay BK. Anthropometry of Anterior Cruciate Ligament in Singaporean Chinese. Ann Acad Med Singapore 1998; 27:776-9.

Wang JQ, Ao YF, Yu CL, Liu P, Xu Y, Chen LX. Clinical evaluation of double-bundle anterior cruciate ligament reconstruction procedure

(56) References Cited

OTHER PUBLICATIONS using hamstring tendon grafts: a prospective, randomized and controlled study. Chinese Medical Journal 2009;122(6):706-711.

Zaffagnini Stefano, Bruni Danilo, Martelli Sandra, Imakiire Naoaki, Marcacci Maurilio, Russo Alessandro. Double-bundle ACL reconstruction: Influence of Femoral Tunnel Orientationin Knee Laxity Analysed with a Navigation System—an in-vitro Biomechanical Study. *BMC Musculoskeletal Disorders* 2008, 9:25doi:10.1186/1471-2474-9-25 http://www.biomedcentral.com/1471-2474/9/25.

Lenschow, S., et al. *Structural Properties of a New Device for Graft Fixation in Cruciate Ligament Reconstruction: The Shim Technique.* Arthroscopy Orthopedic Trauma Surg. (2011) 131:1067-1072.

Lenschow, S., et al. *Structural Properties of a New Fixation Strategy in Double Bundle ACL Reconstruction: The MiniShim.* Arthroscopy Orthopedic Trauma Surg. (2011) 131:1159-1165.

Ramon A. Ruberte Thiele, M.S., Robert Brick Campbell, M.D., Annunziato Amendola, M.D., Jon K. Sekiya, M.D. Biochemical Comparison of Figure-of-8 Versus Cylindrical Tibial Inlay Constructs for Arthroscopic Posterior Cruciate Ligament Reconstruction. Arthroscopy: The Journal of Arthroscopic and Related Surgery, vol. 26, No. 7 (Jul. 2010): pp. 977-983.

\* cited by examiner

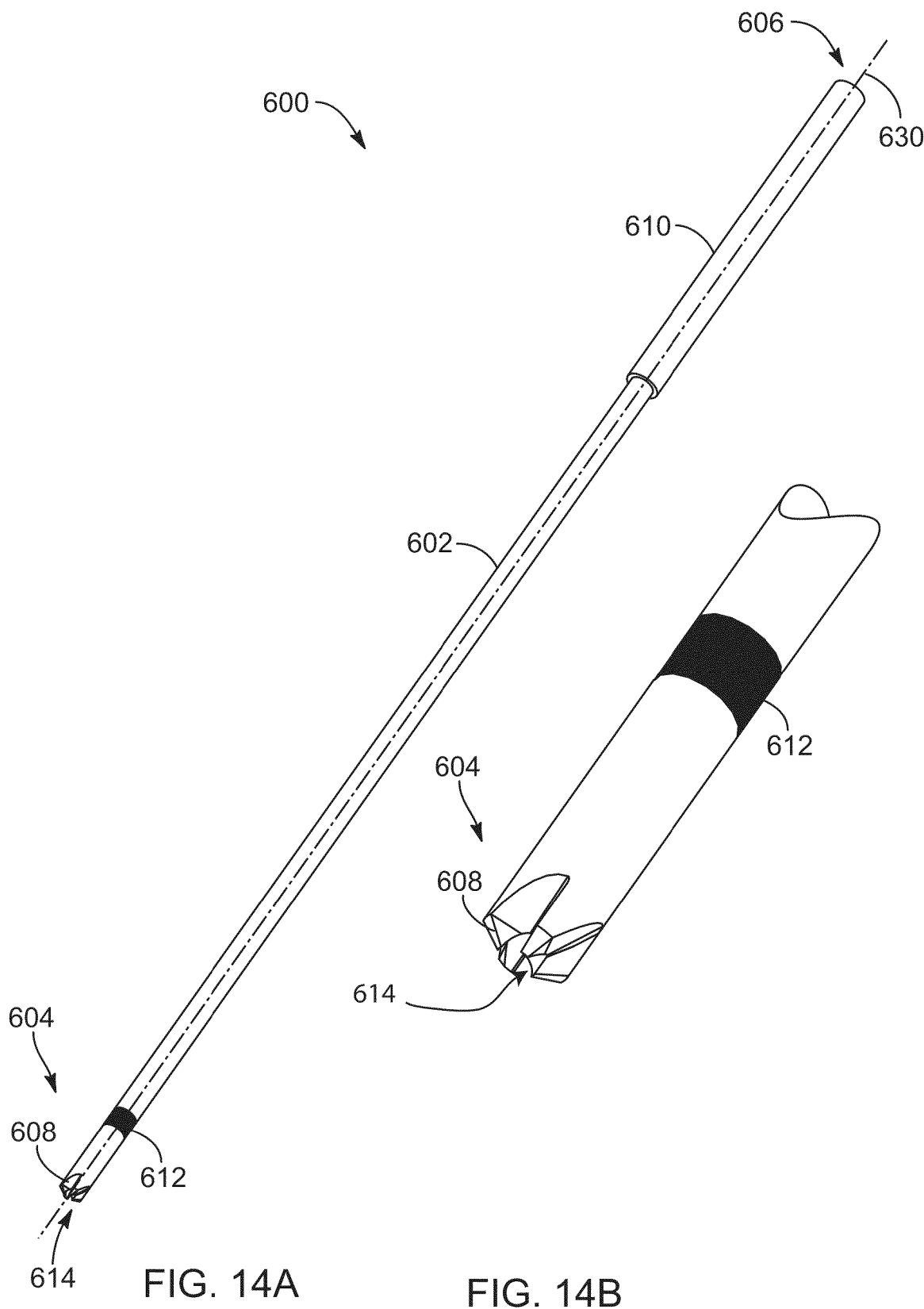

DOUBLE BUNDLE ACL REPAIR

CROSS-REFERENCE TO RELATED APPLICATIONS

This application claims the benefit of U.S. Application No. 61/164,980, filed Mar. 31, 2009, entitled DOUBLE BUNDLE ACL REPAIR.

The above-referenced document is hereby incorporated by reference in its entirety.

BACKGROUND OF THE INVENTION

The Field of the Invention

The invention relates to anterior cruciate ligament (ACL) repair surgery. More precisely, the present invention relates to implants and instruments for double bundle ACL repair, and methods of use.

It is generally accepted in the field of orthopedic surgery that the anterior cruciate ligament does not heal itself after injury. Initial attempts at repair of this ligament resulted in nearly uniform failure of the ligament to stabilize the knee joint.

Over the course of the last four decades, practitioners have turned to methods of ligament reconstruction in attempts to restore knee stability and normal knee kinematics. Most surgeons have become proficient with a ligament reconstruction technique involving autograft or allograft replacement of the native ACL. Autografts, which are harvested from the patient's own body, may comprise bone-patellar tendon-bone (BPTB), hamstring tendon (HT), or occasionally quadriceps tendon (QT). Allografts, which are harvested from a donor, may comprise patellar tendon, quadriceps tendon, Achilles tendon, tibialis anterior tendon, hamstring tendons, or occasionally peroneal tendons. Any of these grafts may be placed so that it traverses the intercondylar notch and its ends rest within tibial and femoral bone tunnels.

Two important surgical factors in achieving a stable, fully functional, pain-free knee after ACL reconstruction are correct placement of the femoral and tibial tunnels, so that the ACL graft does not impinge the posterior cruciate ligament (PCL) or the roof of the intercondylar notch, and the use of slip-resistant, stiff, strong fixation for the ends of the graft.

Tibial and femoral bone tunnel placement has been a very controversial topic. Anterior placement of the femoral tunnel has become generally accepted as a technical cause of graft failure. Recently, after years of transtibial placement of the femoral bone tunnel, it has become increasingly popular to drill the femoral tunnel separately (i.e., through a medial arthroscopic portal). This may result in more anatomic placement of the femoral tunnel and improved graft orientation.

There are currently many options for graft fixation. Many surgeons who prefer BPTB grafts use interference screw fixation. However, among surgeons who prefer soft tissue grafts, a wide variety of fixation devices are used with little consensus as to what is best. Soft tissue graft fixation can be broadly divided into interference screw-based fixation, cortical fixation, and cross pin fixation.

Interference screw-based fixation of soft tissue grafts may be used in the femur and tibia. This type of fixation generates friction between the graft and the bone tunnel. Many surgeons who were originally trained in BPTB grafts continue to use this method of fixation when they use soft tissue grafts. Metal and bioabsorbable interference screws are currently available. However, there are no interference screws that have demonstrated bony ingrowth, which would be beneficial over the long term.

Cortical fixation may be preferred by surgeons who primarily use soft tissue grafts. A number of devices are known to take advantage of the innate strength of cortical bone. As early as 1966, German surgeon Helmut Brückner described an ACL reconstruction technique in which a BPTB graft was secured by sutures to a button resting on the lateral aspect of the lateral femoral condyle. Other examples of cortical fixation devices include Endobutton™ (Smith and Nephew) and EZLoc™ (Biomet). Cortical fixation devices have been shown to have some of the highest pullout strengths of any soft tissue graft fixation device. In the femur, these devices may comprise an extracortical anchor attached to a fabric or suture loop. Such a device may be used by draping the graft over the fabric loop, supporting the anchor against the exterior cortical surface so that the graft is suspended within the tunnel, and securing the fabric loop to the anchor. In the tibia, cortical fixation may be achieved by stitching sutures to the free ends of the graft, placing a screw through the anterior tibial cortex, tying the sutures around the screw, and compressing the sutures against the cortex with a washer.

Cross-pin fixation has been gaining in popularity, at least in part because of the perception that it may provide secure fixation closer to the tunnel aperture than that provided by cortical fixation. Cross-pin fixation may be achieved by passing a pin across a bone tunnel close to the aperture and draping the graft over the pin where it crosses the tunnel.

Although there may be little evidence that aperture fixation provides greater stability than does cortical fixation, many surgeons prefer aperture fixation because it may avoid the so-called "bungee effect" of cortical fixation devices. This theory presumes that an ACL reconstruction spanning a longer distance between fixation points will have greater elasticity than an ACL reconstruction spanning a shorter distance. Fixation closer to the joint space may provide higher stability than remote fixation at the cortex because the distance across the joint space is much less than the distance between extracortical fixation points. However, a 2005 meta-analysis of stability after ACL reconstruction showed cortical fixation to be associated with the highest rates of ACL reconstruction stability for soft tissue grafts.

There may be biomechanical evidence that aperture fixation may lead to increased graft stiffness. On the tibia, distal cortical fixation of a soft tissue ACL graft may be stronger, stiffer, and more slip resistant than is aperture fixation with an interference screw alone. The use of an interference screw alone may cause tunnel widening and may prevent circumferential tendon-tunnel healing, which may result in inferior strength and stiffness at 4 weeks compared with cortical fixation. However, the insertion of a bone dowel alongside a tendon graft in the tunnel, in conjunction with distal cortical fixation, may prevent tunnel widening, increase stiffness, promote circumferential healing, and simplify revision surgery.

Aggressive, brace-free rehabilitation with early weight bearing may be safe following high-stiffness, slip-resistant fixation. The high stiffness provided by distal cortical fixation may reduce the graft tension required to restore stability and may lower graft tension during open-chain exercise. Reducing the graft tension without increasing anterior laxity requires high-stiffness fixation which also resists slipping and tension loss during aggressive rehabilitation. Whipstitch-post tibial cortical fixation was the first fixation method used successfully for quadrupled hamstring grafts. Simple interference screw fixation has had mixed results, while interference screw fixation combined with cortical fixation has shown very good results. Similarly, interference screw-based methods such as the Intrafix™ (DePuy Mitek) appear to be promising constructs on the tibial side. Although cross-pin fixation on the tibial side may be popular among surgeons, there is a paucity of clinical data pertaining to it, and the clinical series that have been published to date have shown mixed results.

Despite advancements in single bundle ACL reconstruction, a review of the literature demonstrates that between 10% and 30% of patients report persistent instability following single bundle ACL reconstruction surgery. Among single bundle ACL reconstructions, only 70% of KT1000 test results demonstrate a <2 mm side-to-side difference, with a failure rate of 5% to 10%. The return-to-sport rate for single bundle restorations is only 60% to 70%.

Anatomic studies reveal that the ACL has two functional bundles: the anteromedial (AM) bundle and the posterolateral (PL) bundle. The bundles are named according to their tibial insertion sites. With the knee in extension, the AM and PL bundles are parallel to each other and are oriented generally along the mechanical axis of the leg. When the knee is flexed to 90 degrees, the AM and PL bundles are crossed. This occurs because the PL bundle femoral insertion site is posterior to the AM bundle femoral insertion site when the knee is in extension, and anterior to the AM bundle femoral insertion site when the knee is flexed to 90 degrees. In other words, the AM bundle femoral insertion site rotates over the PL bundle femoral insertion site as the knee flexes. As a result, each bundle makes a unique contribution to knee kinematics at different knee flexion angles. In extension, the PL bundle tightens and the AM bundle relaxes, whereas in flexion, the AM bundle tightens as the PL bundle becomes lax. The AM bundle is the primary restraint against anterior tibial translation and the PL bundle tends to stabilize the knee in full extension, particularly against rotational loads.

Anatomic double bundle ACL reconstruction has some logical rationales in its favor and is supported by biomechanical studies. These studies suggest that conventional single bundle ACL reconstruction may successfully restore anteroposterior knee stability, but the reconstructed knee may be unable to resist combined rotatory loads. Cadaveric studies of double bundle knee reconstructions reveal a closer restoration of normal knee kinematics and better rotational stability. A closer restoration of normal knee kinematics may be associated with improved functional outcomes following ACL reconstruction.

Reciprocal tensile behavior has long been a quest of the surgeon who performs ACL reconstructions and has been a rationale for pursuing the double bundle technique. The concept is that the AM bundle should carry more tension in flexion and the PL bundle should carry more tension in extension. A doubled-over soft tissue graft in a single tunnel may restore reciprocal tensile behavior if the tunnel has been placed to avoid PCL and roof impingement and the centers of the graft bundles can be separated and appropriately oriented at the femoral and tibial tunnel apertures.

Double bundle ACL reconstruction is not without its drawbacks. The most common cause of failure of any kind of ACL reconstruction is improper bone tunnel position. The double bundle procedure, which is more complex than the single bundle technique, may be expected to have more misplaced tunnels. For example, dual tunnels can interfere with each other when they are not meticulously positioned. In particular, a poorly positioned PL tunnel may displace a subsequently formed AM tunnel too far anteriorly, resulting in roof impingement and potential graft rupture.

The double bundle procedure has other potential disadvantages. The greater complexity of double bundle repair results in longer surgical time. Two separate grafts need to be prepared, four tunnels need to be prepared, and four separate fixation devices are required.

Suitable femoral fixation options may be limited. Currently, the EndoButton™ may be the most common femoral fixation device for a double bundle ACL reconstruction due to its low profile. Cross-pin femoral fixation may not be feasible for double bundle ACL reconstruction due to anatomical constraints in the vicinity of the femoral tunnel apertures.

The larger tibial footprint of a double bundle ACL reconstruction offers greater potential for femoral notch impingement by the graft. Larger cross-sectional areas of graft tissue traverse the intercondylar notch in a double bundle ACL reconstruction. This may result in PCL impingement as well as notch impingement simply due to the size of the grafts. PCL impingement has been seen even in single bundle ACL reconstructions. PCL impingement may occur when the tibial tunnel is placed in a vertical orientation at an angle >70 degrees from the medial joint line of the tibia and the femoral tunnel is then drilled through the tibial tunnel. Vertical placement of the ACL graft at the apex of the femoral notch may cause the graft to wrap around the PCL, which may cause high tension in the graft when the knee is flexed. High graft tension in flexion may cause the graft to stretch out or may prevent the patient from regaining full knee flexion. Preventing PCL impingement in single bundle ACL reconstructions requires a femoral notchplasty as well as placement of the femoral tunnel further down the sidewall of the intercondylar notch. PCL impingement may not be an issue with double bundle reconstructions, because the femoral tunnels may be placed in the anatomic footprint of the ACL through an inferomedial arthroscopic portal. However, when two femoral tunnels are separated by a bone bridge (often 2 mm wide), the composite area may extend outside the border of the anatomic ACL footprint. This effectively increases the cross-sectional area of the graft and "overstuffs the notch." Furthermore, the cross-sectional area of the native ACL as it crosses the PCL is approximately 54.4 square mm, and may be significantly less in smaller people. Therefore, if double bundle ACL reconstruction with a standard size graft is performed with dual femoral and tibial tunnels, the effective cross-sectional area of the graft may exceed 100 square mm. Notch or PCL impingement, loss of knee flexion and eventual stretching and failure of the tissue may result.

Revision is also more difficult with double bundle ACL reconstruction than with single bundle ACL reconstruction. A significant volume of bone is consumed with a four tunnel technique. It may be problematic to place revision tunnels anatomically if there is no bone into which to drill. In order to ensure correct graft placement at the time of revision, a bone grafting procedure may be required to fill the vacant bone tunnels, followed by a second procedure to revise the ACL reconstruction.

Thus, there exists a need in the art for novel ACL reconstruction devices that provide the strength of cortical fixation, the stiffness of aperture fixation, and osteoconductivity for bony ingrowth to allow circumferential healing of the graft/tunnel interface. There also exists a need for a method of fixation that separates an ACL graft into bundles such that knee kinematics are restored without the need for separate bone tunnels and multiple soft tissue grafts. There also exists a need in the art for an ACL reconstruction technique that produces bone tunnels that more closely replicate the anatomic femoral and tibial ACL footprints, uses a single graft separated into bundles to restore the kinematics of the native ACL, and eliminates the problems of increased surgical time and complexity, difficult revision, notch impingement and PCL impingement that are inherent with the current double tunnel, double bundle ACL technique. There also exists a need in the art to provide a fixation implant that can be used to deliver specific therapeutic agents, such as biochemicals that allow for tendon to bone healing or enhance osteoinductivity such that bone may grow into the fixation implant.

SUMMARY OF THE INVENTION

The present invention provides a novel single tunnel, double bundle ACL reconstruction system and method that overcomes the problems and disadvantages associated with current designs and strategies in ACL reconstruction, such as increased surgical time and complexity, difficult revision, notch impingement, and PCL impingement. The present invention may anchor a soft tissue graft to bone through a combination of cortical fixation and aperture fixation, and may provide osteoconductive aperture fixation to facilitate circumferential healing of the graft/tunnel interface. The present invention may divide a single strand of graft into a plurality of bundles, and may anatomically orient the bundles to restore normal knee kinematics. The present invention may anchor multiple graft bundles in a single femoral or tibial tunnel, which may be positioned and sized to substantially overlap the anatomic ACL footprint. The present invention may provide a single tunnel, with an hourglass shaped cross section, in each of the femur and the tibia. Alternatively, the cross section of the tunnel may be bowtie shaped, figure eight shaped, dumbbell shaped, bicuspid epicycloid, or Gerono lemniscate. The present invention may deliver therapeutic agents to the graft implantation site.

Graft preparation may involve standard soft tissue graft preparation techniques including cutting the graft to the correct length, whip-stitching the free ends of the graft with strong suture, and sizing the graft prior to tunnel preparation. The graft may be folded over a trial implant component and inserted into one of several differently sized apertures in a sizing block. The differently sized apertures may be available in half millimeter or other reasonable increments such that the graft may be progressively forced through smaller apertures so that it will fit tightly in the bone tunnel. The shape of the apertures may correspond to the shape of the bone tunnels. The double bundle technique may be practiced with any size or type of graft, and may preferably use an 8-9 mm graft, although a graft up to 14 mm is contemplated. The graft may be placed under tension to eliminate creep in the graft and subjected to other graft preparation techniques at the discretion of the surgeon.

The femoral tunnel contemplated in the present invention may have an hourglass or figure eight cross section, or any of the other shapes set forth above. In one embodiment, the figure eight shape may be created by drilling two overlapping tunnels: an AM tunnel through the center of the anatomic footprint of the AM bundle of the ACL and a PL tunnel through the anatomic footprint of the PL bundle of the ACL. The AM and PL tunnels may be drilled to the same depth, resulting in a single femoral tunnel with an hourglass shaped cross-section contained within the footprint of the native ACL. The AM tunnel may be drilled over a guide wire placed through the center of the AM bundle footprint, and the PL tunnel may be drilled through a drill guide that references the AM tunnel, or vice versa. The drill guide may have a post that fits into the tunnel, or it may be cannulated to fit over the guide wire. The drill guide may protect the medial femoral condyle and PCL from the drill bit. The drill guide may establish a desired offset between the centers of the AM and PL tunnels. The offset may be determined by referencing the lateral intercondylar ridge and the posterior aspect of the lateral femoral condyle through a medial arthroscopic portal. The drill guide may alternatively be used to place a guide wire for the PL tunnel, over which a drill is subsequently used. The femoral PL tunnel may be oriented anterior and slightly inferior to the AM tunnel, with respect to the tibia with the knee flexed.

The femoral tunnel may be shaped to the appropriate final size using a series of hourglass shaped tamps provided in half millimeter or other reasonable increments. The femoral tunnel may be sized to produce an appropriate press fit with the graft/implant construct. The shaping process may smooth and compact the tunnel walls, thereby increasing their density. The shaping process may produce a flat floor or end of the tunnel. Alternatively, the shaping process may produce a tapered or funnel-shaped floor of the tunnel. The tamps may be cannulated to guide the insertion of a guide wire for a cortical tunnel, or to guide the insertion of a drill bit to drill the cortical tunnel. If a guide wire is inserted, the tamp may then be removed and the cortical tunnel may be drilled from the femoral tunnel to the lateral femoral cortex. The cortical drill bit may have incremental markings which may serve as a depth gage. The smaller diameter cortical tunnel may accommodate a cortical fixation device, such as a cortical button.

Alternatively, the femoral tunnel may be created by drilling a single tunnel through the center of the entire ACL footprint and shaping the tunnel to the appropriate size and shape using the tamps. In a further alternative embodiment, the femoral tunnel may be created by shaping alone. In yet another embodiment, the femoral tunnel may be created using a shaped broach or chisel.

The tibial tunnel contemplated in the present invention may have an hourglass or figure eight cross section, or any of the other shapes set forth above. The tibial tunnel may be formed by a procedure similar to any of the procedures set forth above with regard to the femoral tunnel. The tibial tunnel may be formed with a drill guide designed so that conjoined tunnels may be drilled from outside-in through an anteromedial approach. An AM bundle guide wire may be placed so that it passes through the center of the anatomic footprint of the AM bundle of the ACL on the tibial plateau and just anterior to the medial collateral ligament (MCL) and pes anserinus insertions on the anteromedial aspect of the tibia. A PL tunnel may be drilled using an offset drill guide placed over the guide wire. The drill guide may receive a drill, or it may receive a guide wire over which a drill may subsequently be passed. The PL tunnel may be angled just posterior and lateral to the AM tunnel to allow more anatomic orientation of the tibial insertion of the graft while remaining contained within the tibial footprint of the ACL. The conjoined tibial tunnels may also be shaped in half millimeter or other reasonable increments to compress the cancellous bone and allow for easy graft insertion.

A femoral graft construct may be prepared by assembling the prepared graft, a femoral implant, a suture loop, and a cortical fixation device. The femoral implant may be sized and shaped to press fit into the constricted midsection at the mouth of the femoral tunnel. The femoral implant may comprise a porous biocompatible material, and may comprise one or more therapeutic agents. The graft may be draped over the femoral implant so that a graft bundle extends along either side of the femoral implant. The suture loop may connect the femoral implant to the cortical fixation device. In an alternate embodiment, the graft construct may comprise the prepared graft and a femoral implant. In this embodiment, a separate cross pin fixation device may be used.

Graft passage technique may include passing a suture loop through the tibial tunnel, into the femoral tunnel, through the lateral cortex and through the lateral soft tissues of the thigh. This loop may be used to draw the femoral graft construct into the femoral tunnel. A tool may be used to push a tight graft construct through the tibial tunnel, across the joint, and into the femoral tunnel. The femoral tunnel geometry may urge the graft bundles into the preferred orientation. The femoral implant may be seated to a predetermined depth in the femoral tunnel to provide a tight press fit of both graft bundles to the periphery of the tunnel walls. This may limit graft micromotion and optimize the chance for tendon to bone healing or bone ingrowth into a porous embodiment of the femoral implant. In one embodiment, the femoral implant may be preloaded with an osteoinductive protein or other growth factor prior to insertion into the knee. This may be performed on the back table prior to femoral implant insertion. The cortical fixation device may be secured to the suture loop so that the cortical fixation device engages the lateral femoral cortex. The cortical fixation device may provide firm, stable cortical fixation for the construct. After the femoral graft construct is secured in place, a graft tensioning instrument may be used to apply tension to the graft.

Tibial fixation then follows in the preferred technique. The strands of the graft may be placed under tension with the knee at roughly 30 degrees of flexion. The tibial implant may be tamped into place in the center of the graft strands (2 or 4). The tibial implant may be tamped to the measured depth of the tunnel such that the spacer on the nose of the implant may be at the joint line. The tibial implant should not protrude into the joint and the strands of the graft should not be drawn into the knee as the tibial implant is advanced into the tunnel. A funnel-shaped tunnel floor or aperture may limit the tibial implant from advancing into the joint. An appropriately sized tapered screw may be inserted distal to the tibial implant, again with maximum tension on the graft. The screw may thread into wings extending from the tibial implant spacer. The wings may expand as the screw is threaded into place, providing an interference fit along the length of the tibial tunnel. The spacer at the end of the tibial implant may compress the graft into the periphery of the conjoined tunnels. This may provide aperture fixation at the tibial interface. Cortical fixation may then be achieved with a stemmed button that fits into the hexagonal slot in the interference screw and has a head diameter greater than the tunnel diameter. Graft sutures may be passed through slots in the button and tied down in standard fashion to provide cortical fixation. This embodiment of a tibial implant provides double fixation of the graft with both stable cortical fixation and aperture fixation so that the tibial implant resists tension, torsion, and bending forces on the graft.

Alternatively, a single tunnel may be drilled through the tibia and femur, followed by an hourglass shaped tamp which shapes the tunnels into a corresponding hourglass shaped cross section which mimics the anatomic footprint of the ACL on the tibia and femur. The femoral end of the graft may be secured with a cortical fixation device remote from the joint space and secured with a femoral implant adjacent to the joint space, thus providing both cortical and aperture fixation. The tibial end of the graft may likewise be secured with a tibial implant adjacent to the joint space and a cortical fixation device remote from the joint space. An intra-tunnel tibial fixation device, such as an interference screw, may alternatively be used instead of an extracortical fixation device. The femoral or tibial implant may force the graft to interact with the outer wall of the tunnel adjacent to the joint space.

The femoral or tibial implant may be fabricated of PEEK, polyglycolic acid (PGA), polylactic acid (PLLA), allograft bone, autograft bone, metal, metal alloys, polymers, ceramic, glass, or any other biocompatible material, or any combination of the preceding materials. The implant may be porous, and may preferably be made of porous polymer such as polyetheretherketone (PEEK). The pore structure of the implant may mimic the pore structure of cancellous bone. The implant may have a solid portion and a porous portion, such as a solid core with a porous outer layer, or a porous first end and a solid second end. An at least partially porous implant may prove to be osteoconductive. Graft fixation may be optimized by press fitting the graft in an hourglass shaped tunnel with a porous femoral or tibial implant whose pore size is similar to that of cancellous bone; this construct may achieve initial stiff aperture fixation and long term bone ingrowth.

The implant may include one or more agents, for example: osteobiologic proteins, hydroxyapatite (HA), allograft morselized bone, autograft morselized bone, orthobiologics, anesthetics, analgesics, antimicrobial agents, growth proteins, growth factors, bone morphogenic proteins (BMP), stem cells, osteoprogenitor cells, or platelet rich plasma. The agents may be included in the implant by, for example, injection, infusion, coating, intrinsic incorporation, spraying, dipping, soaking, or dusting. One or more holes, apertures, or cavities in the implant may house the agent. The implant may allow for delayed release or customizable dosing of the agents. The implant may act as a delivery system for osteoinductive factors and may encourage neovascularization or ligamentization of the graft tissue itself over time.

The polymer femoral or tibial implant may be advantageous for revision because a drill will readily pass through PEEK or other polymer, regardless of its porosity.

In an alternate embodiment, the hourglass shaped femoral or tibial tunnel may be asymmetrically shaped so that the graft and implant may only be inserted in one orientation.

The apparatus and method of the present invention may facilitate separately tensioning each graft bundle. For example, one bundle may be tensioned while the knee is in extension, generally −10 degrees to 45 degrees, and the other bundle may be tensioned while the knee is in flexion, generally 45 degrees to 145 degrees. In a preferred embodiment, the present invention may facilitate tensioning the PL bundle at a roughly 30 degree bend and the AM bundle at a roughly 90 degree bend. Alternatively, all bundles may be tensioned in flexion, extension, or in an intermediate position.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 14A is a perspective view of an alternate embodiment of a drill; and FIG. 14B is a detail view of an end of the drill of FIG. 14A;

DETAILED DESCRIPTION

The present invention advances the state of the art by providing apparatus and methods for single tunnel, double bundle ACL reconstruction.

In this specification, standard medical directional terms are employed with their ordinary and customary meanings. Superior means toward the head. Inferior means away from the head. Anterior means toward the front. Posterior means toward the back. Medial means toward the midline, or plane of bilateral symmetry, of the body. Lateral means away from the midline of the body. Proximal means toward the trunk of the body. Distal means away from the trunk.

In this specification, a standard system of three mutually perpendicular reference planes is employed. A sagittal plane divides a body into bilaterally symmetric right and left portions. A coronal plane divides a body into anterior and posterior portions. A transverse plane divides a body into superior and inferior portions.

Figure 1:
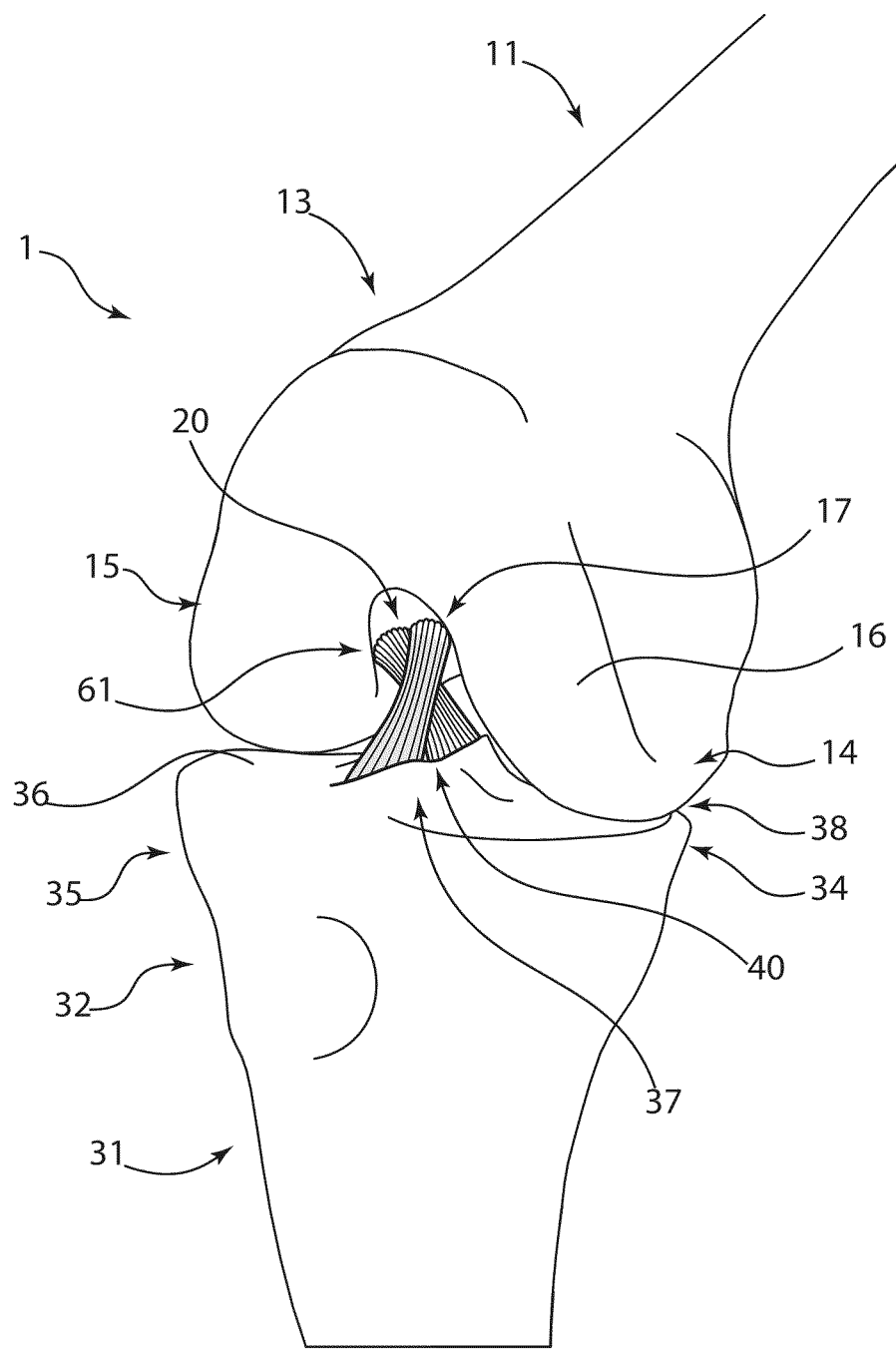
FIG. 1 is an antero-medial perspective view of a right knee joint, showing a femur, a tibia, and an intact anterior cruciate ligament.

Referring to FIG. 1, a right knee joint 1 is shown in an antero-medial perspective view. More specifically, FIG. 1 shows a distal end 13 of a right femur 11, a proximal end 32 of a right tibia 31, and an anterior cruciate ligament (ACL) 61 connecting the femur 11 and tibia 31. The distal end 13 of the femur 11 has a medial condyle 14 and a lateral condyle 15, which are separated by an intercondylar notch 17. A cartilaginous articular surface 16 covers portions of the medial condyle 14 and the lateral condyle 15. The proximal end 32 of the tibia 31 has a medial condyle 34 and a lateral condyle 35, which are separated by an intercondylar eminence 37. The medial condyle 34, lateral condyle 35, and intercondylar eminence 37 may be collectively referred to as a tibial plateau 38. A cartilaginous articular surface 36 covers portions of the medial condyle 34 and lateral condyle 35. The ACL 61 is formed of dense regular connective tissue characterized by large amounts of densely packed strands of organized collagenous fibers.

Figure 2:
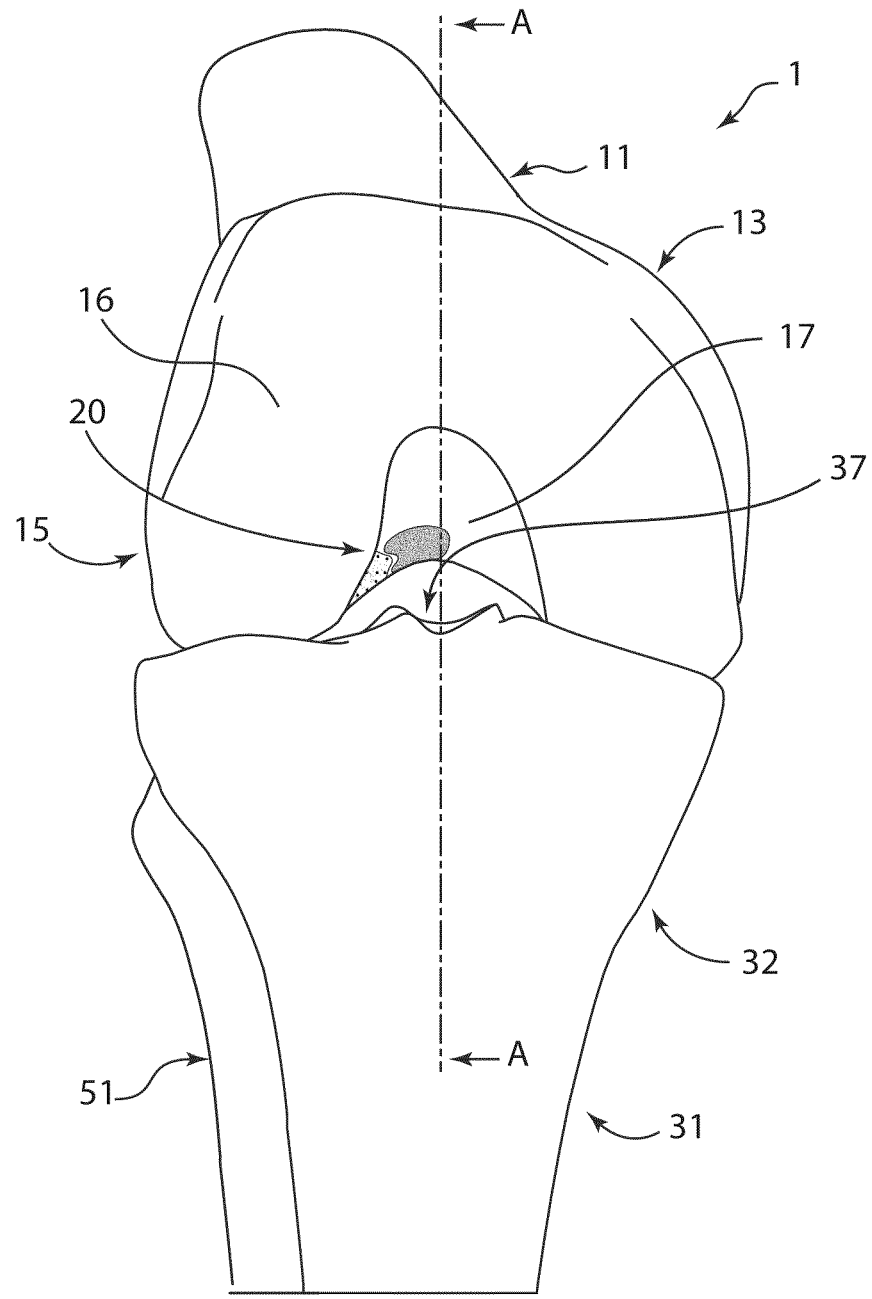
FIG. 2 is an anterior view of the knee joint of FIG. 1, showing the femur and tibia and a fibula.

Referring to FIG. 2, the knee 1 of FIG. 1 is shown in an anterior view with the knee 1 flexed to about 90 degrees. Fibula 51 is visible in its natural anatomic relationship to the tibia 31. The ACL 61, not shown, has been removed to reveal an attachment area 20 on the lateral aspect of the intercondylar notch 17, or in other words, on the medial aspect of the lateral condyle 15. The ACL 61 attaches to femur 11 at attachment area 20. Attachment area 20 may be referred to as the femoral footprint of the ACL 61. A cross section line A-A is shown across the distal end 13 of the femur 11 and the proximal end 32 of the tibia 31, generally parallel to the sagittal plane and generally centered in the intercondylar notch 17.

Figure 3:
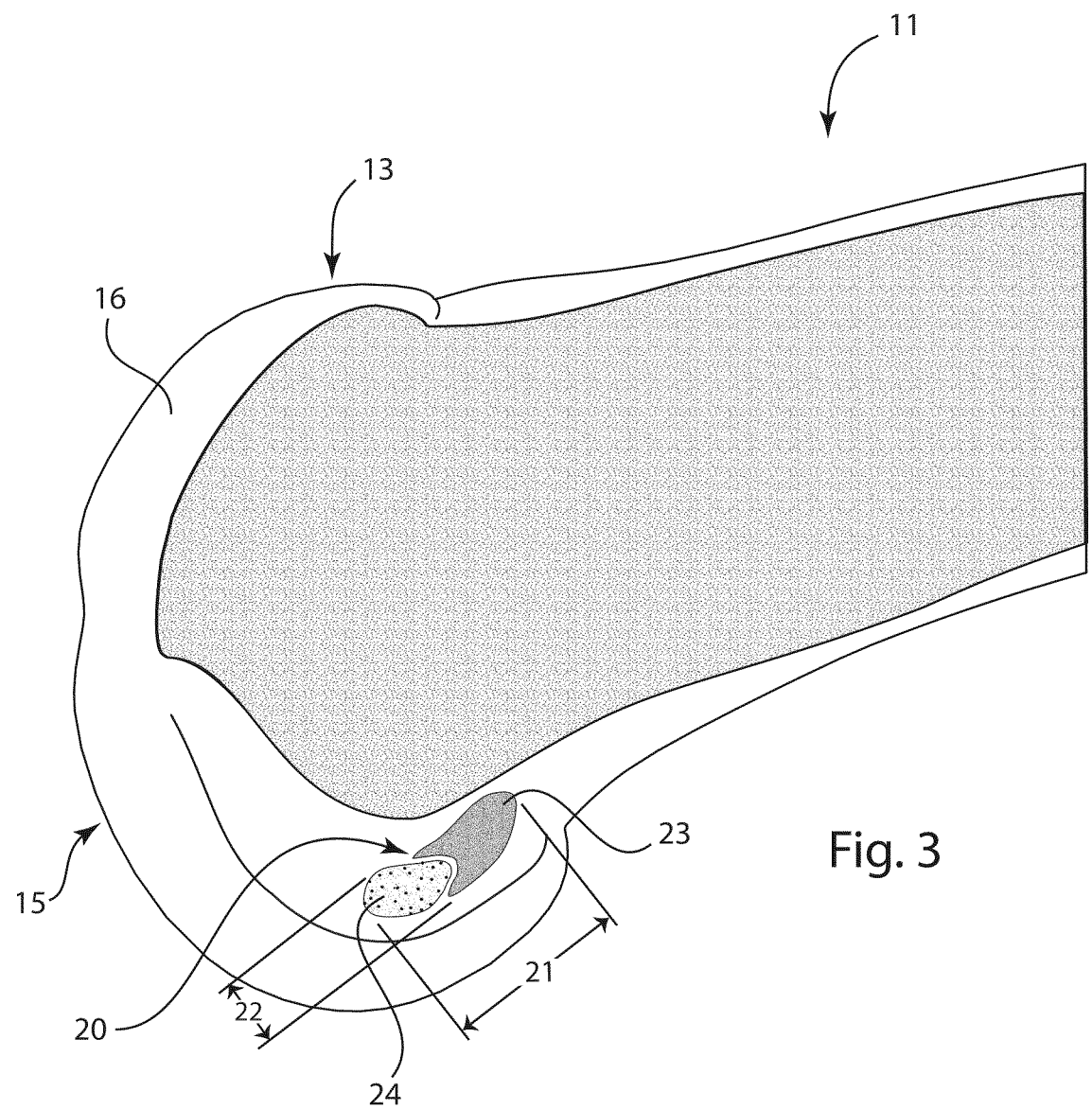
FIG. 3 is a cross sectional view of the femur of FIG. 2.

Referring to FIG. 3, the femur 11 of FIG. 2 is shown in a cross sectional view taken along line A-A, shown in FIG. 2, so that the lateral condyle 15 is shown. The femoral ACL footprint, or femoral ACL attachment area 20, has a width 21 that extends generally from antero-proximal to postero-distal, and a thickness, or height 22, that is less than the width 21.

Figure 4:
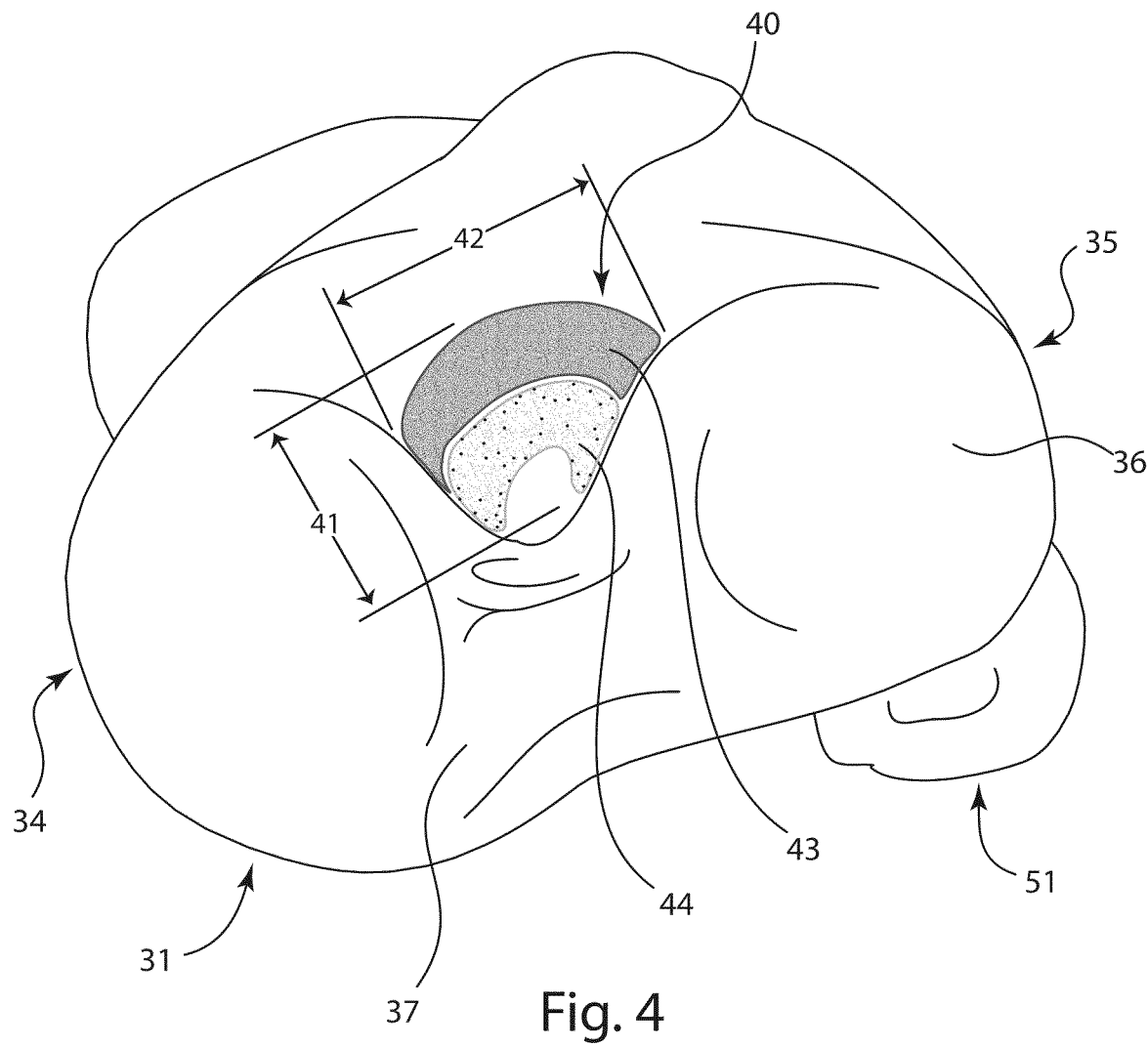
FIG. 4 is a proximal view of the tibia and fibula of FIG. 2.

Referring to FIG. 4, the tibia 31 and fibula 51 of FIG. 2 are shown in a proximal view. The ACL 61, not shown, has been removed to reveal an attachment area 40 in the anterior portion of the intercondylar eminence 37, hence the name "anterior cruciate ligament." The ACL 61 attaches to the tibia 31 at attachment area 40. Attachment area 40 may be referred to as the tibial footprint of the ACL 61. The tibial ACL footprint, or tibial ACL attachment area 40, has a width 41 that extends generally from antero-medial to postero-lateral, and a thickness, or height 42, that is less than the width 41.

Figure 5:
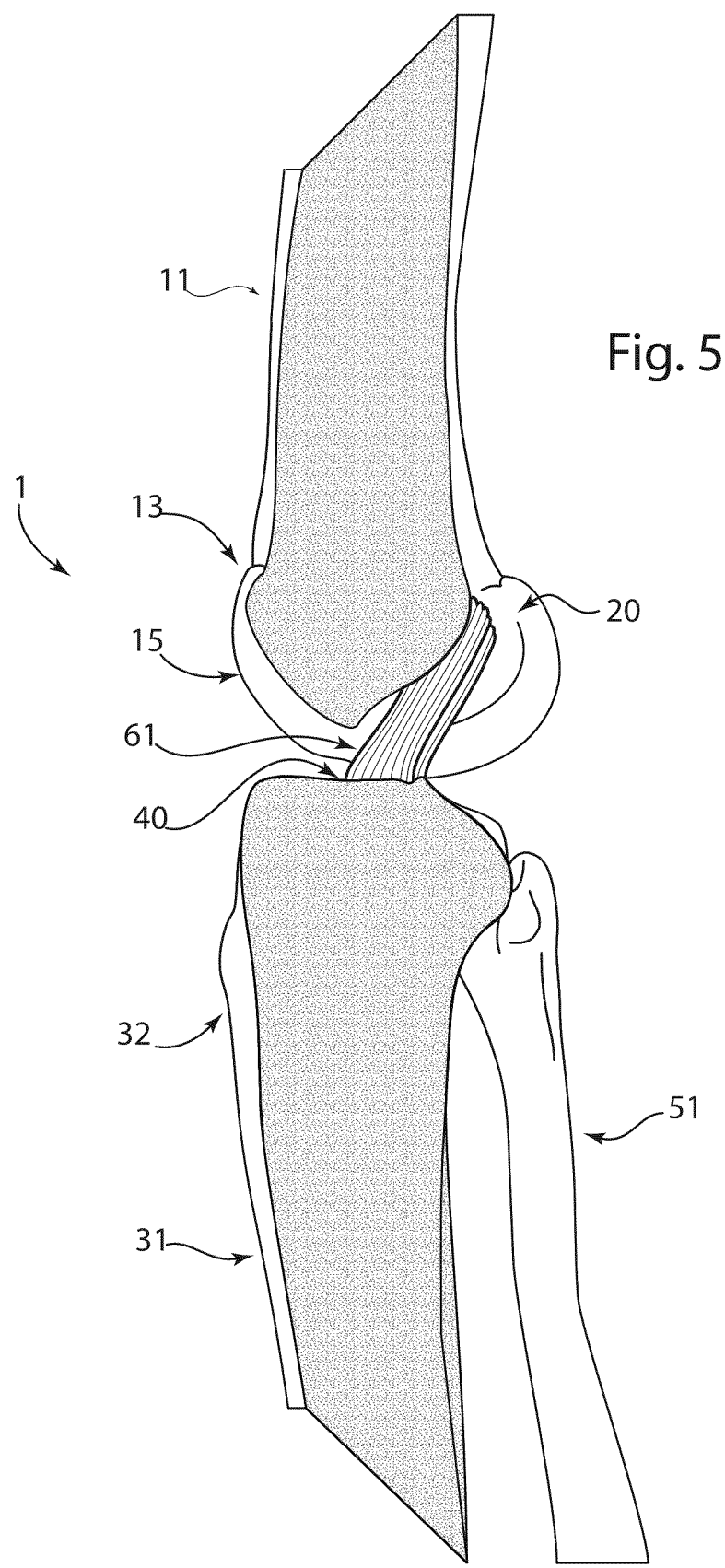
FIG. 5 is a lengthwise cross sectional view of the knee joint of FIG. 2 in extension.

Referring to FIG. 5, the knee joint 1 of FIG. 2 is shown in a cross sectional view taken along line A-A, shown in FIG. 2. The knee 1 is fully extended, or in other words, the knee 1 is straight. When the knee 1 is fully extended, the individual strands of the ACL 61 extend generally in parallel between the femoral and tibial ACL attachment areas 20, 40. Strands extend between the antero-medial portion of the tibial ACL attachment area 40 and the antero-proximal portion of the femoral ACL attachment area 20. Likewise, strands extend between the postero-lateral portion of the tibial ACL attachment area 40 and the postero-distal portion of the femoral ACL attachment area 20.

Figure 6:
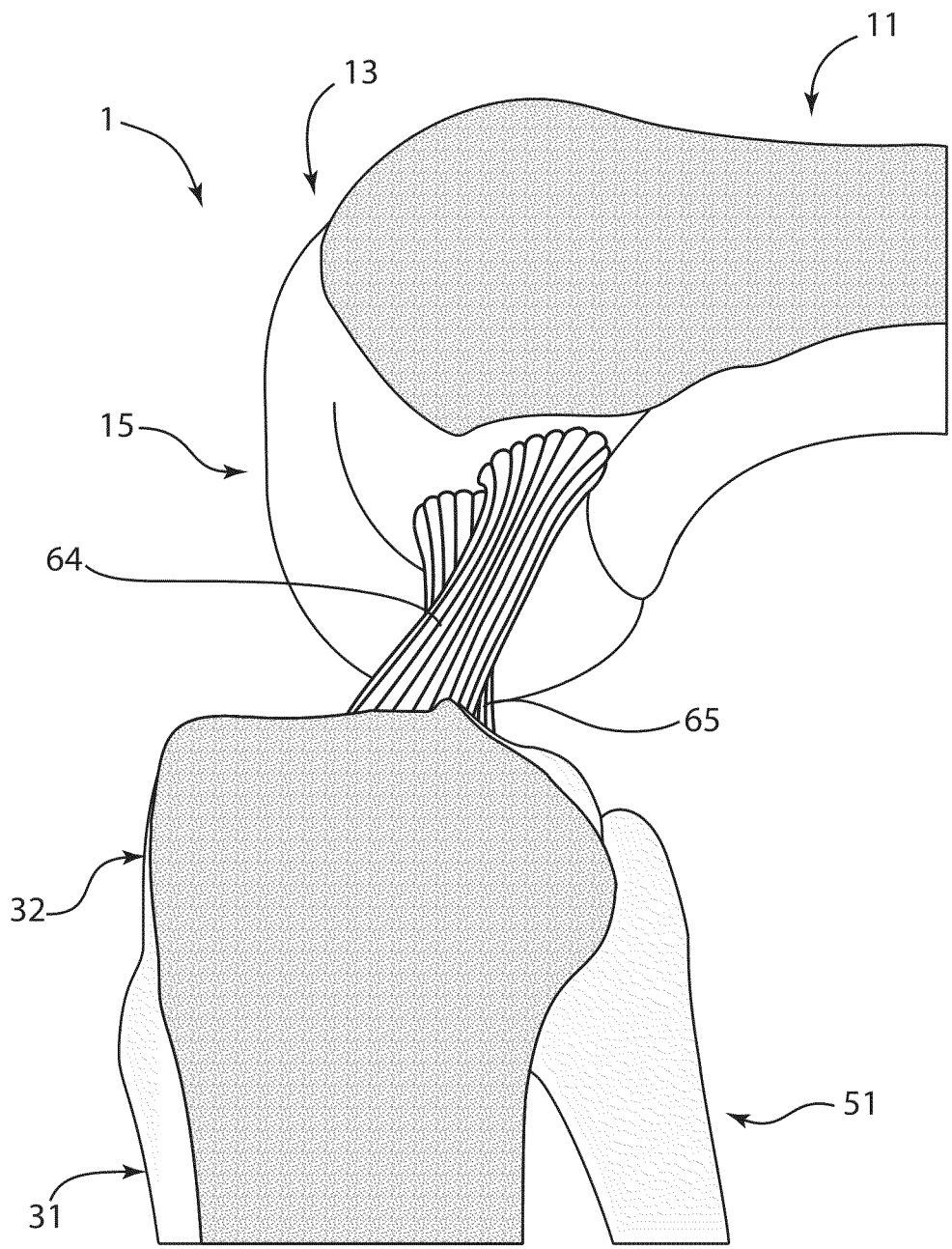
FIG. 6 is a lengthwise cross sectional view of the knee joint of FIG. 2 in about 90 degrees of flexion.

Referring to FIG. 6, the knee joint 1 of FIG. 2 is shown in a cross sectional view taken along line A-A, shown in FIG. 2. The knee 1 is flexed to about 90 degrees. In FIG. 6, the relative orientation of the femoral ACL attachment area 20 to the tibial ACL attachment area 40 has changed in comparison to FIG. 5 due to relative rotation of the femur 11 and tibia 31. In FIG. 6, the antero-proximal portion of the femoral ACL attachment area 20 is closer to the postero-lateral portion of the tibial ACL attachment area 40 and the postero-distal portion of the femoral ACL attachment area 20 is closer to the antero-medial portion of the tibial ACL attachment area 40. As a result, the ACL 61 is twisted when the knee 1 is flexed. It can be readily observed in FIG. 6 that the ACL 61 has at least two bundles which cross each other when the knee 1 is flexed. A first bundle 64 attaches to the antero-medial portion of the tibial ACL attachment area 40 and a second bundle 65 attaches to the postero-lateral portion of the tibial ACL attachment area 40. For the remainder of this specification, the first bundle 64 shall be called the antero-medial (AM) bundle 64 and the second bundle 65 shall be called the postero-lateral (PL) bundle 65.

Each bundle of the ACL 61 makes a unique kinematic contribution to knee function. The AM bundle 64 is moderately lax in extension and tight in flexion. It is the main anterior-posterior stabilizer. The PL bundle 65 is tight in extension and lax in flexion. It is the main rotational stabilizer.

Returning to FIGS. 3-4, it can be appreciated that the femoral ACL attachment area 20 may be divided into an AM area 23 where the AM bundle 64 attaches to the femur 11 and a PL area 24 where the PL bundle 65 attaches to the femur 11. Likewise, the tibial ACL attachment area 40 may be divided into an AM area 43 where the AM bundle 64 attaches to the tibia 31 and a PL area 44 where the PL bundle 65 attaches to the tibia 31.

Referring to FIGS. 7-10, implant constructs according to the present invention are shown. The implant constructs may be used to secure an ACL reconstruction graft in the knee joint 1 (FIG. 1). The implant constructs, and individual components thereof, will be set forth and described prior to a discussion of surgical methods for preparing the knee joint 1 and inserting the exemplary implant constructs.

Figure 7:
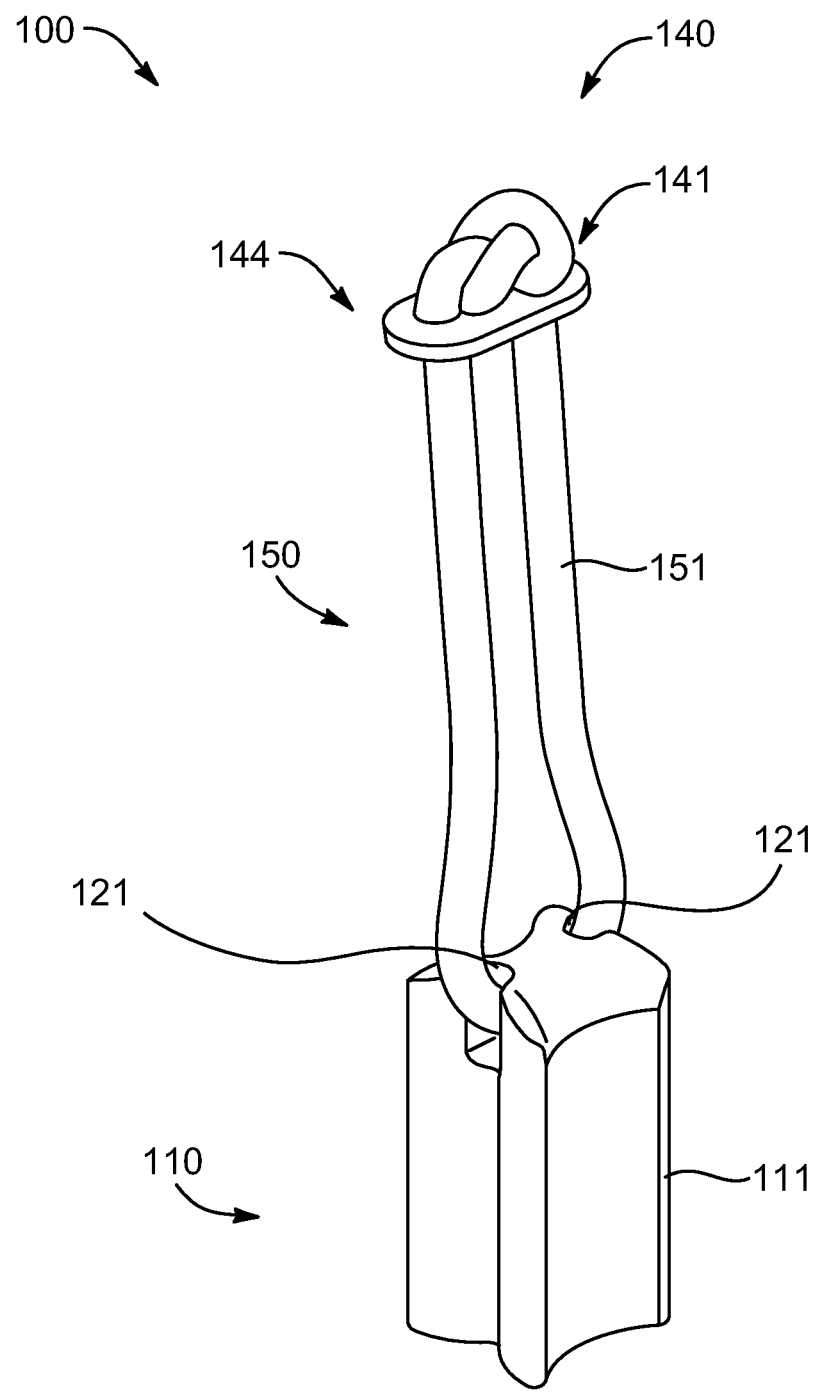
FIG. 7 is a perspective view of an implant construct according to the present invention, showing a first fixation device, a second fixation device, and a connector.

Referring to FIG. 7, a femoral implant construct 100 is shown. The construct 100 may include a first fixation device 110, a second fixation device 140, and a connector 150. In this embodiment, the first fixation device may be a plug 111, the second fixation device may be a button 141, and the connector 150 may be a flexible loop 151. The plug 111 may be connected to the button 141 by the loop 151. The plug 111 may include cutouts 121, or notches, for receiving the flexible loop 151.

Figure 8A:
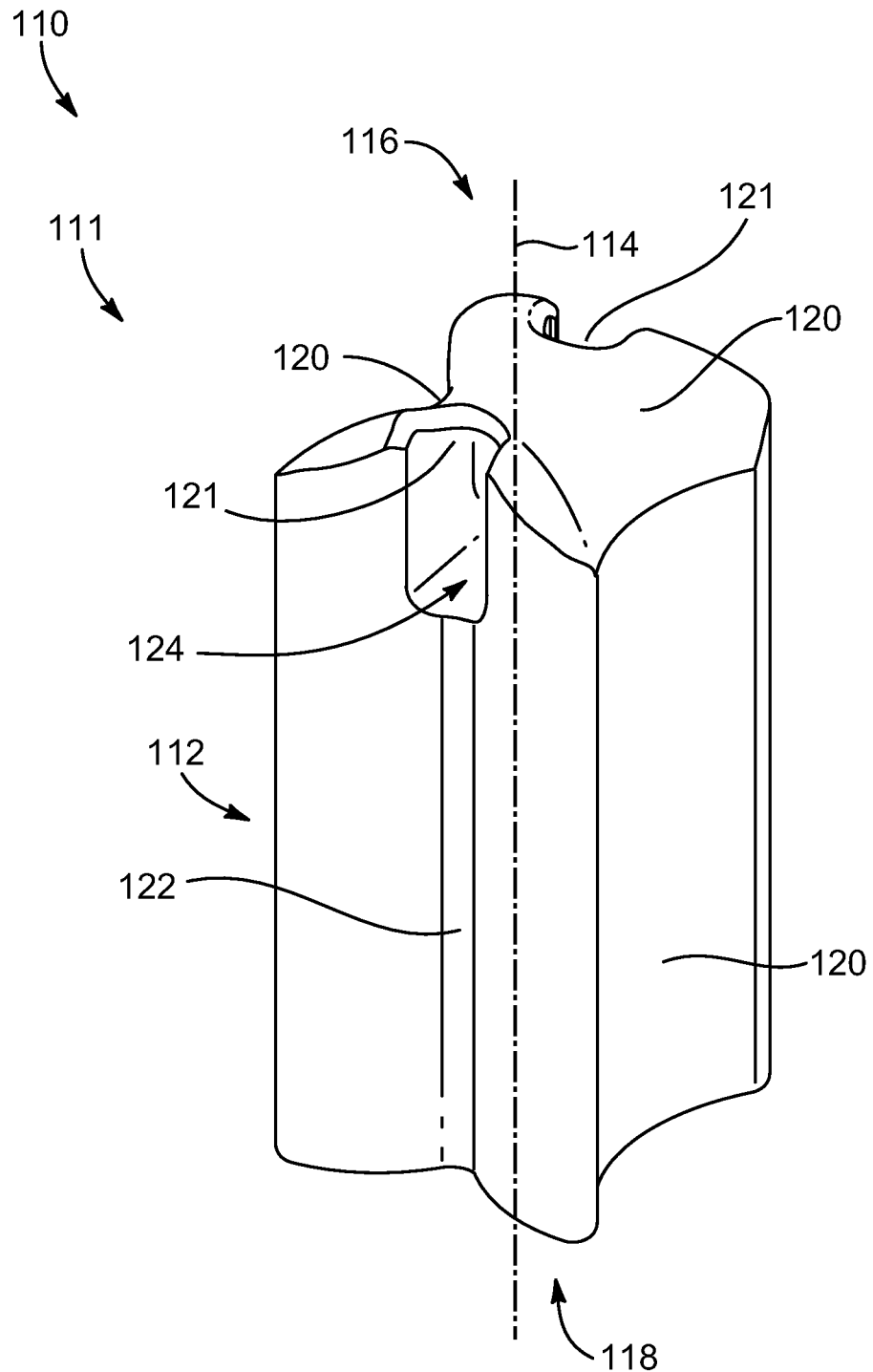
FIG. 8A is a perspective view of the first fixation device of FIG. 7.
Figure 8B:
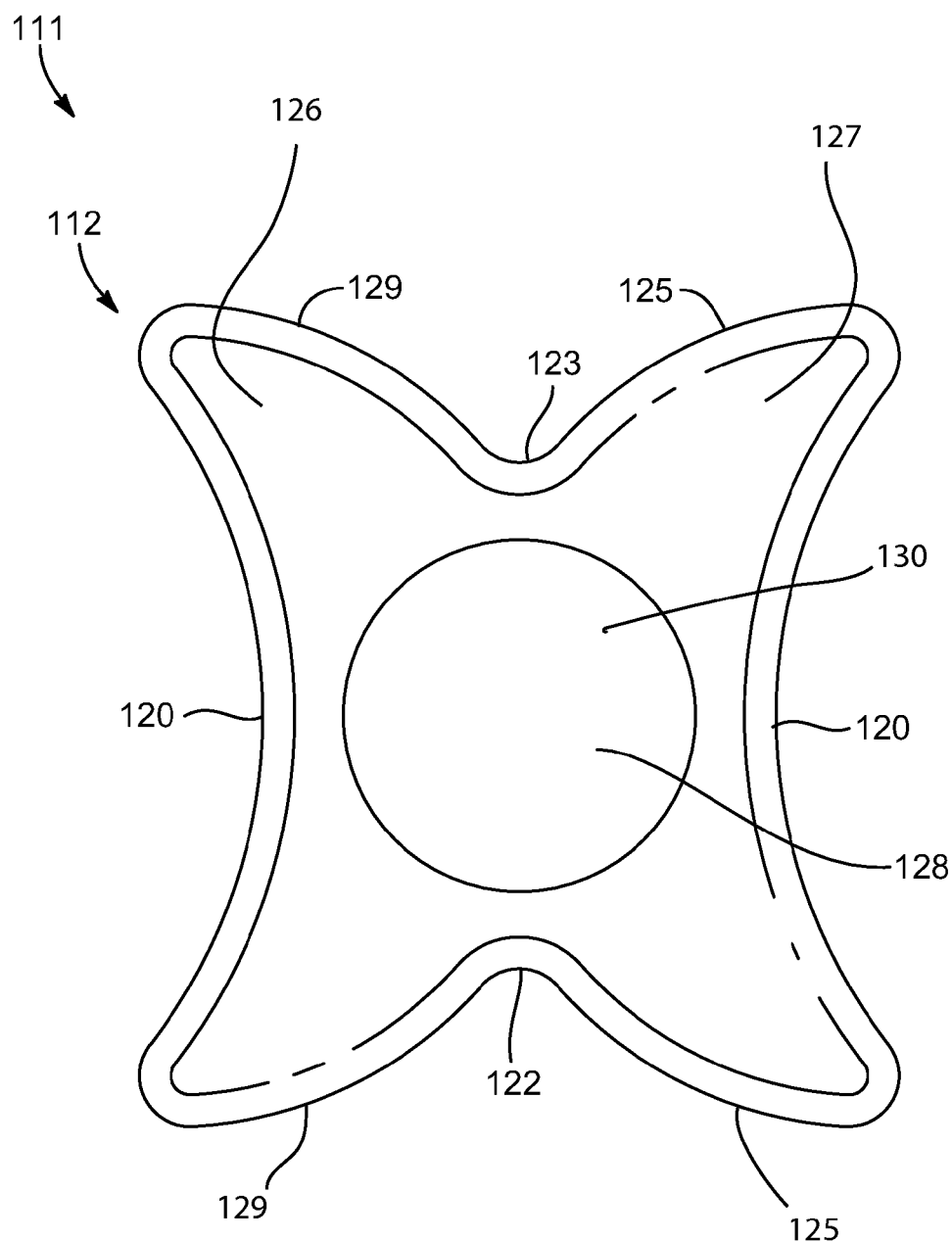
FIG. 8B is an end view of the first fixation device of FIG. 8A.

Referring to FIGS. 8A and 8B, the plug 111 of FIG. 7 has a body 112 that may extend along a longitudinal axis 114 from a leading end 116 to a trailing end 118. The leading end 116 may include a leading surface and the trailing end 118 may include a trailing surface. A groove 120 may extend across the leading end 116 and at least partially across a leading surface and also generally parallel to the axis 114 along opposite sides of the body 112. Individual portions of the groove 120 may blend smoothly to form a U-shaped or horseshoe-shaped composite feature on the body 112. A plurality of indentations 122, 123 may be interposed between the grooved sides of the body 112 and may extend generally parallel to the axis 114 along opposite sides of the body 112. The body 112 may also have an aperture 124 extending through the body 112. The aperture 124 may be located proximate the leading end 116 or the trailing end 118, or may be more centrally located. With reference to FIG. 7, it can be appreciated that the aperture 124 may accept a portion of the loop 151 so as to connect the plug 111 to the loop 151. The aperture 124 may be in connection with and open to the cutouts 121. The cutouts 121 may be substantially U-shaped in at least one cross-section and extend toward a center of the body of the plug 111, and may be more pronounced than the indentations 122, 123.

With reference to FIG. 8B, the body 112 is shown from the trailing end 118. In this embodiment, the profile shown in FIG. 8B may be constant over at least a portion of the length of body 112. Therefore, the body 112 shown in FIG. 8B may be described as a cross section projected along the axis 114 (shown in FIG. 8A) from the leading end 116 to the trailing end 118. In this embodiment, the bottom view profile from the trailing end 118 shown in FIG. 8B may be described as a pair of open crescent portions 126, 127 formed in back-to-back relationship and having a common central portion 128 extending between the indentations 122, 123. This embodiment may include a hole 130 in the trailing end 118 which may extend at least partially into the body 112. The indentations 122, 123 formed by the back-to-back open crescent portions 126, 127 have convex portions 125, 129. The convex portions 125, 129 can transition into concave portions towards the center of the body 112 to form concave shaped indentations 122, 123 as shown in FIG. 8B.

The plug 111 may be conveniently formed in a variety of sizes and shapes to offer an array of plugs from which to select. By way of non-limiting example, the length of the plug 111 may be varied, or the radius and depth of the groove 120 may be varied. Variation of any dimension of the plug 111 is contemplated within the scope of the present invention. The plug 111 may be formed with a plurality of grooves 120 or a plurality of indentations 122, 123. A kit of plugs may be provided by packaging the array of plugs together in a container. Alternatively, the kit may comprise a selection of plugs which may be packaged individually, or not packaged at all.

The plug 111 may be formed of a material such as metal, polymer, ceramic, or biological tissue. The plug 111 may be formed entirely of a porous material, or may have a porous portion combined with a non-porous portion. In one embodiment, the plug 111 may be formed of a porous polymer such as porous polyetheretherketone (PEEK). The plug 111 may incorporate one or more therapeutic agents for encouraging bony or fibrous ingrowth into the plug 111 or surrounding tissues, for preventing infection, for reducing pain or inflammation, for preventing tissue rejection, or for other therapeutic purposes.

Returning to FIG. 7, the button 141 may have a wide, flat body 142. The body 142 may also have an aperture 144 extending through the body 142. It can be appreciated that the aperture 144 may accept a portion of the loop 151 so as to connect the button 141 to the loop 151. In this manner, the plug 111 may be connected to the button 141.

The second fixation device 140 may alternatively be, by way of non-limiting example, an anchor, a toggle fastener, a screw and washer, a nail, a staple, an interference screw, a rivet, a wedge plug, or a cross pin.

The second fixation device 140 may be formed of a material such as metal, polymer, ceramic, or biological tissue. The second fixation device 140 may be formed entirely of a porous material, or may have a porous portion combined with a non-porous portion. The second fixation device 140 may incorporate one or more therapeutic agents for encouraging bony or fibrous ingrowth into the second fixation device 140 or surrounding tissues, for preventing infection, for reducing pain or inflammation, for preventing tissue rejection, or for other therapeutic purposes.

With continued reference to FIG. 7, the loop 151 may be formed of a material such as metal, polymer, ceramic, textile, or biological tissue. The loop 151 may be formed as a monofilament, round braid, flat braid, ribbon, chain, or zip tie. The loop 151 may be continuously formed, or secured with a splice, knot, adhesive, or clamp. Alternatively, the first fixation device 110 may be connected to the second fixation device 140 by a linear connector 150 instead of a loop 151. As another alternative, the first fixation device 110 may connect directly to the second fixation device 140 without requiring a separate connector 150.

Figure 9:
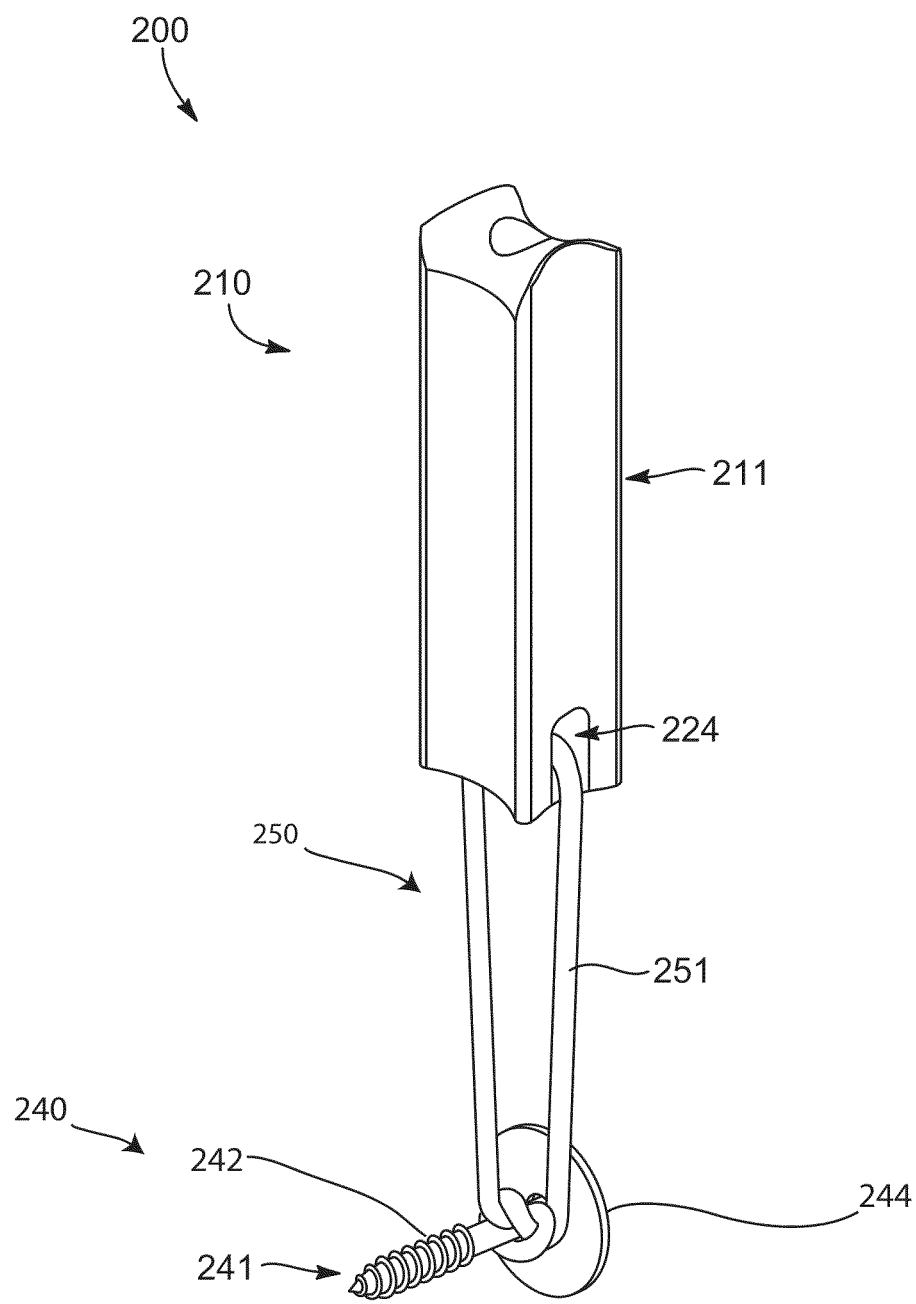
FIG. 9 is a perspective view of an alternate embodiment of an implant construct according to the present invention, showing a first fixation device, a second fixation device, and a connector.

Referring to FIG. 9, a tibial implant construct 200 is shown. The construct 200 may include a first fixation device 210, a second fixation device 240, and a connector 250. In this embodiment, the first fixation device may be a plug 211, the second fixation device may be a screw construct 241, and the connector 250 may be a flexible loop 251. The plug 211 may be connected to the screw construct 241 by the loop 251.

Figure 10A:
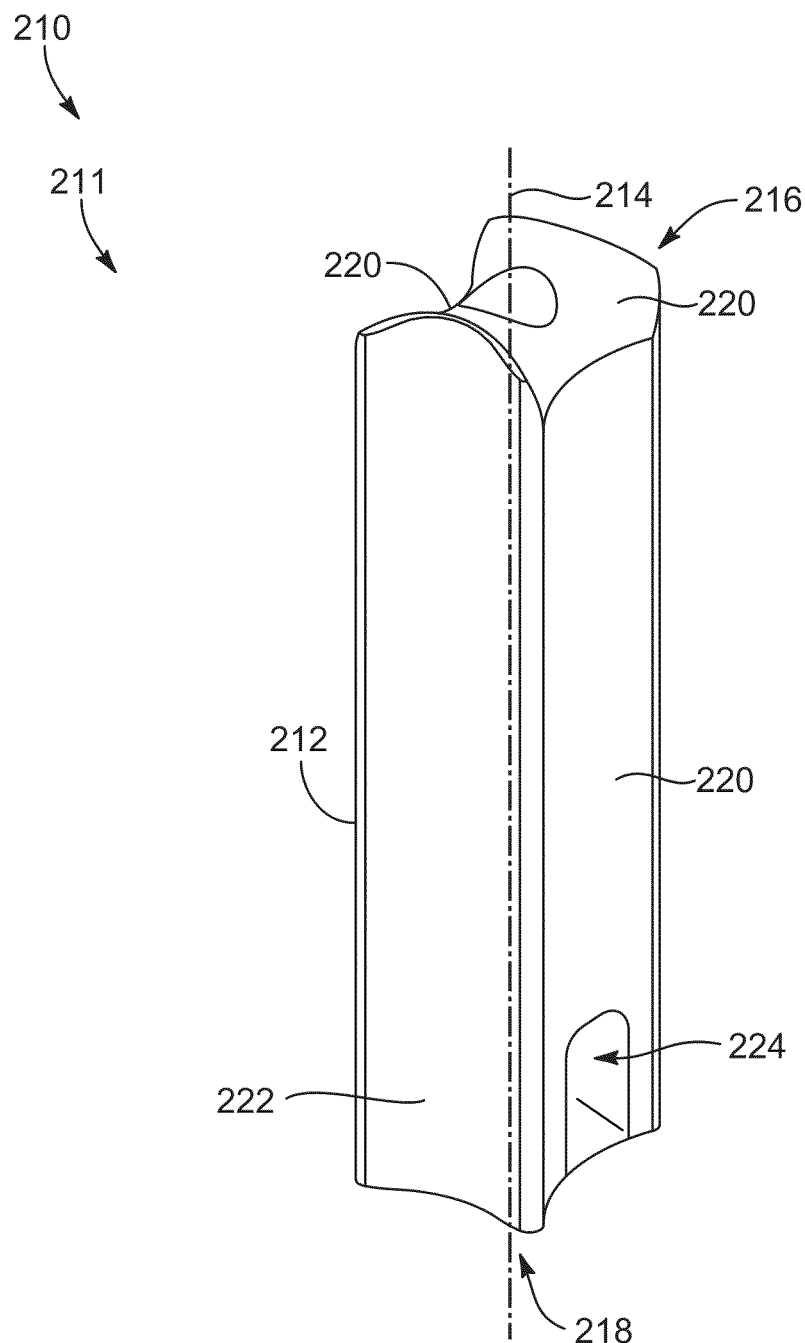
FIG. 10A is a perspective view of the first fixation device of FIG. 9.
Figure 10B:
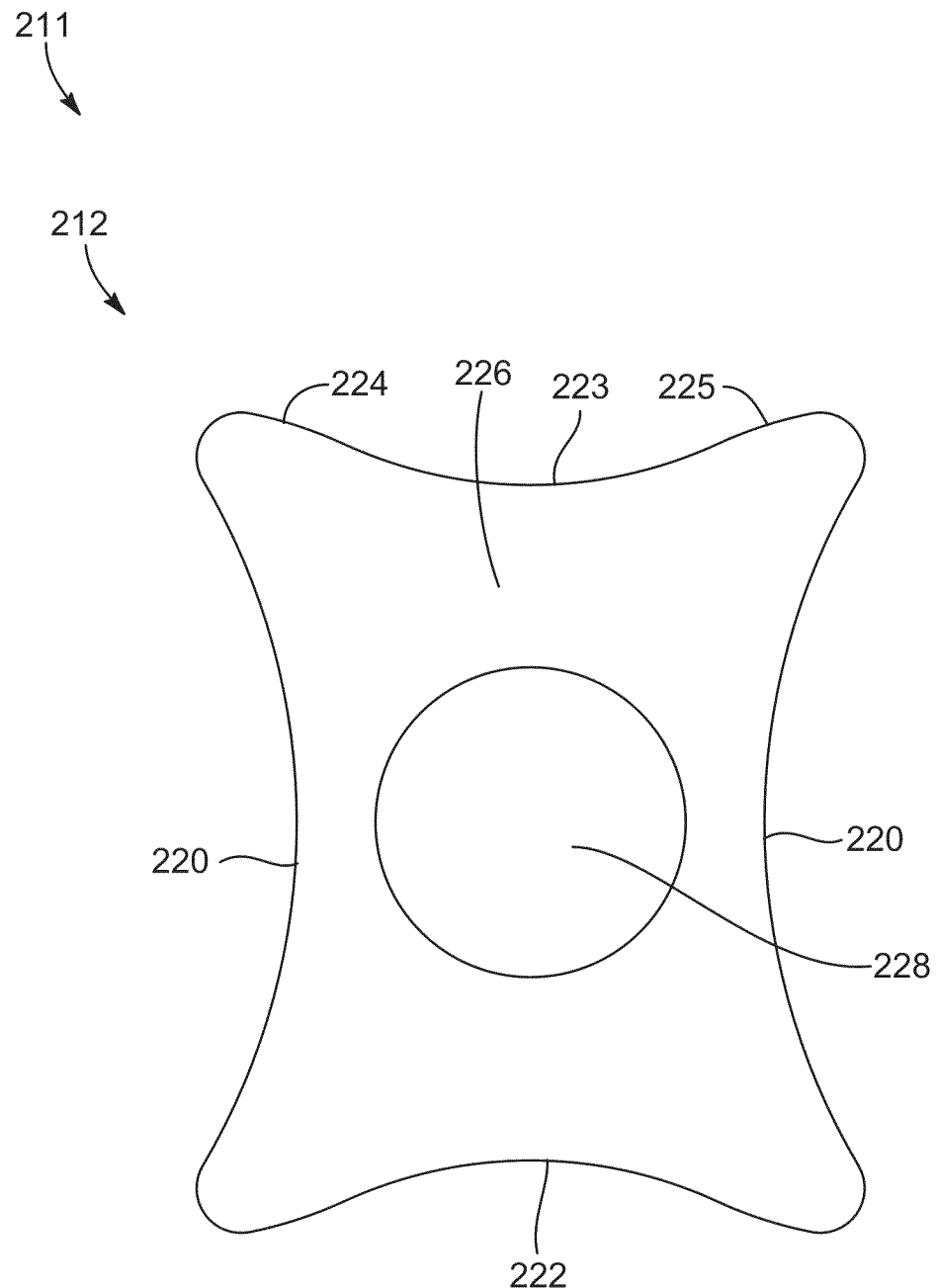
FIG. 10B is an end view of the first fixation device of FIG. 10A.

Referring to FIGS. 10A and 10B, the plug 211 of FIG. 9 has a body 212 that may extend along a longitudinal axis 214 from a leading end 216 to a trailing end 218. A groove 220 may extend across the leading end 216 and generally parallel to the axis 214 along opposite sides of the body 212. Individual portions of the groove 220 may blend smoothly to form a U-shaped or horseshoe-shaped composite feature on the body 212. Alternatively, the groove 220 may be discontinuous so that the groove 220 extends only along opposite sides of the body 212 and is absent across the leading end 216. A pair of indentations 222, 223 may be interposed between the grooved sides of the body 212 and may extend generally parallel to the axis 214 along opposite sides of the body 212. In this embodiment, the indentations 222, 223 have a larger radius than the indentations 122, 123 of the femoral plug 111. The body 212 may also have an aperture 224 extending through the body 212. The aperture 224 may be located proximate the leading end 216 or the trailing end 218, or centrally located. With reference to FIG. 9, it can be appreciated that the aperture 224 may accept a portion of the loop 251 so as to connect the plug 211 to the loop 251.

With reference to FIG. 10B, the body 212 is shown from the trailing end 218. In this embodiment, the profile shown in FIG. 10B is constant over at least a portion of the length of body 212. Therefore, the body 212 may be described as a cross section projected along the axis 214 (FIG. 10A) from the leading end 216 to the trailing end 218. In this embodiment, the profile shown in FIG. 10B may be described as a pair of open crescent portions 226, 227 formed in back-to-back relationship and having a common central portion 228 extending between the indentations 222, 223. This embodiment also includes a hole 230 in the trailing end 218 which may extend at least partially into the body 212.

The plug 211 may be conveniently formed in a variety of sizes and shapes to offer an array of plugs 211 from which to select. By way of non-limiting example, the length and diameter of the plug 211 may be varied, or the radius and depth of the groove 220 may be varied. The plug 211 may also be alternatively formed with a plurality of grooves 220 or a plurality of indentations 222, 223. A kit of plugs 211 may be provided by placing the array of plugs 211 together in a container. Alternatively, the kit may comprise a selection of plugs 211 which may be packaged individually, or not packaged at all.

The plug 211 may be formed of a material such as metal, polymer, ceramic, or biological tissue. The plug 211 may be formed entirely of a porous material, or may have a porous portion combined with a non-porous portion. In one embodiment, the plug 211 may be formed of a porous polymer such as porous polyetheretherketone (PEEK). The plug 211 may incorporate one or more therapeutic agents for encouraging bony or fibrous ingrowth into the plug 211 or surrounding tissues, for preventing infection, for reducing pain or inflammation, for preventing tissue rejection, or for other therapeutic purposes.

Returning to FIG. 9, the screw construct 241 may include a screw 242 and a washer 244. It can be appreciated that the screw 242 may engage a portion of the loop 251 and the washer 244 may press against the loop 251 so as to connect the screw construct 241 to the loop 251. In this manner, the plug 211 may be connected to the screw construct 241 in this embodiment.

The second fixation device 240 may alternatively be, by way of non-limiting example, an anchor, a button, a toggle fastener, a nail, a staple, an interference screw, a rivet, a wedge plug, or a cross pin.

The second fixation device 240 may be formed of a material such as metal, polymer, ceramic, or biological tissue. The second fixation device 240 may be formed entirely of a porous material, or may have a porous surface layer combined with a non-porous substrate. The second fixation device 240 may incorporate one or more therapeutic agents for encouraging bony or fibrous ingrowth into the second fixation device 240 or surrounding tissues, for preventing infection, for reducing pain or inflammation, for preventing tissue rejection, or for other therapeutic purposes.

With continued reference to FIG. 9, the loop 251 may be formed of a material such as metal, polymer, ceramic, textile, or biological tissue. The loop 251 may be formed as a monofilament, round braid, flat braid, ribbon, chain, or zip tie. The loop 251 may be continuous or secured with a splice, knot, adhesive, or clamp. Alternatively, the first fixation device 210 may be connected to the second fixation device by a linear element instead of a loop 251. As another alternative, the first fixation device 210 may connect directly to the second fixation device without requiring a separate connection component.

Referring to FIGS. 11-19 and 34-35, a set of instruments according to the present invention is shown. The set of instruments may be used to prepare the knee joint 1 (FIG. 1) to receive one or more implant constructs according to the present invention. The individual instruments will be set forth and described prior to a discussion of surgical methods for preparing the knee joint 1 and inserting the exemplary implant constructs 100, 200.

Figure 34:
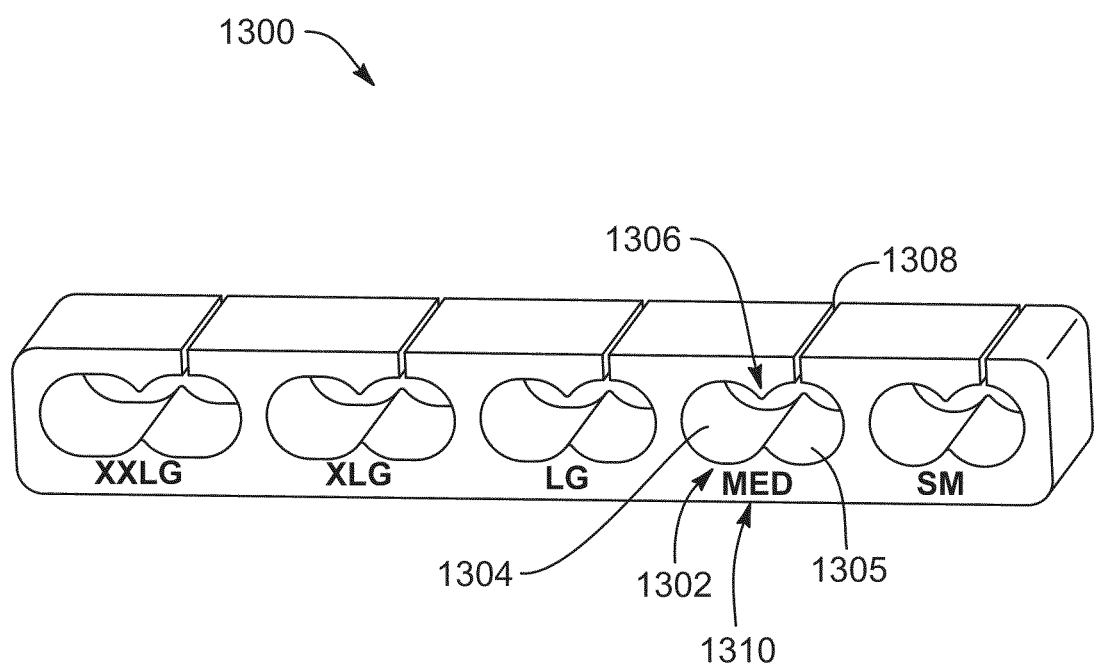
FIG. 34 is a perspective view of a graft sizing block.

Referring to FIG. 34, a graft sizing block 1300 is shown. The sizing block 1300 may have an aperture 1302 which extends through the block 1300. The aperture 1302 may be described as a plurality of enlarged lobes 1304, 1305 separated by a constricted middle section 1306, a figure eight shape, an hourglass shape, a peanut shell shape, or a bicuspid epicycloid shape. The aperture 1302 may correspond to the shape of a femoral or tibial tunnel, as will be set forth in greater detail below. A slot 1308 may intersect the aperture. The block 1300 may include a mark 1310 adjacent to the aperture 1302 to communicate information about the aperture 1302. The sizing block 1300 may include a plurality of differently configured apertures, each intersected by a slot and having an adjacent mark. The apertures may be arranged in a linear array, as shown in FIG. 34, or in a rectangular, circular, or other arrangement.

Figure 35:
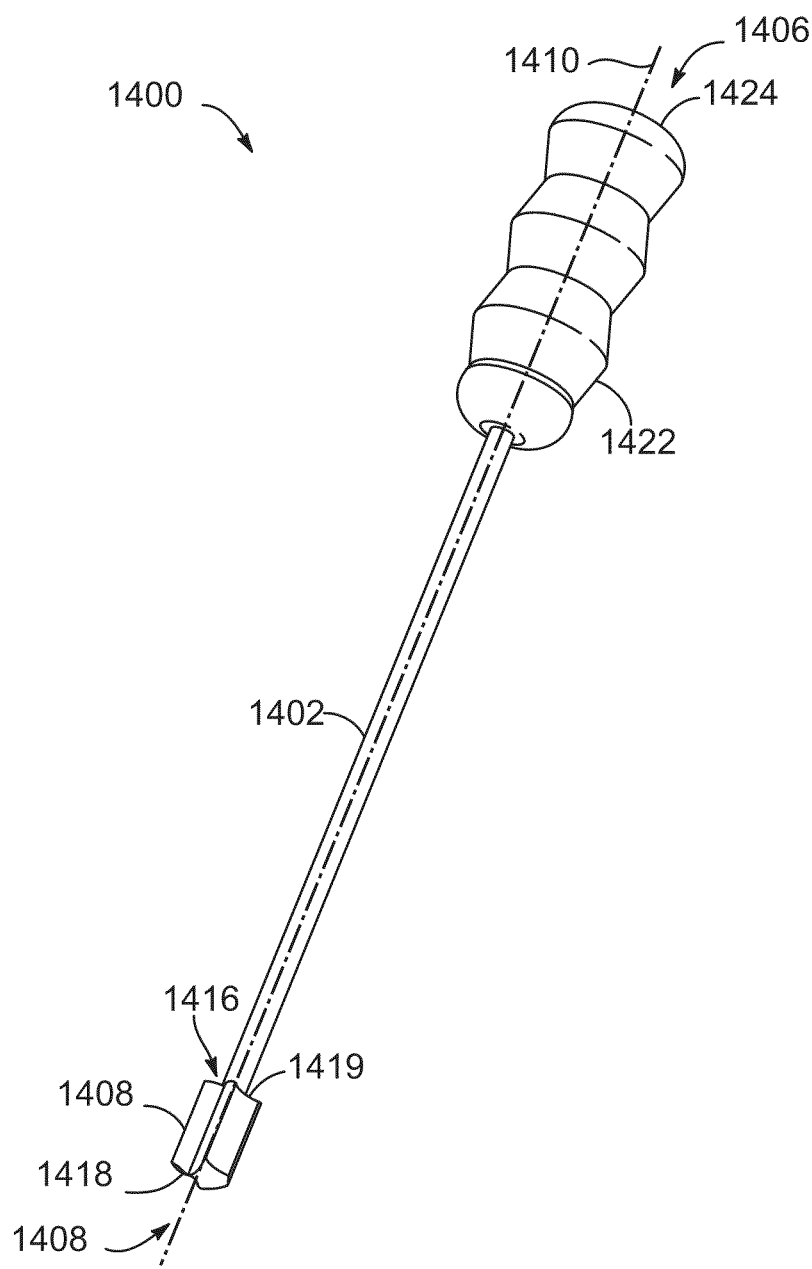
FIG. 35 is a perspective view of a trial instrument.

Referring to FIG. 35, a trial instrument 1400 is shown. The trial instrument 1400 may comprise a shaft 1402 extending at least partially between a leading end 1404 and a trailing end 1406. The leading end 1404 may have a protruding boss 1408 that may extend along a longitudinal axis 1410. The boss 1408 may have a plurality of indentations 1416, 1417 which extend generally parallel to the axis 1410 along opposite sides of the boss 1408 so as to divide the boss 1408 into a plurality of crescent shaped portions 1418, 1419 so that the boss 1408 may replicate, mimic, or resemble the plug 111 or 211. The trailing end 1406 may include a handle 1422, strike platform 1424, or other configuration.

The boss 1408 may be conveniently formed in a variety of sizes and shapes to offer an array of bosses from which to select. The boss 1408 may also be alternatively formed with more than two crescent shaped portions. A kit of modular bosses may be provided for use with one or more trial instrument assemblies consisting of shaft 1402, handle 1422, and strike platform 1424. A kit of complete trial instruments may also be provided.

Figure 11:
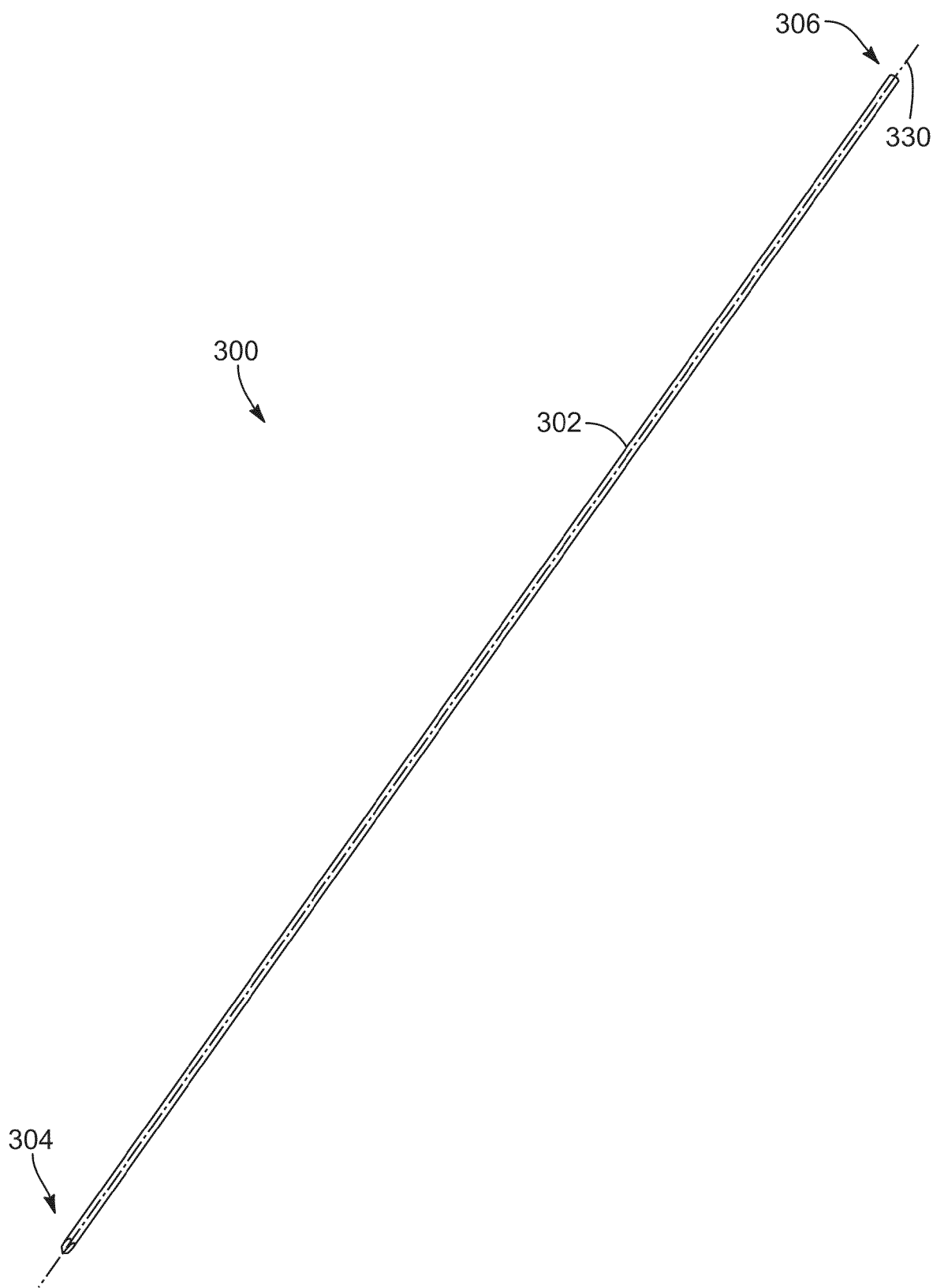
FIG. 11 is a perspective view of a guide wire.

Referring to FIG. 11, a guide wire 300 is shown. The guide wire 300 may comprise a shaft 302 with a leading end 304 and a trailing end 306. The shaft 302 has a center longitudinal axis 330. The leading end 304 may be sharpened into a point, trocar, or drill configuration.

Figures 12A, 12B:
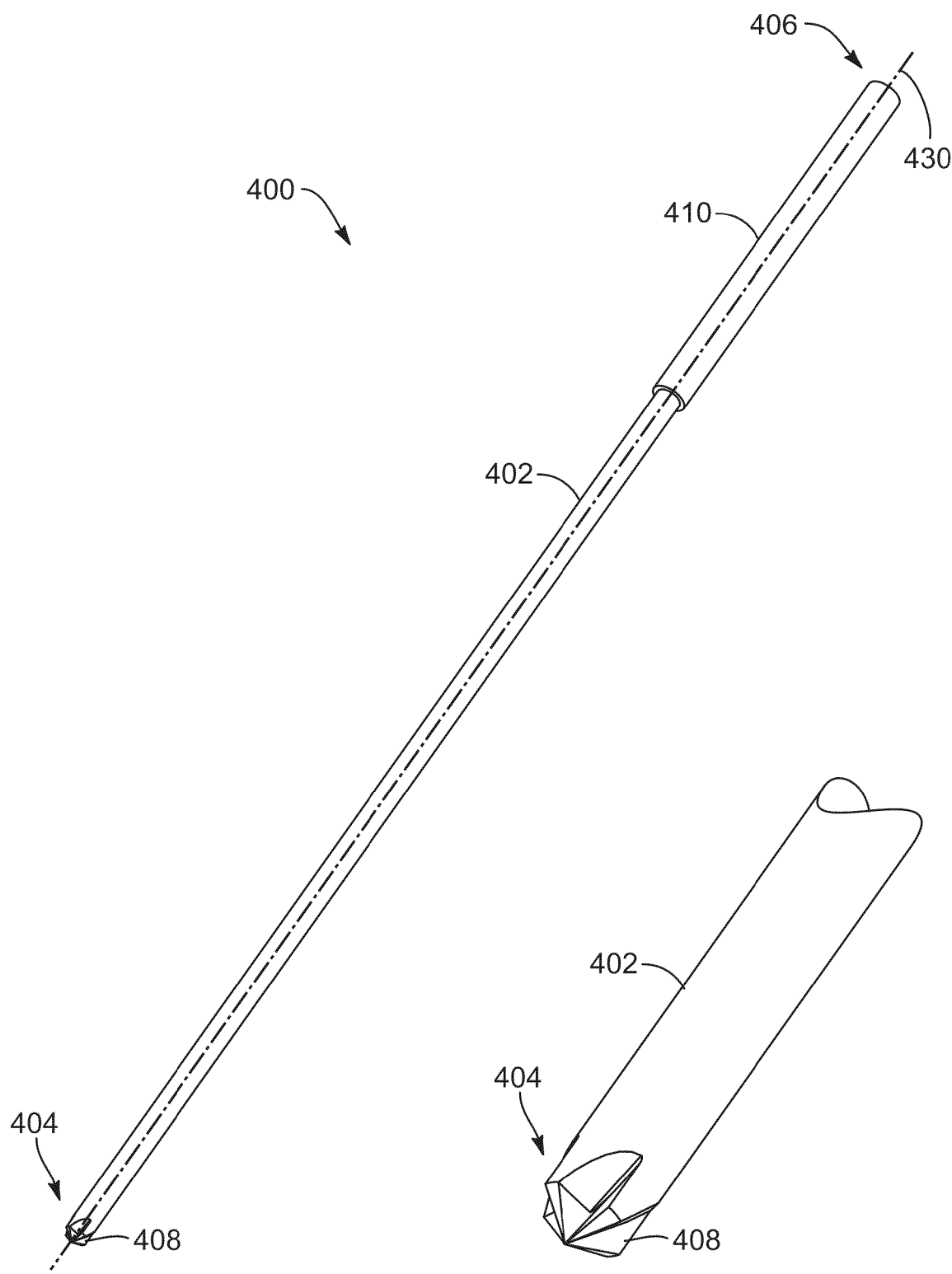
FIG. 12A is a perspective view of a drill.
FIG. 12B is a detail view of an end of the drill of FIG. 12A.

Referring to FIG. 12, a first femoral drill 400 is shown. The drill 400 may comprise a shaft 402 with a leading end 404 and a trailing end 406. The shaft 402 has a center longitudinal axis 430. The leading end 404 may be sharpened into a point, trocar, or drill configuration. In the present embodiment, a plurality of cutting flutes 408 are formed in the leading end 404 so as to produce a drill configuration. The trailing end 406 may comprise a shank 410 which may be cylindrical, otherwise known as a straight shank. Alternatively, the shank 410 may be provided with a drive configuration corresponding to a manual or power driver fitting. By way of non-limiting example, a drive configuration could comprise a hex shank, an SDS shank, a triangle shank, a Morse taper shank, a threaded shank, or a square shank. It is contemplated that any of these shank configurations could be further modified and remain within the scope of the present invention.

Figure 13:
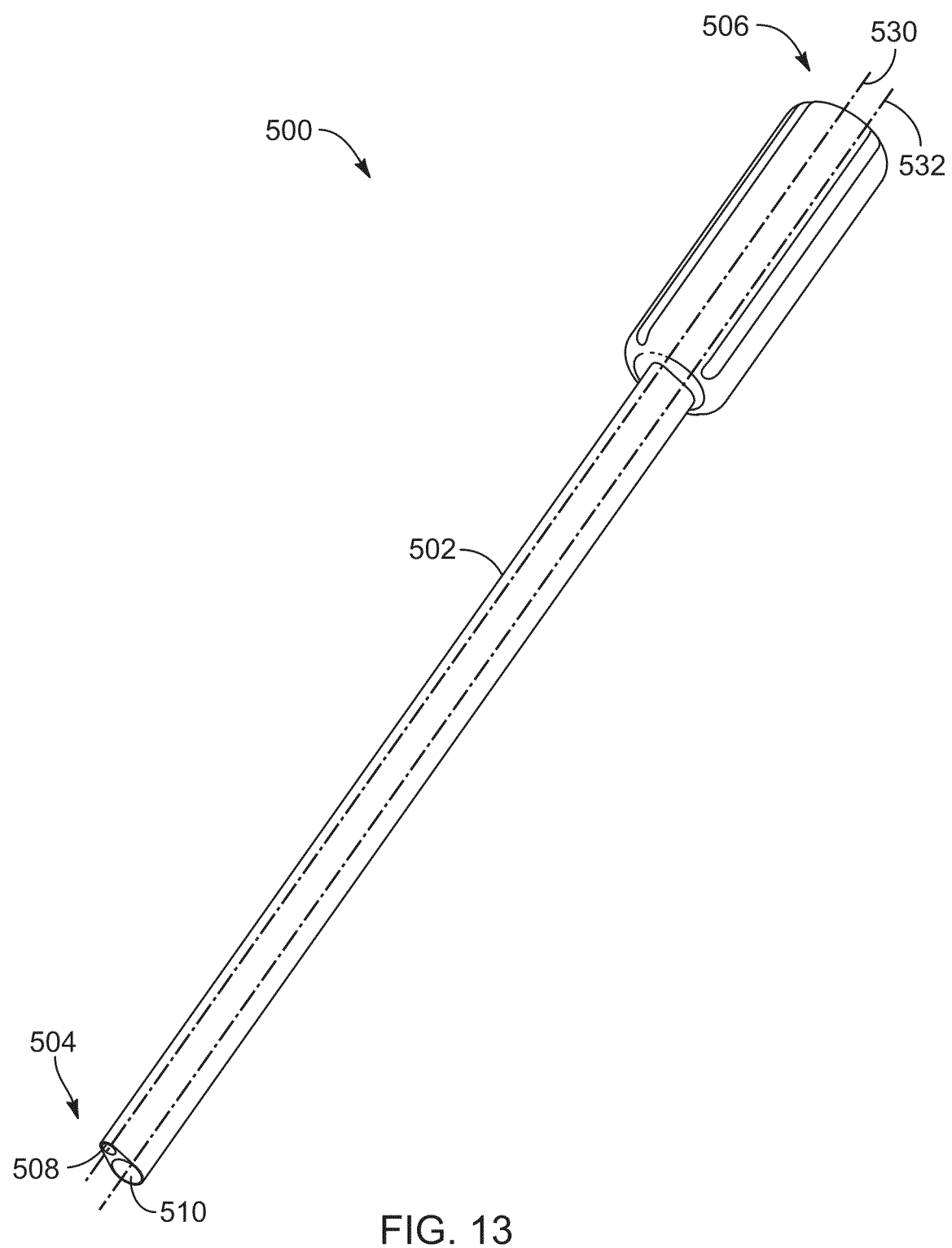
FIG. 13 is a perspective view of a drill guide.

Referring to FIG. 13, a femoral drill guide 500 is shown. The drill guide 500 may comprise a shaft 502 with a leading end 504 and a trailing end 506. One or more holes may extend through the shaft 502 from the leading end 504 to the trailing end 506. In the present embodiment, the shaft 502 has a first hole 508 and a second hole 510. The first hole 508 has a first center longitudinal axis 530 and the second hole 510 has a second center longitudinal axis 532 which is spaced apart from, and substantially parallel to, axis 530. The first hole 508 may receive the guide wire 300 with clearance so that the guide wire 300 may slide and rotate within the first hole 508. The second hole 510 may receive the femoral drill 400 with clearance so that the drill 400 may slide and rotate within the second hole 510. Alternatively, the second hole 510 may receive a second guide wire 300 with clearance so that the guide wire 300 may slide and rotate within the second hole 510.

In an alternative embodiment, not shown, the shaft 502 may lack the first hole 508. In this embodiment, the shaft may have a protruding boss at the leading end 504. The boss may be located beside hole 510, similar to the way hole 508 is beside hole 510 in FIG. 13. In this embodiment, the boss has a center longitudinal axis which is spaced apart from, and substantially parallel to, axis 532.

The drill guide may be provided in a variety of sizes to offer an array of drill guides from which to select. By way of non-limiting example, the diameter of hole 510 or the distance between axes 530 and 532 may vary. A kit of drill guides may be provided. The kit may include one or more of the drill guide embodiments set forth above, each in a variety of sizes.

Referring to FIG. 14, a second femoral drill 600 is shown. The drill 600 may comprise a shaft 602 with a leading end 604 and a trailing end 606. The leading end 604 may have a plurality of cutting flutes 608 formed in the leading end 604 to produce a drill configuration, similar to drill 400. A depth mark 612 may be present. The trailing end 606 may comprise a shank 610 which may have various configurations, as described for shank 410 of drill 400. A cannulation, or hole 614, may extend through the shaft 602 from the leading end 604 to the trailing end 506. The hole 614 has a center longitudinal axis 630. The hole 614 may receive the guide wire 300 with clearance so that the guide wire 300 may slide and rotate within the hole 614.

Figure 15A:
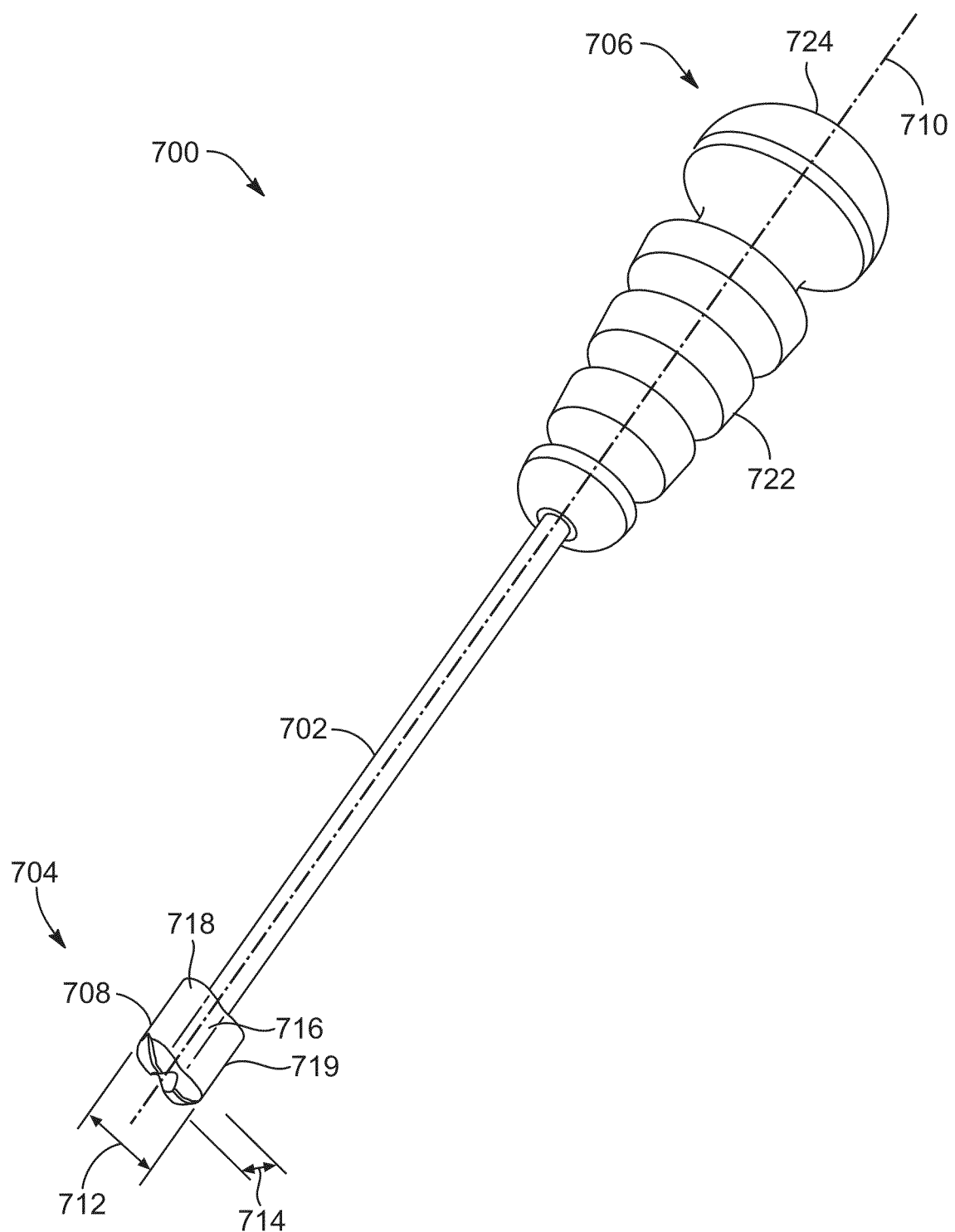
FIG. 15A is a perspective view of a tamp.
Figure 15B:
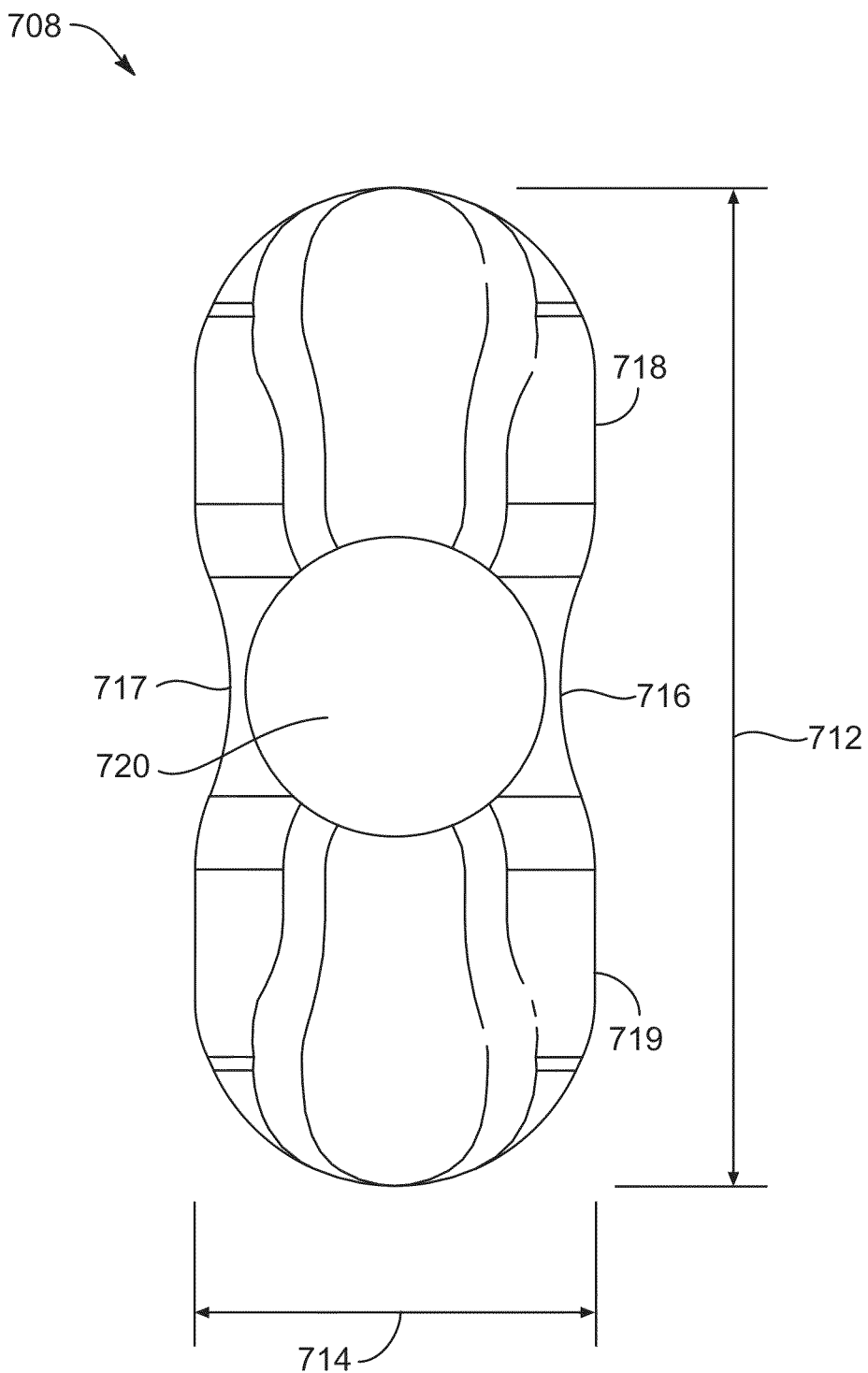
FIG. 15B is an end detail view of the tamp of FIG. 15A.

Referring to FIGS. 15A and 15B, a femoral tamp 700 is shown. The tamp 700 may comprise a shaft 702 extending at least partially between a leading end 704 and a trailing end 706. The leading end 704 may have a protruding boss 708 that may extend along a longitudinal axis 710. The boss 708 may have a width 712 and a height 714 which is less than the width 712. The width 712 and height 714 may be oriented generally perpendicular to the axis 710, as shown in FIG. 15A. The boss 708 may have a plurality of indentations 716, 717 which extend generally parallel to the axis 710 along opposite sides of the boss 708 so as to divide the width 712 of the boss 708 into a plurality of lobes 718, 719. A hole 720 may extend through the tamp 700 from the leading end 702 to the trailing end 706 along axis 710. The trailing end 706 may include a handle 722, strike platform 724, or other configuration.

Referring to FIG. 15B, the boss 708 is shown from the leading end 704. In this embodiment, the profile shown in FIG. 15B is constant over at least a portion of boss 708 in a direction generally parallel to axis 710. Therefore, boss 708 may be described as a cross section projected along the axis 710 (FIG. 15A) from the leading end 704 toward the trailing end 706. In this embodiment, the profile shown in FIG. 15B may be described as a plurality of enlarged lobes 718, 719 separated by a constricted middle section established between indentations 716, 717. Alternatively, the profile shown in FIG. 15B may be described as being shaped like a figure eight, hourglass, peanut shell, or bicuspid epicycloid curve.

The boss 708 may be conveniently formed in a variety of sizes and shapes to offer an array of bosses from which to select. By way of non-limiting example, the width 712 and height 714 of the boss 708 may be varied. The boss 708 may also be alternatively formed with more than two lobes. A kit of modular bosses may be provided for use with one or more femoral tamp assemblies consisting of shaft 702, handle 722, and strike platform 724. A kit of complete femoral tamps may also be provided.

Figures 16A, 16B:
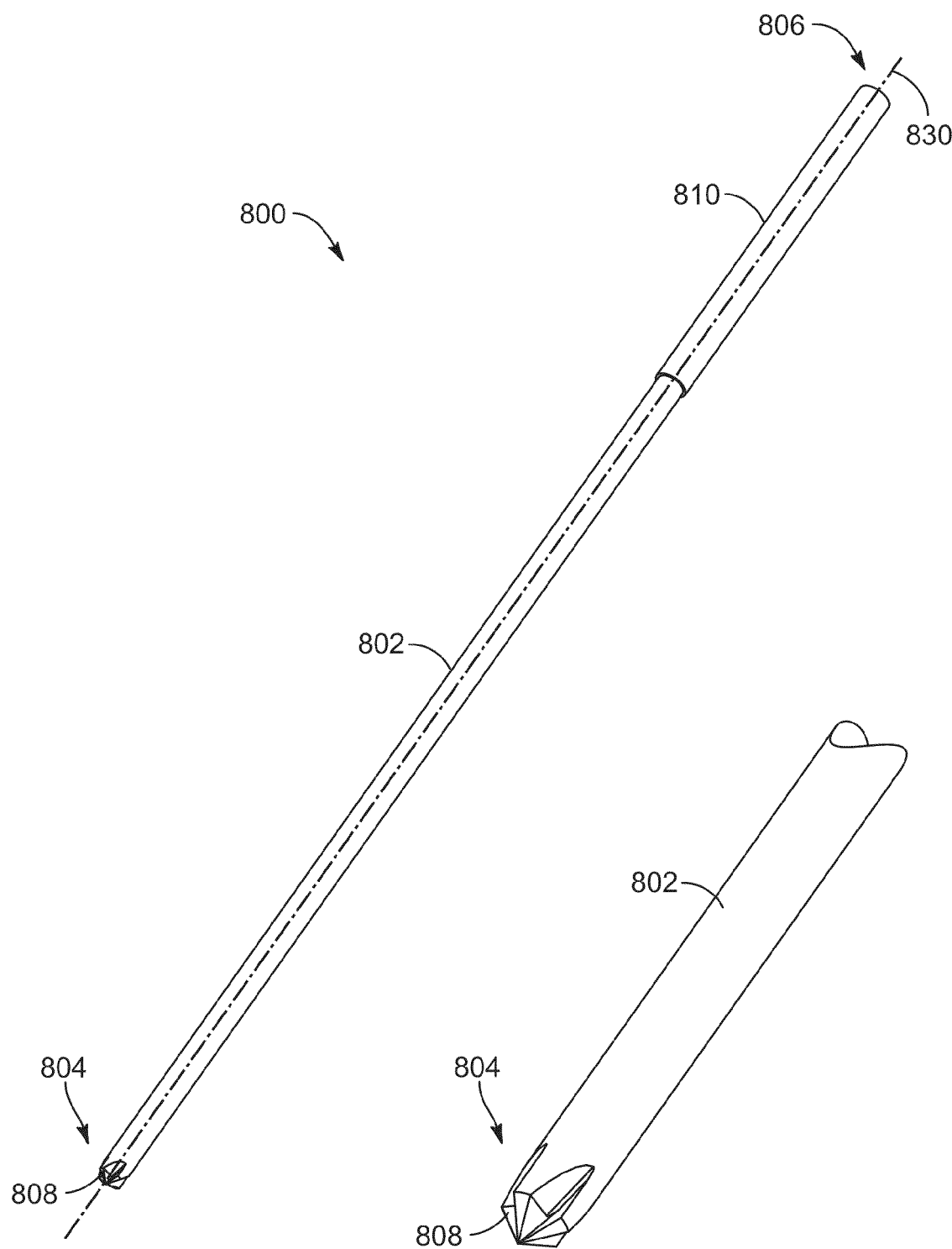
FIG. 16A is a perspective view of another alternate embodiment of a drill.
FIG. 16B is a detail view of an end of the drill of FIG. 16A.

Referring to FIG. 16, a third femoral drill 800 is shown. The drill 800 may comprise a shaft 802 with a leading end 804 and a trailing end 806. The shaft 802 has a center longitudinal axis 830. The leading end 804 may have a plurality of cutting flutes 808 formed in the leading end 804, similar to drill 400. The trailing end 806 may comprise a shank 810 which may have various configurations, as described for shank 410 of drill 400. At least the leading end 804 and shaft 802 of the drill 800 may be received within the hole 720 of the femoral tamp 700 with clearance so that the drill 800 may slide and rotate within the hole 720. Drill 800 may have a smaller diameter than drill 400 or drill 600. Alternatively, hole 720 may be sized to receive guide wire 300 with clearance so that the guide wire 300 may slide and rotate within the hole 720.

Figure 17:
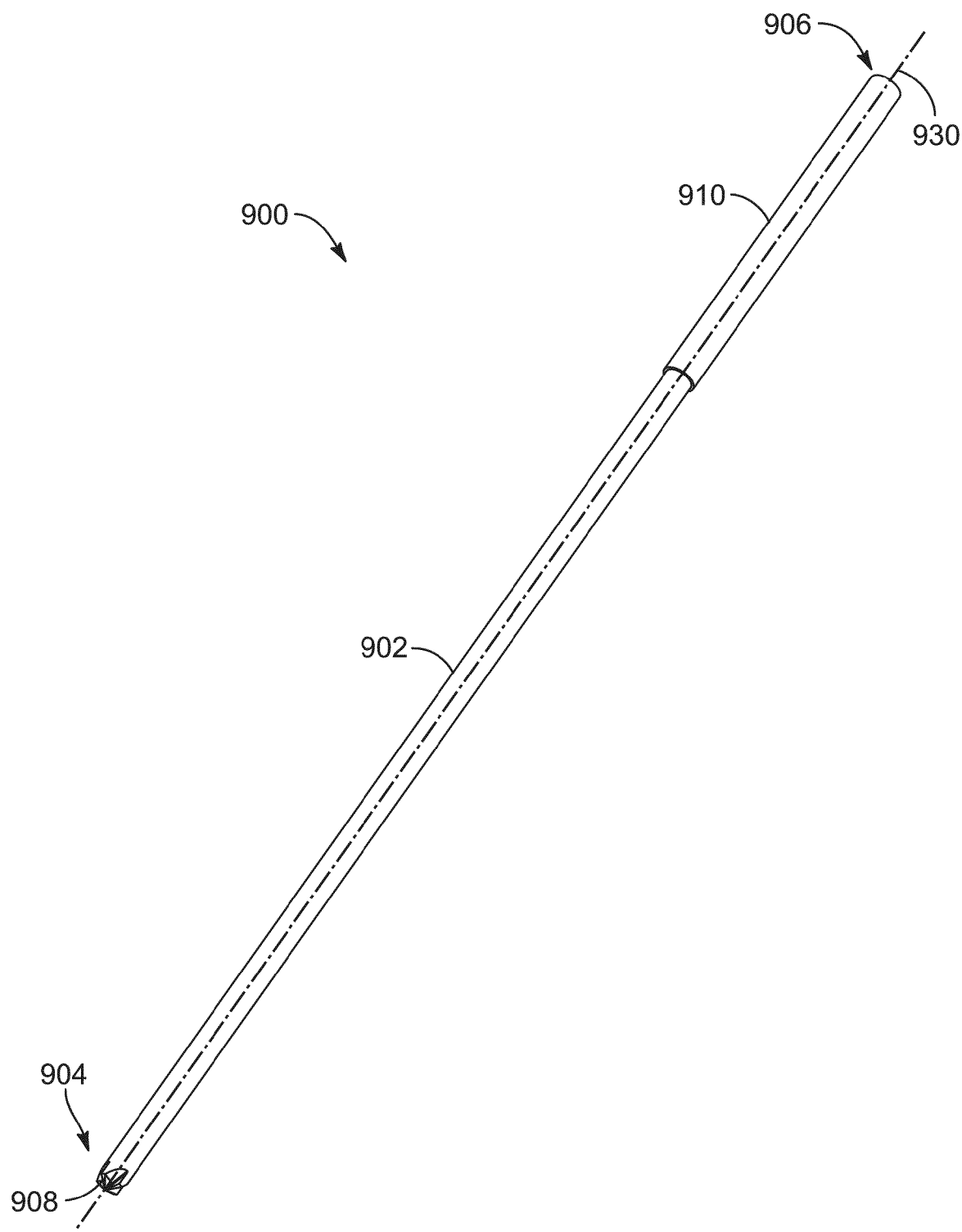
FIG. 17 is a perspective view of yet another alternate embodiment of a drill.

Referring to FIG. 17, a first tibial drill 900 is shown. The drill 900 may comprise a shaft 902 with a leading end 904 and a trailing end 906. The shaft 902 has a center longitudinal axis 930. The leading end 904 may have a plurality of cutting flutes 908 formed in the leading end 904, similar to drill 400. The trailing end 906 may comprise a shank 910 which may have various configurations, as described for shank 410 of drill 400.

Figure 18:
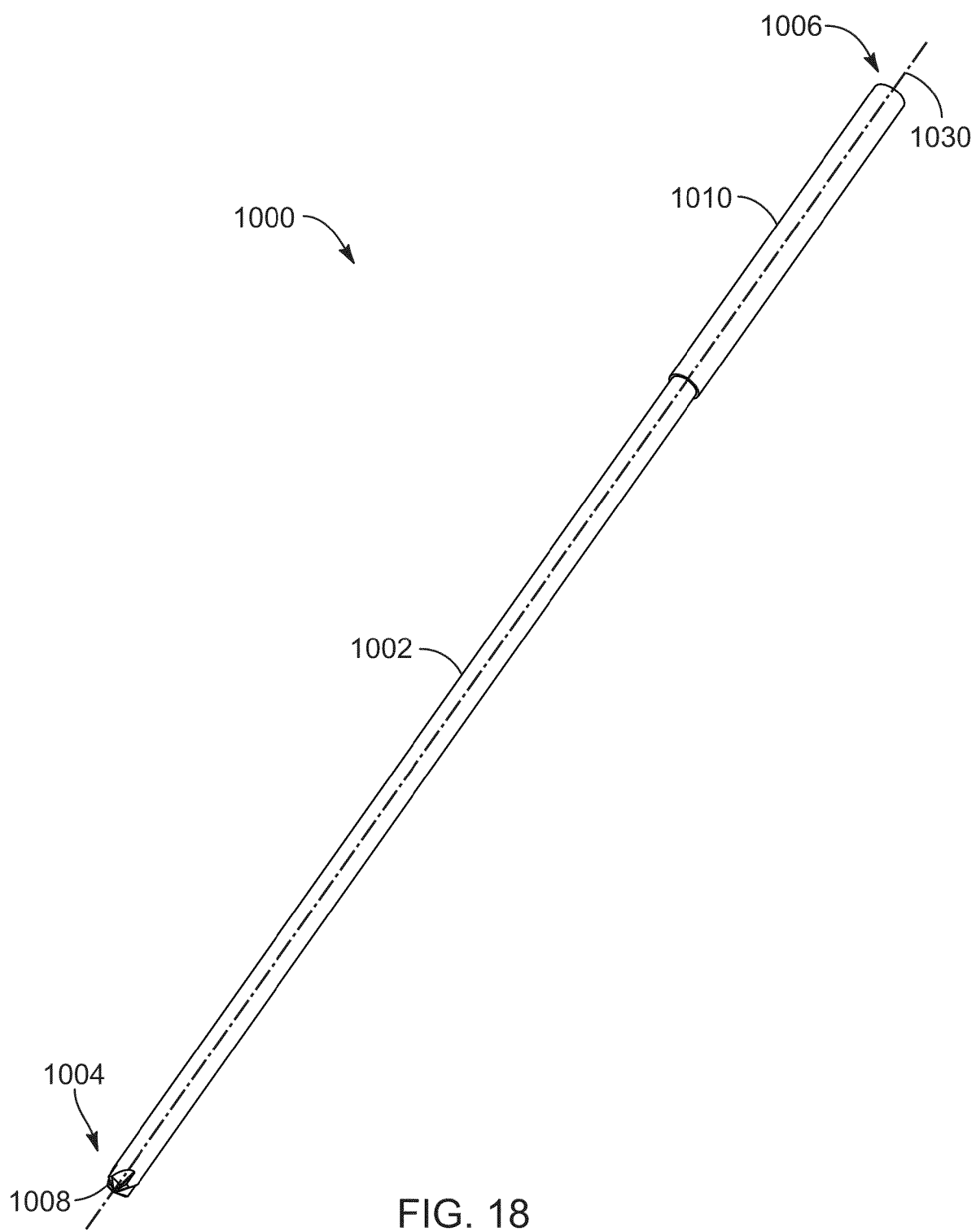
FIG. 18 is a perspective view of yet another alternate embodiment of a drill.

Referring to FIG. 18, a second tibial drill 1000 is shown. The drill 1000 may comprise a shaft 1002 with a leading end 1004 and a trailing end 1006. The shaft 1002 has a center longitudinal axis 1030. The leading end 1004 may have a plurality of cutting flutes 1008 formed in the leading end 1004, similar to drill 400. The trailing end 1006 may comprise a shank 1010 which may have various configurations, as described for shank 410 of drill 400.

A kit of drills may be provided. The kit of drills may include drills 400, 600, 800, 900, and 1000, as set forth above. In other words, the kit may include drills which are cannulated and non-cannulated, of various diameters, of various operative lengths, which may have one or more depth marks or depth stops, and which may operatively cooperate with the guide wire 300, drill guide 500, tamp 700, or tamp 1100.

Figure 19A:
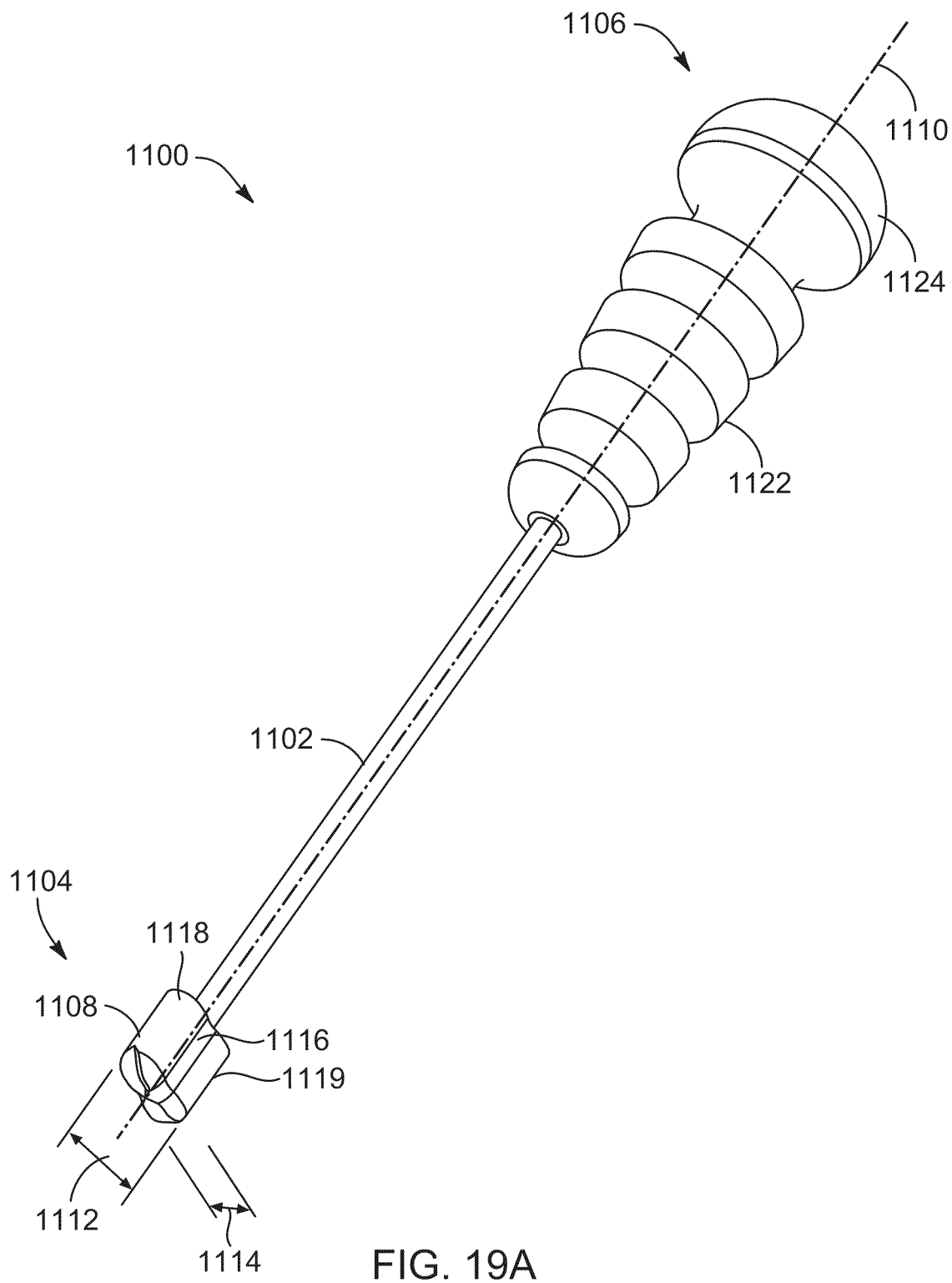
FIG. 19A is a perspective view of an alternate embodiment of a tamp.
Figure 19B:
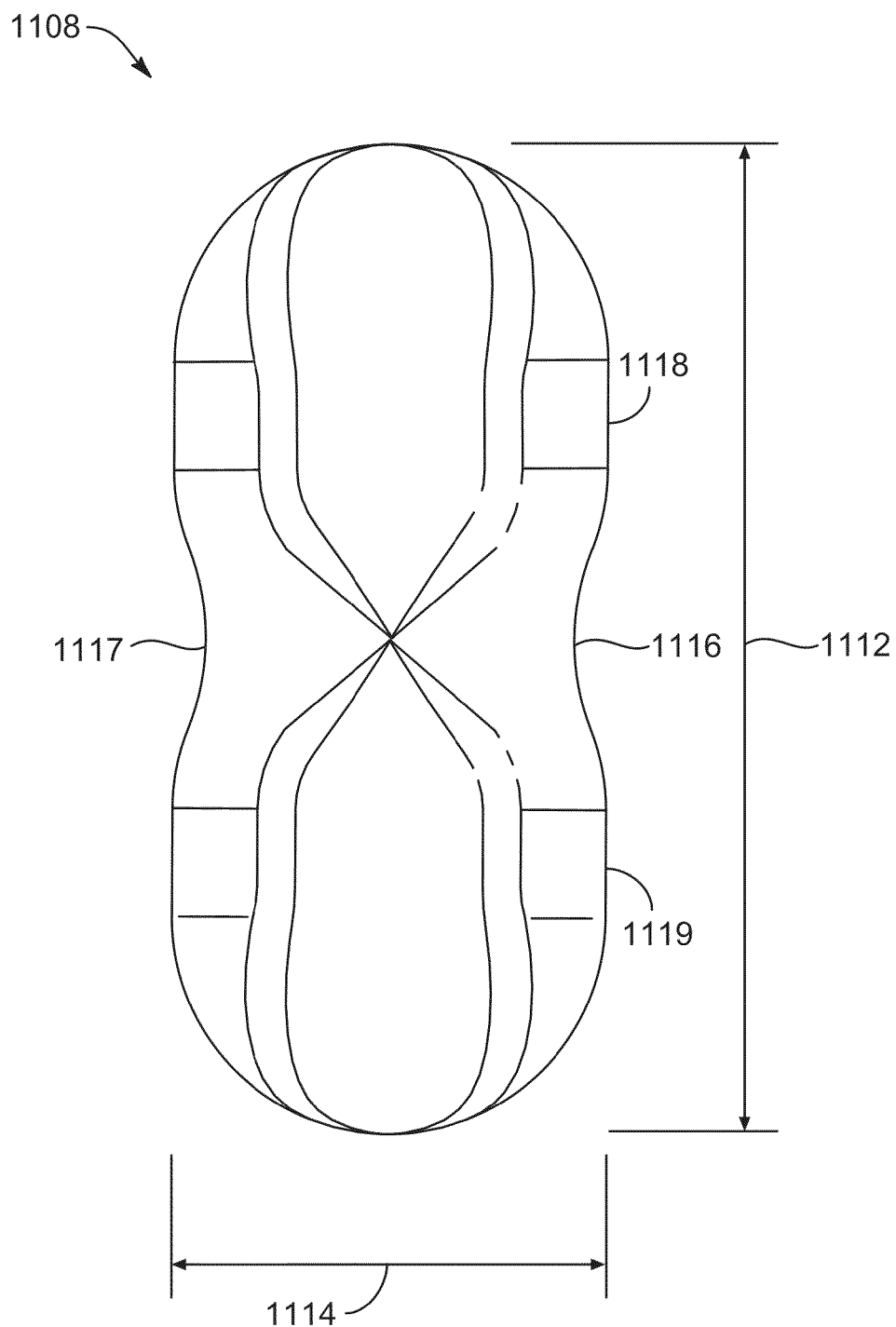
FIG. 19B is an end detail view of the tamp of FIG. 19A.

Referring to FIGS. 19A and 19B, a tibial tamp 1100 is shown. The tamp 1100 may comprise a shaft 1102 extending at least partially between a leading end 1104 and a trailing end 1106. The leading end 1104 may have a protruding boss 1108 that may extend along a longitudinal axis 1110. The boss 1108 may have a width 1112 and a height 1114 which is less than the width 1112. The width 1112 and height 1114 may be oriented generally perpendicular to the axis 1110, as shown in FIG. 19A. The boss 1108 may have a plurality of indentations 1116, 1117 which extend generally parallel to the axis 1110 along opposite sides of the boss 1108 so as to divide the width 1112 of the boss 1108 into a plurality of lobes 1118, 1119. A hole, not shown, similar to hole 720 of femoral tamp 700, may be present. The trailing end 1106 may include a handle 1122, striking platform 1124, or other configuration.

Referring to FIG. 19B, the boss 1108 is shown from the leading end 1104. In this embodiment, the profile shown in FIG. 19B is constant over at least a portion of boss 1108 in a direction generally parallel to axis 1110. Therefore, boss 1108 may be described as a cross section projected along the axis 1110 (FIG. 19A) from the leading end 1104 toward the trailing end 1106. In this embodiment, the profile shown in FIG. 19B may be described as a plurality of enlarged lobes 1118, 1119 separated by a constricted middle section established between indentations 1116, 1117. Alternatively, the profile shown in FIG. 19B may be described as being shaped like a figure eight, hourglass, peanut shell, or bicuspid epicycloid curve.

The boss 1108 may be formed in a variety of sizes and shapes, as described above for boss 708. A kit of modular bosses or complete tibial tamps may be provided.

Referring to FIGS. 20-32, methods of preparing the knee joint 1 (FIG. 1) and inserting the exemplary implant constructs 100, 200 will be described.

Figure 20:
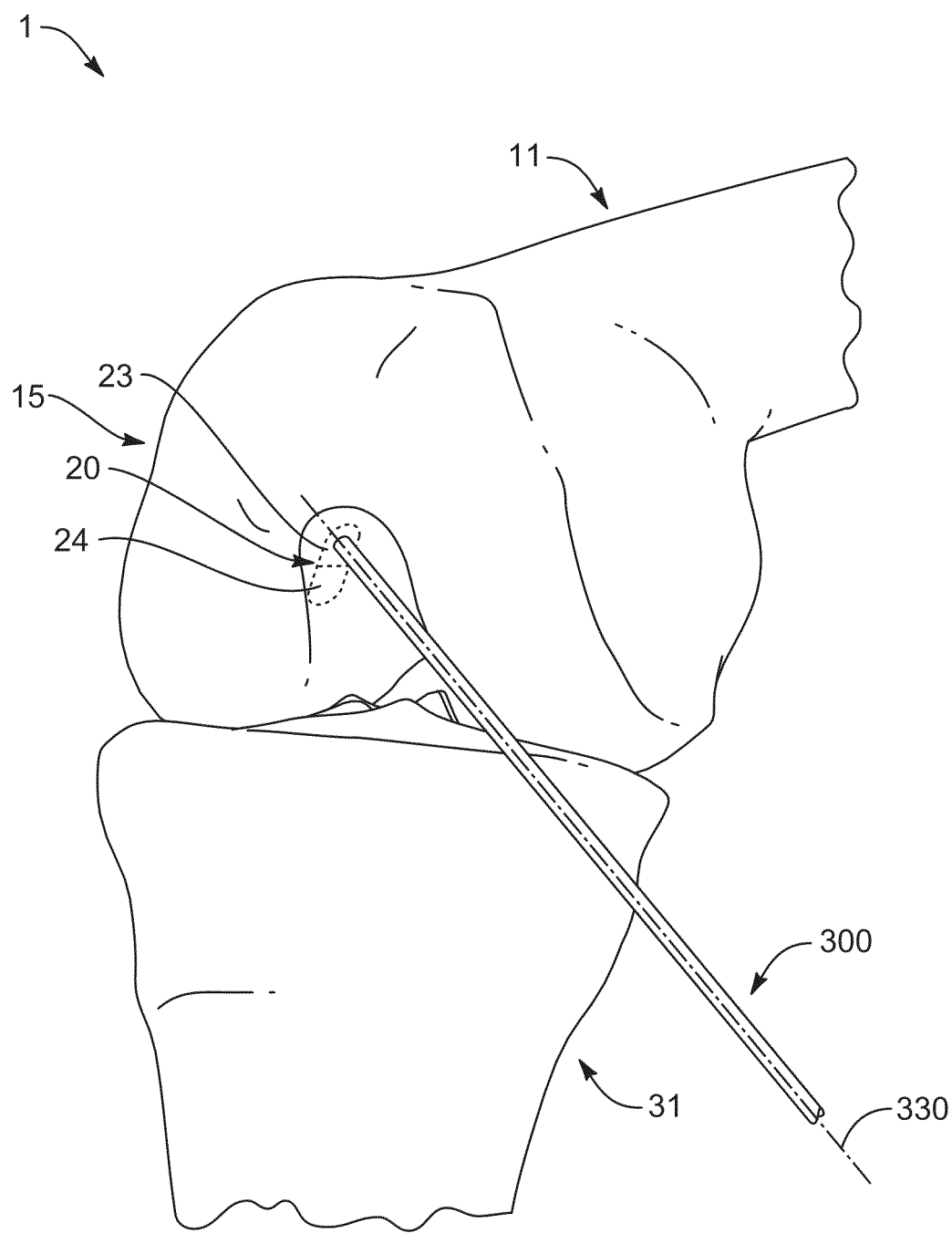
FIG. 20 is an antero-medial perspective view of the knee joint of FIG. 1 and the guide wire of FIG. 11.

Referring to FIG. 20, knee 1 is shown in flexion from an antero-medial view. The femoral ACL attachment area 20 is shown on the medial aspect of the lateral condyle 15. The femoral ACL attachment area 20 is further subdivided into the AM area 23 and PM area 24. The guide wire 300 may be inserted into the AM area 23. In the present embodiment, the guide wire 300 is shown as if inserted from an antero-medial portal to the joint space.

Figure 21:
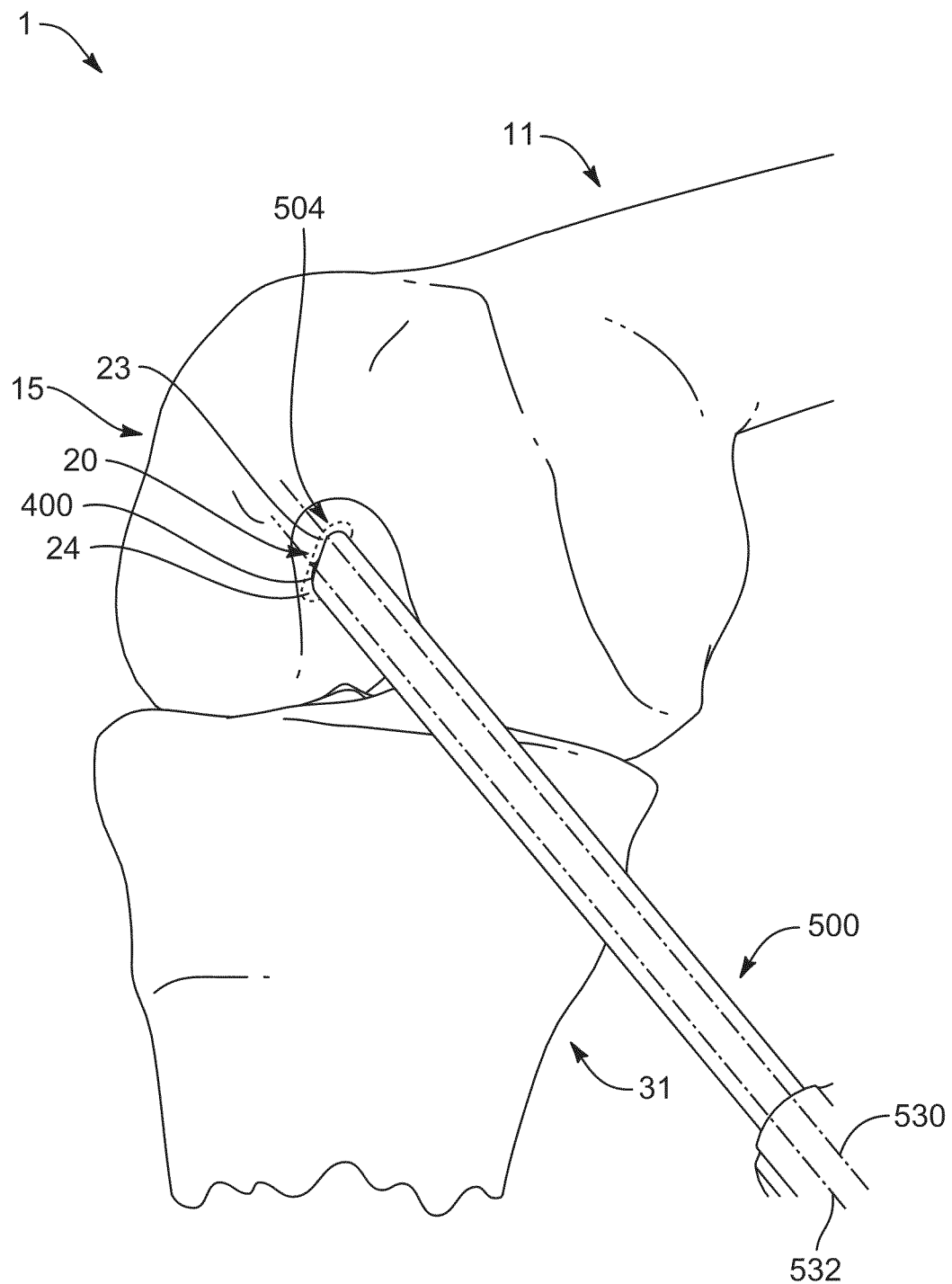
FIG. 21 is an antero-medial perspective view of the knee joint of FIG. 1, the drill of FIG. 12, and the drill guide of FIG. 13.

Referring to FIG. 21, the drill guide 500 is positioned so that guide wire 300 is in hole 508, the leading end 504 abuts the medial aspect of the lateral condyle 15, and hole 510 is positioned over the PL area 24. With the drill guide 500 so positioned, axis 530 is substantially collinear with axis 330. The drill 400 may be inserted into hole 510 and rotated so that the leading end 404 of the drill 400 extends a predetermined distance past the leading end 504 of the drill guide 500 and into the medial aspect of the lateral condyle 15. With the drill 400 so positioned, axis 430 is substantially collinear with axis 532.

Figure 22:
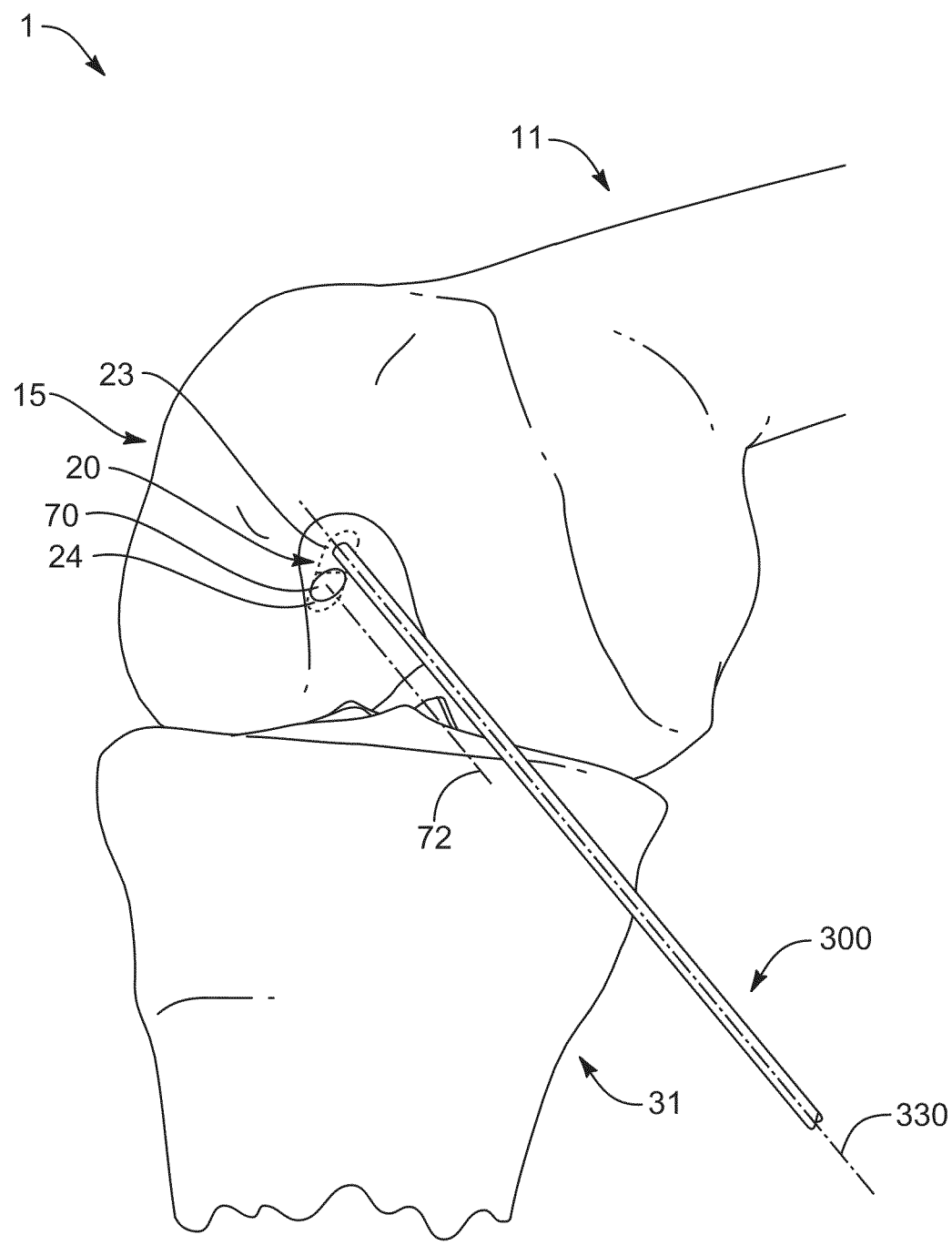
FIG. 22 is an antero-medial perspective view of the knee joint of FIG. 1 and the guide wire of FIG. 11, showing a first hole formed in the femur.

Referring to FIG. 22, the drill 400 and drill guide 500 have been removed, leaving the guide wire 300 in place. A first femoral hole 70 has been created in the PL area 24 by the drill 400. Hole 70 has a center longitudinal axis 72 which may be spaced apart from, and substantially parallel to, axis 330, similar to the relationship described above between axis 530 and axis 532.

Figure 23:
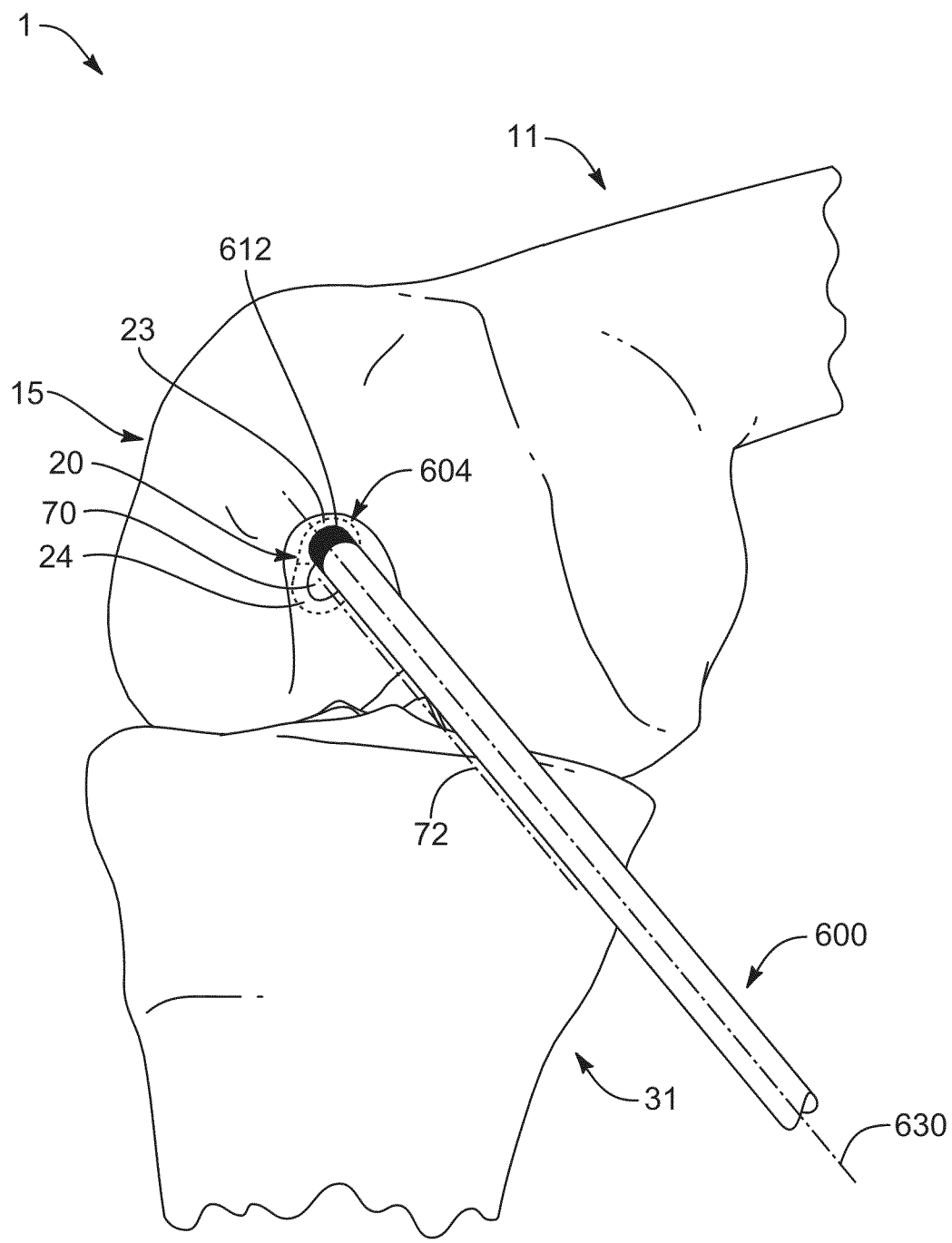
FIG. 23 is an antero-medial perspective view of the knee joint of FIG. 1 and the drill of FIG. 14.

Referring to FIG. 23, the drill 600 is positioned so that guide wire 300 is in hole 614. In this position, axis 630 may be substantially collinear with axis 330. Drill 600 may be advanced and rotated so that leading end 604 extends into the medial aspect of the lateral condyle 15. When depth mark 612 reaches the medial aspect of the lateral condyle 15, this may provide a visual indication that drill 600 has reached a predetermined depth, which may be equal to the distance that leading end 404 of drill 400 extends past leading end 504 of drill guide 500.

Figure 24:
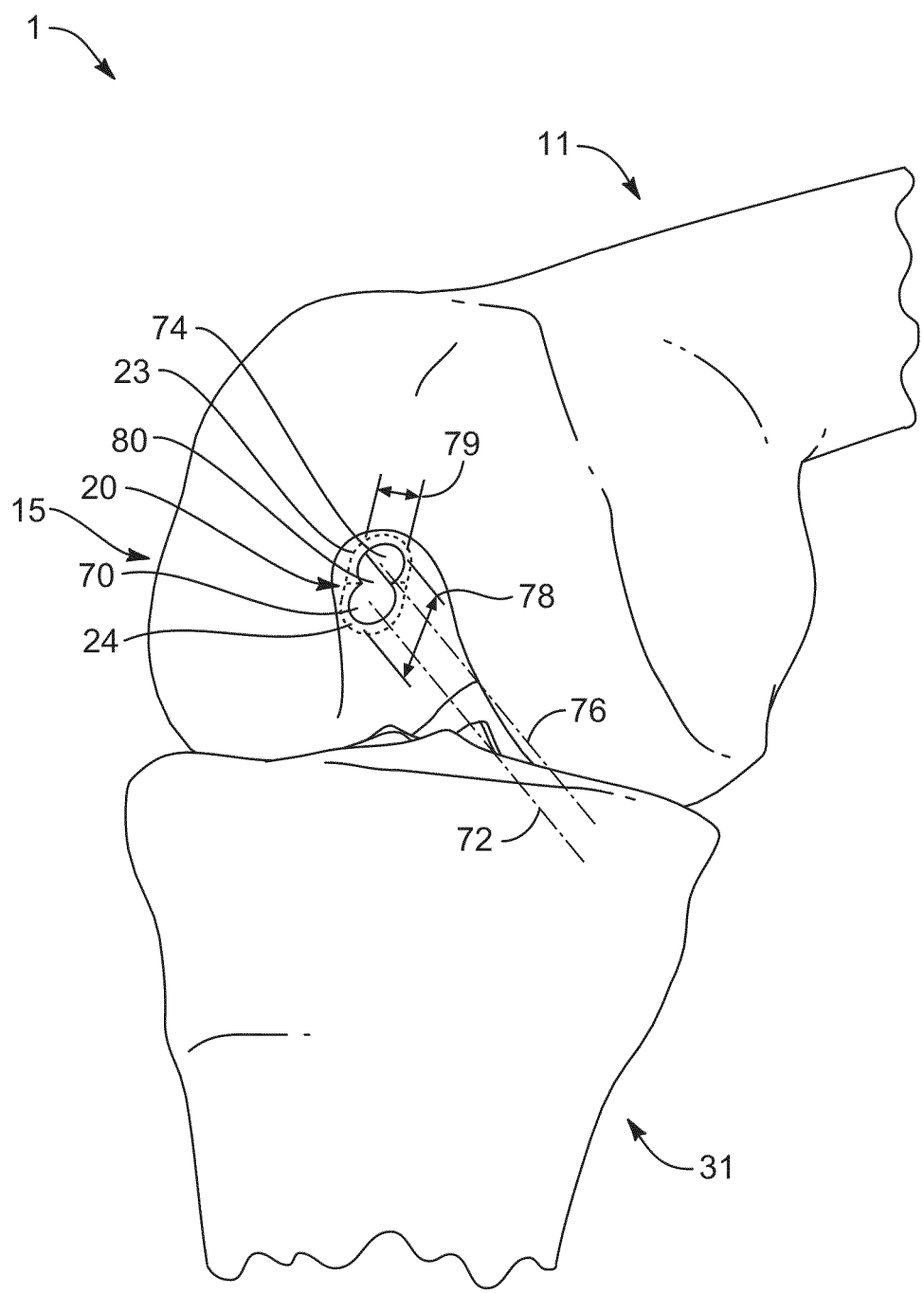
FIG. 24 is an antero-medial perspective view of the knee joint of FIG. 1, showing the first hole and a second hole partially overlapping the first hole.

Referring to FIG. 24, the drill 600 and guide wire 300 have been removed. A second femoral hole 74 has been created in the AM area 23 by the drill 600. Hole 74 has a center longitudinal axis 76 which may be spaced apart from, and substantially parallel to, axis 72, similar to the relationship described above between axis 530 and axis 532. Holes 70 and 74 form a composite tunnel 80 which has a cross section that can be described as a plurality of enlarged lobes separated by a constricted middle section, a figure eight shape, an hourglass shape, a peanut shell shape, or a bicuspid epicycloid shape. Tunnel 80 has a width 78 which is equal to the sum of the radius of hole 70, the radius of hole 74, and the distance between axes 72 and 76. Tunnel 80 has a height 79 which is equal to the greater of the radii of holes 70 and 74.

Figure 25:
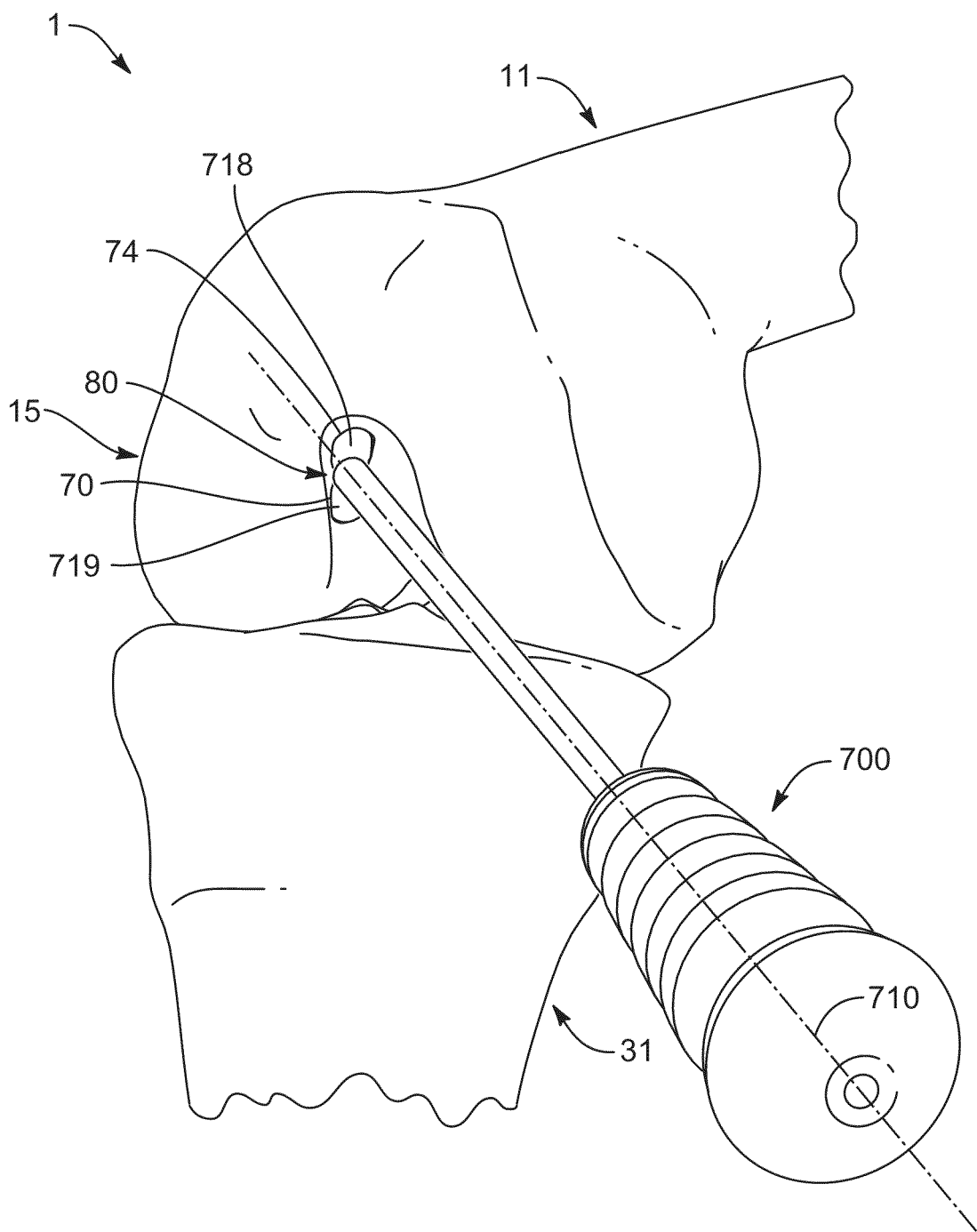
FIG. 25 is an antero-medial perspective view of the knee joint of FIG. 1 and the tamp of FIGS. 15A-15B.

Referring to FIG. 25, the femoral tamp 700 may be positioned so that leading end 704 abuts the medial aspect of the lateral condyle 15, lobe 718 is aligned with hole 74, and lobe 719 is aligned with hole 70. In this position, axis 710 may be situated between, and substantially parallel to, axes 72 and 76. The boss 708 may be pushed into tunnel 80, or driven in with a mallet (not shown) or other manual or powered tool. The width 712 of the boss 708 may be greater than the width 78 of the tunnel 80 and the height 714 of the boss 708 may be similar to the height 79 of the tunnel 80. Thus, as boss 708 is advanced within tunnel 80, the tunnel 80 may be selectively expanded along its width 78 more than its height 79. Alternatively, the width 712 and height 714 of the boss 708 may be chosen to selectively expand the tunnel 80 along its height 79 more than its width 78, or along both height 79 and width 78 equally.

While the femoral tamp 700 is fully inserted in the tunnel 80, the drill 800 may be inserted into hole 720 and rotated so that the leading end 804 of the drill 800 extends past the leading end 704 of the tamp 700 and into the lateral condyle 15. With the drill 800 so positioned, axis 830 may be substantially collinear with axis 710. Drill 800 may be advanced within tamp 700 until the leading end 804 penetrates the lateral cortex of the lateral condyle 15.

Alternatively, guide wire 300 may be inserted into a correspondingly sized hole 720 and advanced through the lateral condyle 15. A cannulated drill may be passed over guide wire 300 after removal of femoral tamp 700.

Figure 26:
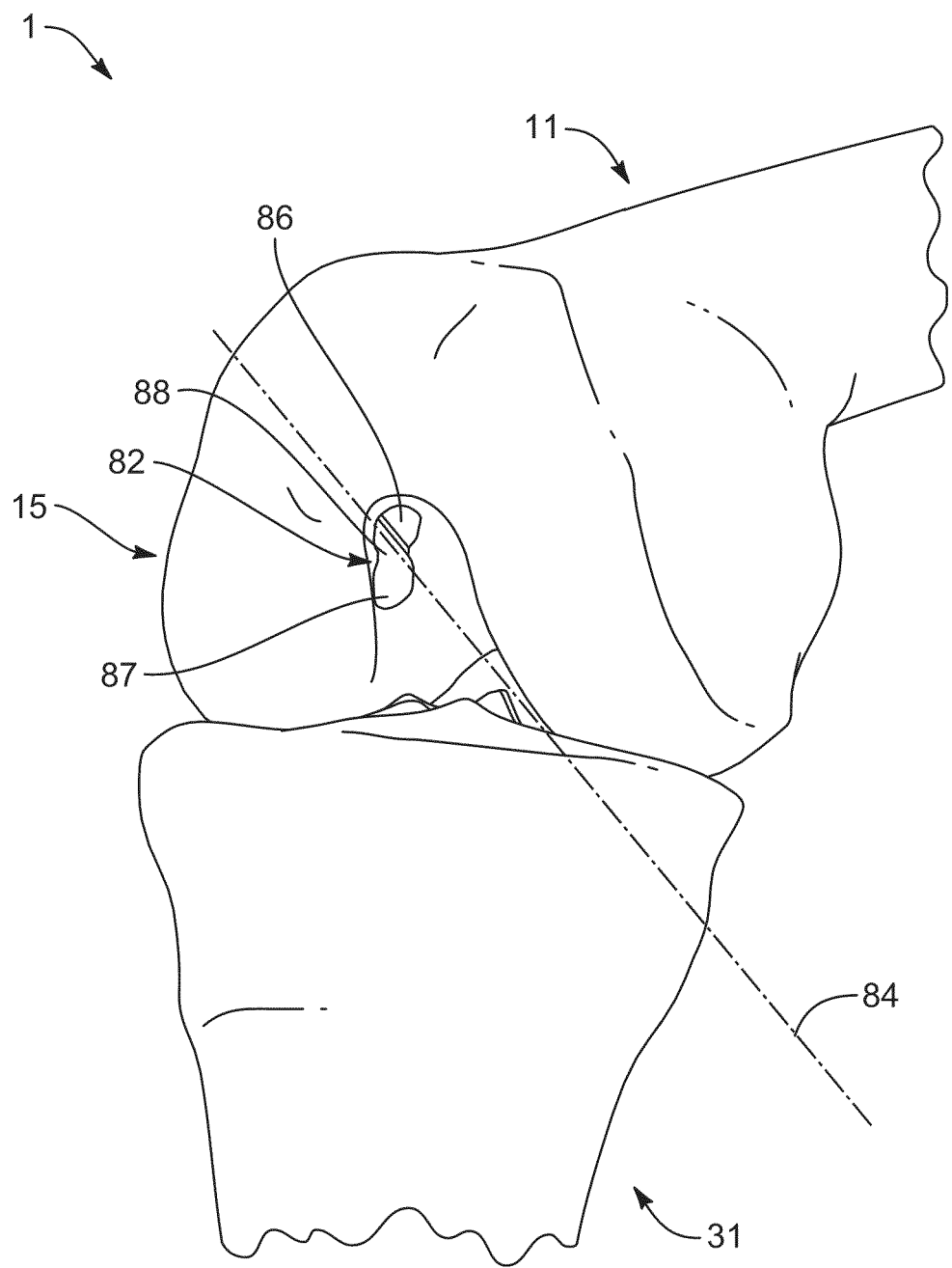
FIG. 26 is an antero-medial perspective view of the knee joint of FIG. 1, showing a fully formed femoral tunnel.

Referring to FIG. 26, femoral tamp 700 has been removed. A shaped tunnel 82 has been formed in the femoral ACL attachment area 20 by the femoral tamp 700. Tunnel 82 has a center longitudinal axis 84 which is substantially collinear with axis 710. Tunnel 82 has taken on a cross sectional shape that substantially corresponds to that of boss 708. Therefore, the cross section of tunnel 82 may be described as a plurality of enlarged lobes 86, 87 separated by a constricted middle section 88, a figure eight shape, an hourglass shape, a peanut shell shape, or a bicuspid epicycloid shape.

Figure 30A:
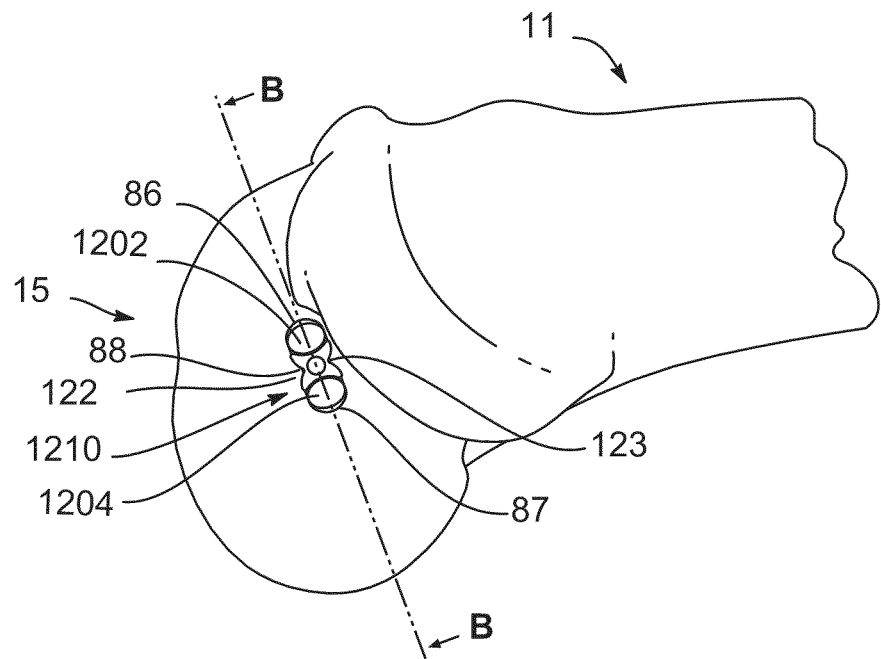
FIG. 30A is a perspective view of the femur of FIG. 27 and the graft construct of FIG. 28 along a longitudinal axis of the first fixation device of FIGS. 8A-8B.
Figure 30B:
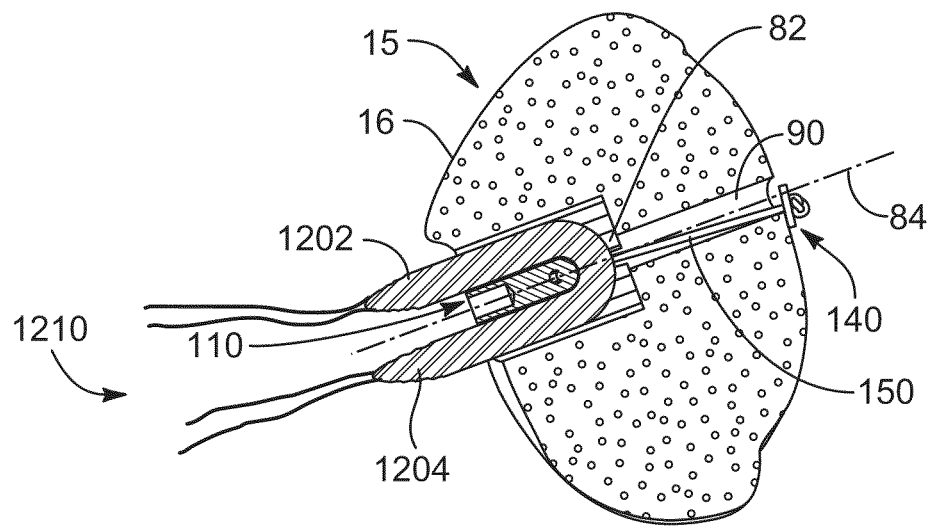
FIG. 30B is a cross sectional view of the femur of FIG. 27 and the graft construct of FIG. 28.

A smaller diameter tunnel 90, best seen in FIG. 30B, has been formed in the lateral condyle 15 by drill 800. Tunnel 90 is substantially centered on axis 84 and extends between tunnel 82 and the lateral aspect of the lateral condyle 15.

Figure 27:
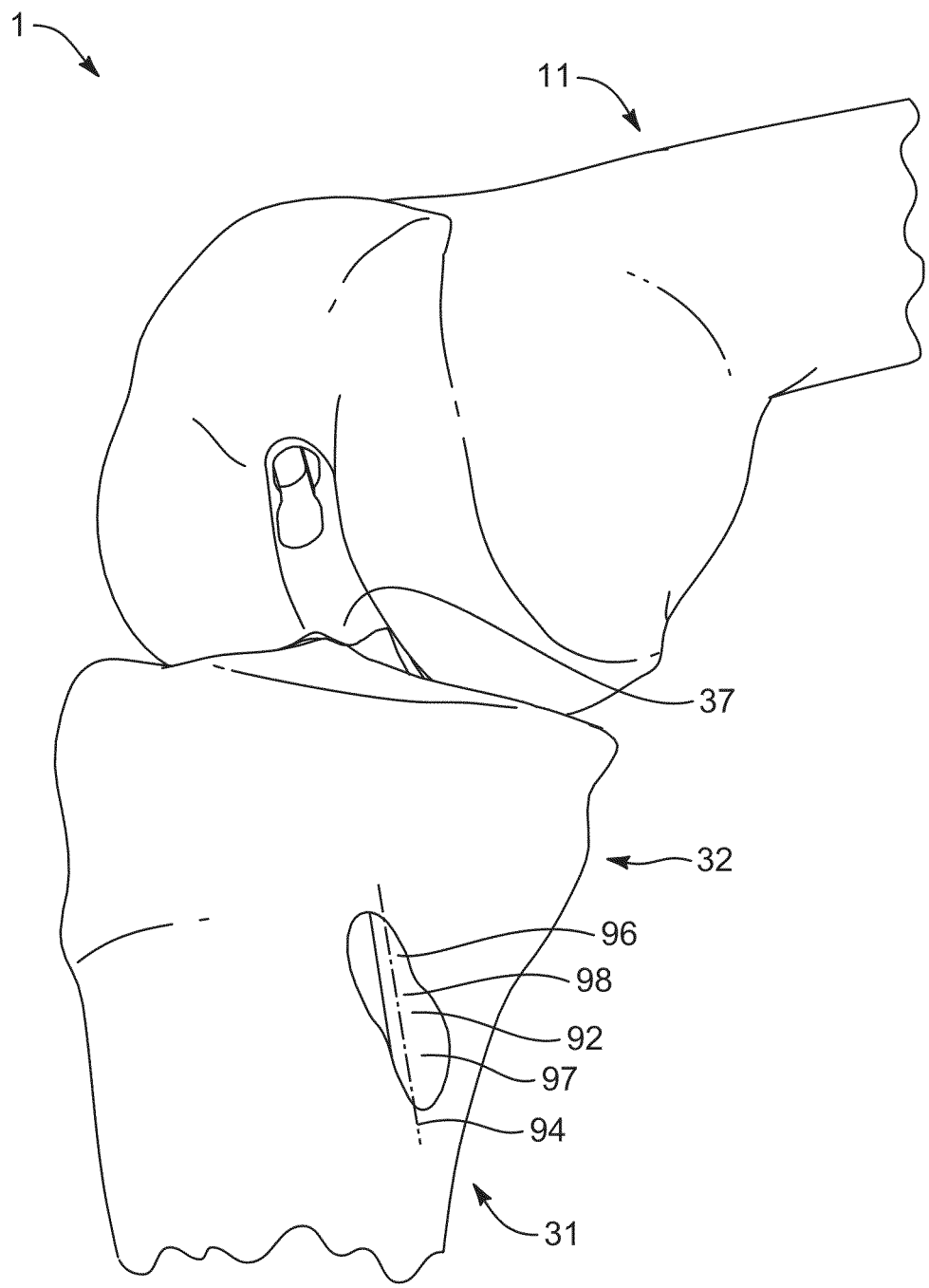
FIG. 27 is an antero-medial perspective view of the knee joint of FIG. 1, showing the femoral tunnel and a fully formed tibial tunnel.

Referring to FIG. 27, a shaped tunnel 92 has been formed in the tibia 31 according to a method similar to that set forth above with regard to the femoral tunnel 82. In the present embodiment, tunnel 92 is shown extending from the anteromedial aspect of the proximal end 32 of the tibia 31 to the tibial ACL attachment area 40 on the intercondylar eminence 37. Tunnel 92 has a center longitudinal axis 94. Tunnel 92 may be formed using guide wire 300, drill guide 500, drill 900, drill 1000, and tamp 1100. The method of preparing tunnel 92 may differ from the method of preparing tunnel 82 set forth above. Drills 900, 1000 may be of different diameters than corresponding drills 400, 600. Drills 900, 1000 may extend farther past the leading end 504 of the drill guide 500 than do corresponding drills 400, 600, such that the leading ends 904, 1004 of drills 900, 1000 may extend through the tibial ACL attachment area 40. The leading end 1104 of tamp 1100 may be advanced so that it extends to or through the tibial ACL attachment area 40. There may be no smaller diameter tunnel in the tibial 31 analogous to tunnel 90 in the femur 11.

Tunnel 92 has a cross sectional shape that substantially corresponds to that of boss 1108 of tibial tamp 1100. Therefore, the cross section of tunnel 92 may be described as a plurality of enlarged lobes 96, 97 separated by a constricted middle section 98, a figure eight shape, an hourglass shape, a peanut shell shape, or a bicuspid epicycloid shape.

Figure 36:
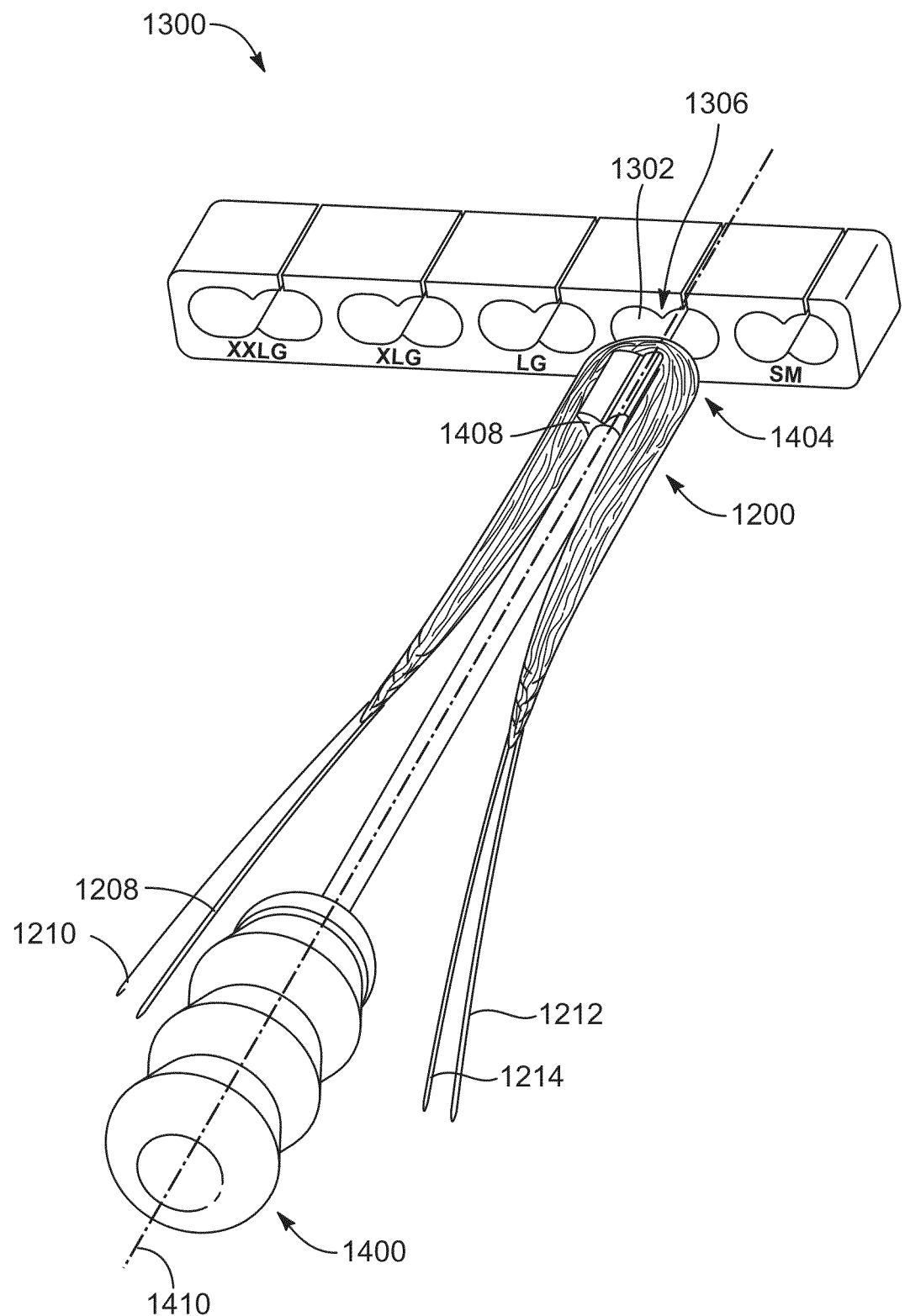
FIG. 36 is a perspective view of the graft sizing block of FIG. 34, the trial instrument of FIG. 35, and the soft tissue graft of FIG. 28.

Referring to FIG. 36, the graft sizing block 1300 and trial instrument 1400 are shown combined with a soft tissue graft 1200. Soft tissue graft 1200 may be an autograft or allograft, and may comprise a quadriceps tendon, one or more hamstring tendons, Achilles tendon, tibialis anterior tendon, peroneal tendon, or other tendinous or ligamentous graft material. Graft 1200 may also be a xenograft or artificial graft. Soft tissue graft 1200 may be provided with sutures 1208, 1210, 1212, 1214 which may facilitate manipulation of soft tissue graft 1200 before and during implantation.

Soft tissue graft 1200 is shown draped across the leading end 1404 of the trial instrument 1400 and extending along the boss 1408 generally parallel to axis 1410 so that the soft tissue graft 1200 lies against crescent shaped portions 1419, 1418. The indentations 1416, 1417 of trial instrument 1400 are aligned with the constricted middle section 1306 of the aperture 1302 in the graft sizing block 1300. As the trial instrument 1400 and soft tissue graft 1200 are advanced through the aperture 1302, the relative fit of the instrument 1400 and graft 1200 in the aperture 1302 may be assessed. A snug sliding fit may indicate a proper combination of a particular size boss 1408 with a particular size graft 1200. Once a proper combination of boss 1408, aperture 1302, and graft 1200 is determined, the trial instrument 1400 and graft 1200 may be removed from the graft sizing block 1300.

Figure 28:
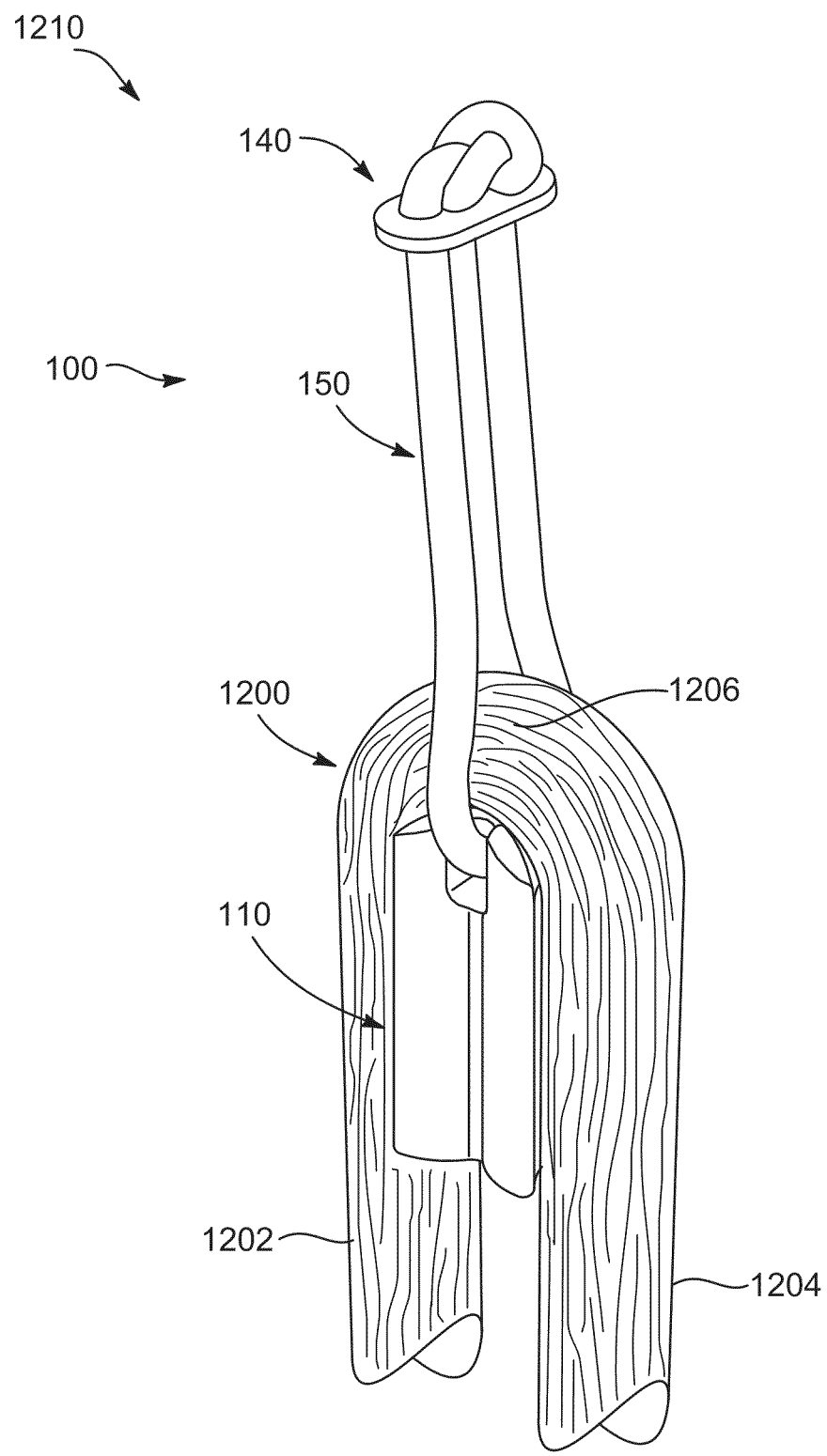
FIG. 28 is a perspective view of a graft construct according to the present invention, showing the implant construct of FIG. 7 and a soft tissue graft.

Referring to FIG. 28, the femoral implant construct 100 is shown combined with the soft tissue graft 1200 to form a graft construct 1210. In the present embodiment, the soft tissue graft 1200 may be a single hamstring tendon which rests in the groove 120 of plug 111. Soft tissue graft 1200 may have a first bundle 1202, a second bundle 1204, and a middle portion 1206.

Figure 29:
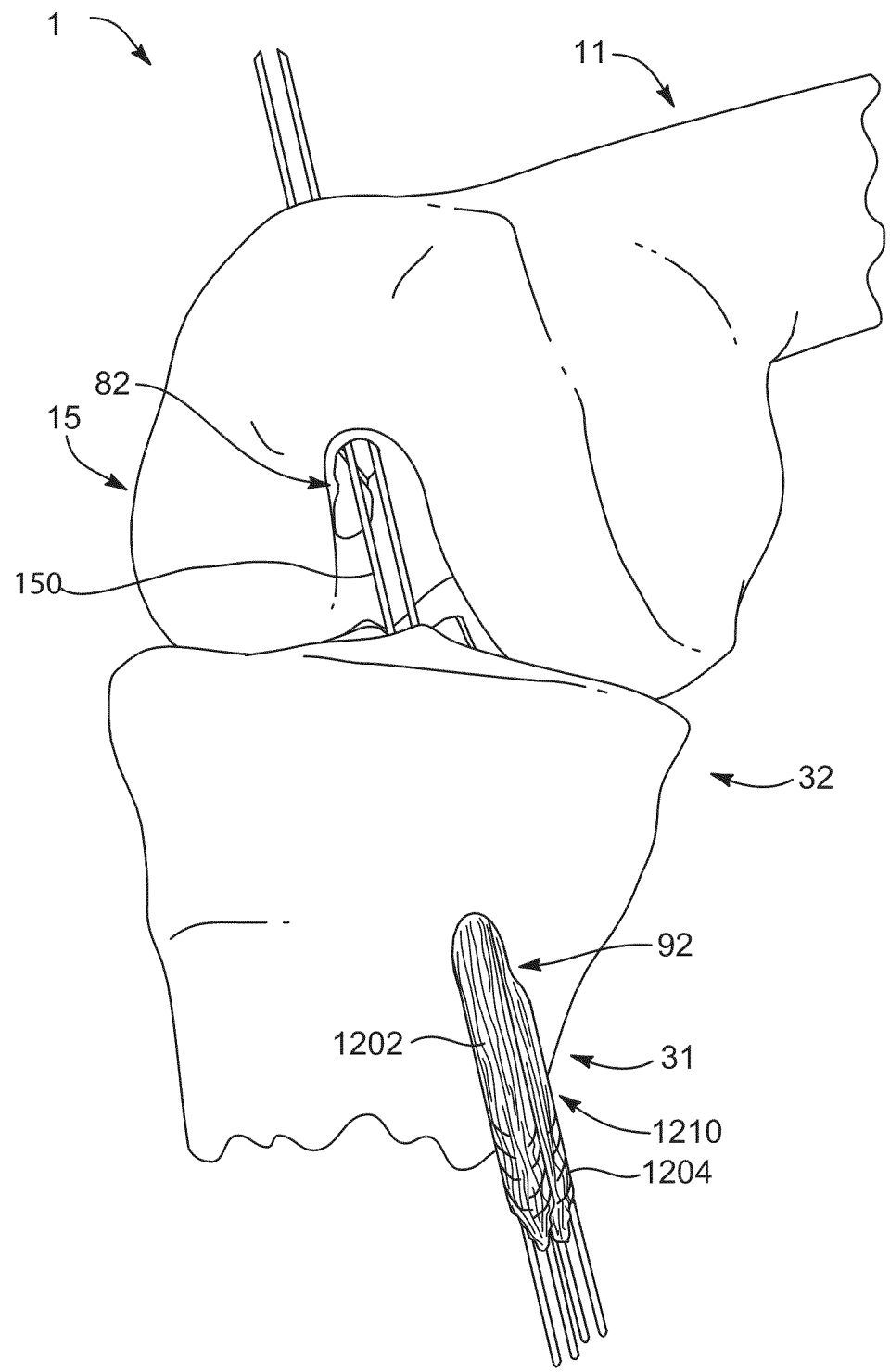
FIG. 29 is an antero-medial perspective view of the knee joint of FIG. 27 and the graft construct of FIG. 28.

Referring to FIG. 29, the graft construct 1210 is shown passing through the tibial tunnel 92 with the connector 150 leading and the first and second bundles 1202, 1204 of the soft tissue graft 1200 trailing. The first fixation device 110 and soft tissue graft 1200 are pulled into tunnel 82 behind connector 150. An instrument (not shown) may be used to orient first fixation device 110 with regard to tibial tunnel 92 or femoral tunnel 82 or to urge first fixation device 110 into femoral tunnel 82. By way of non-limiting example, an instrument shaft may be inserted into hole 130 to orient and advance the first fixation device 110. Second fixation device 140 is subsequently positioned to engage the lateral aspect of the lateral condyle 15 and secured to connector 150.

Referring to FIGS. 30A and 30B, the graft construct 1210 is shown in the final implanted position in the femur 11.

FIG. 30A is a view of femoral tunnel 82 along axis 84. A cross section line B-B is shown across tunnel 82 and the distal end 13 of the femur 11. First fixation device 110 is shown from the trailing end 118. Axis 114 may be substantially parallel with axis 84; axes 114 and 84 may further be substantially collinear. Indentations 122, 123 congruently engage constricted middle section 88, while crescent portions 126, 127 open toward lobes 86, 87, thus defining separate chambers in which the first and second bundles 1202, 1204 of the soft tissue graft 1200 rest.

FIG. 30B is a cross sectional view of femur 11 taken along line B-B so that the lateral condyle 15 is shown. Second fixation device 140 is shown engaging the lateral aspect of the lateral condyle 15. First fixation device 110 and soft tissue graft 1200 are shown resting in tunnel 82 proximate the articular surface 16. Connector 150 extends from first fixation device 110 through tunnel 90 to second fixation device 140.

Figure 31:
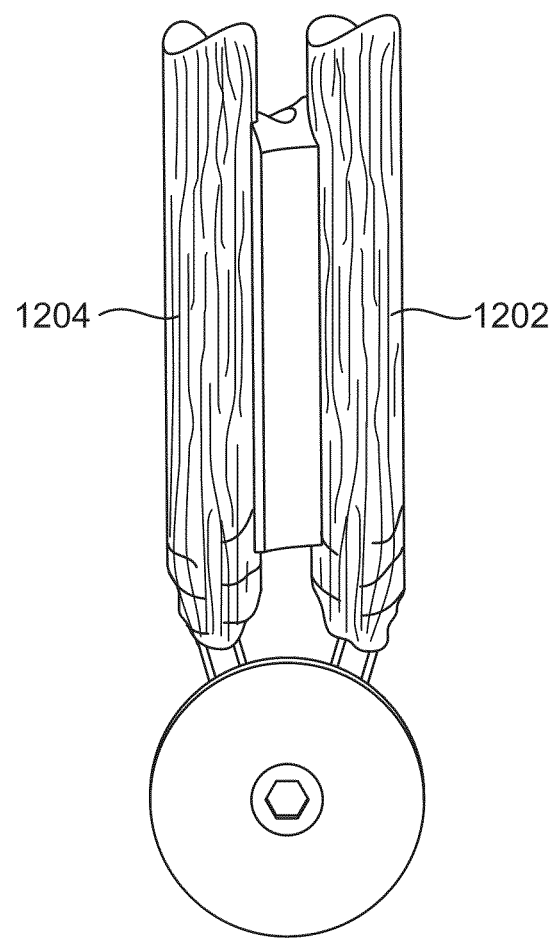
FIG. 31 is a perspective view of the implant construct of FIG. 9 and the soft tissue graft of FIG. 28.

Referring to FIG. 31, the tibial implant construct 200 is shown in combination with the soft tissue graft 1200. In the present embodiment, the bundles 1202, 1204 of soft tissue graft 1200 rest in the longitudinal portions of groove 220 of plug 211. According to the present embodiment, the first fixation device 210 and connector 250 of tibial implant construct 200 may be introduced between the bundles 1202, 1204 of soft tissue graft 1200 after the graft construct 1210 has reached its final implanted position in the femur 11. Tibial implant construct 200 may be urged into tibial tunnel 92 so that the leading end 216 of the plug 211 comes to rest proximate the articular surface 36 of the tibia and axes 214, 94 are at least substantially parallel, and preferably substantially collinear. An instrument (not shown) may be used to orient first fixation device 210 with regard to tibial tunnel 92 and to urge first fixation device 210 into tibial tunnel 92. By way of non-limiting example, an instrument shaft may be inserted into hole 230 to orient and advance the first fixation device 210.

Figure 32:
FIG. 32 is an antero-medial perspective view of the knee joint of FIG. 27, the graft construct of FIG. 28, and the implant construct of FIG. 9.
Figure 33:
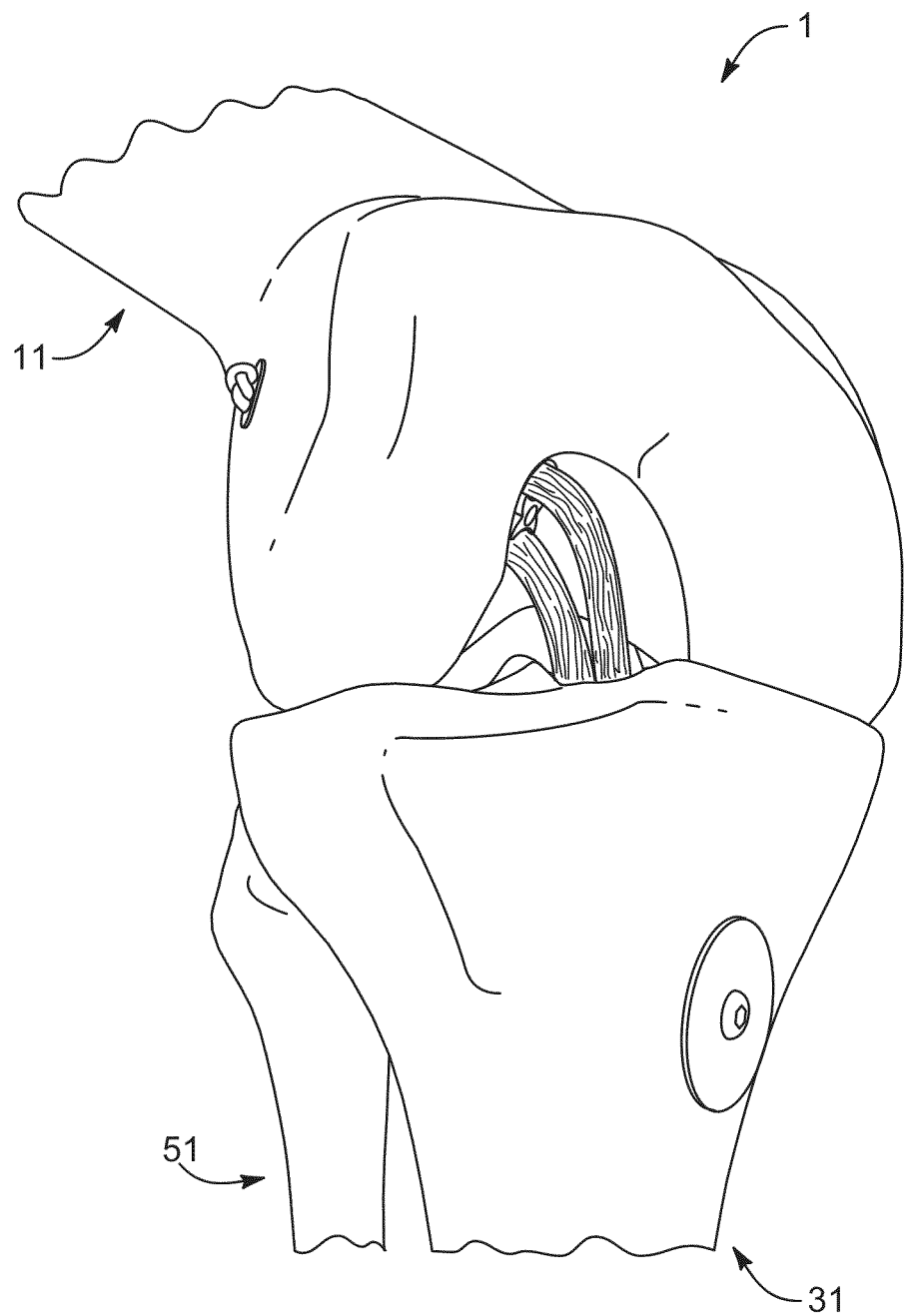
FIG. 33 is an antero-lateral perspective view of the knee joint of FIG. 27, the graft construct of FIG. 28, and the implant construct of FIG. 9.

Referring to FIGS. 32-33, the tibial implant construct 200 and soft tissue graft 1200 are shown in the final implanted position in the tibia 31. Connector 250 extends from first fixation device 210 to the antero-medial aspect of the proximal end 32 of the tibia 31. Second fixation device 240 engages connector 250 and secures the complete tibial implant construct 200 to the tibia 31. In the present embodiment, screw 242 passes through loop 251 and advances into the proximal end 32 of the tibia 31 so that washer 244 presses loop 251 against the proximal end 32 of the tibia 31.

Alternative embodiments of the method set forth above are contemplated within the scope of the present invention.

In one alternative, the femoral tunnel 82 may be formed by inserting the guide wire 300 in the PL area 24, drilling the first femoral hole 70 in the AM area 23, drilling the second femoral hole 74 in the PL area 24, and shaping the composite tunnel 80 with the femoral tamp 700. A similar alternative is contemplated for tibial tunnel 92.

In another alternative, the femoral tunnel 82 may be formed by inserting the guide wire 300 in the AM area 23 or the PL area 24, drilling the second femoral hole 74 directly over the guide wire 300 with drill 600, removing the guide wire 300, inserting a boss of an alternate embodiment drill guide into the second femoral hole 74, drilling the first femoral hole 70 beside hole 74 through hole 510 of the alternate drill guide with drill 400, and shaping the composite tunnel 80 with the femoral tamp 700. A similar alternative is contemplated for tibial tunnel 92.

In yet another alternative, the tibial tunnel 92 may be prepared before the femoral tunnel 82 is prepared. In this alternative, the femoral tunnel 82 may be prepared through the tibial tunnel rather than through an antero-medial portal as described previously.

One way to view the teachings set forth above is to characterize certain structures as a body means for separating a graft into a plurality of bundles and for urging the bundles against a side wall of a first bone tunnel at a first end of the first tunnel. In the various embodiments set forth above, the first fixation devices 110, 210, as shown in FIGS. 7-10 and 28-33 and as described in the accompanying written description, can be characterized as body means.

Certain aspects of the teachings set forth above can be characterized as fixation means for securing a first end of a graft to a first bone. In the various embodiments set forth above, the second fixation devices 140, 240, as shown in FIGS. 7, 9, and 28-33, can be characterized as fixation means.

Certain aspects of the teachings set forth above can be characterized as connection means for securing the body means to the fixation means. In the various embodiments set forth above, the connectors 150, 250, as shown in FIGS. 7, 9, and 28-33, can be characterized as connection means.

The present invention may be embodied in other specific forms without departing from its spirit or essential characteristics. It is appreciated that various features of the above-described examples can be mixed and matched to form a variety of other alternatives. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An implant for anterior cruciate ligament reconstruction, comprising:
   a body extending along a longitudinal axis from a leading end to a trailing end, wherein a leading surface of the leading end comprises a cutout;
   an aperture extending at least partially through the body transverse to the longitudinal axis, wherein the aperture is in connection with the cutout;
   a first groove and a second groove extending generally parallel to the axis along a first pair of opposite sides of the body; and
   a pair of concave indentations forming concave surfaces extending generally parallel to the axis along a second pair of opposite sides of the body, wherein the second pair of opposite sides is interposed with the first pair of opposite sides, and wherein a view of the body from the trailing end comprises a pair of open crescent-like portions in back-to-back relationship forming the pair of concave indentations having two convex portions on either side of the pair of concave indentations, wherein the first groove and the second groove comprise concave surfaces, and wherein the areas of the concave surfaces of the first and second grooves are greater than the areas of the concave surfaces of the pair of concave indentations.

2. The implant of claim 1, wherein the body comprises a porous material.

3. The implant of claim 1, wherein the body comprises a therapeutic agent.

4. The implant of claim 1, further comprising an aperture through the body.

5. The implant of claim 1, wherein, the body is adapted to be inserted into a hole extending along the axis from a first end to a second end and having a figure-eight-shaped cross section comprising a pair of enlarged lobes separated by a constricted middle section, and wherein, when the body is inserted into the hole, the pair of indentations congruently engage the constricted middle section.

6. The implant of claim 5, wherein a plurality of chambers are formed between the grooved first pair of opposite sides and the enlarged lobes.

7. The implant of claim 6, wherein, when the hole is formed in a bone so as to substantially occupy a natural attachment area of a natural anterior cruciate ligament to the bone, each chamber corresponds to a natural attachment area of a functional bundle of the anterior cruciate ligament to the bone.

8. An implant for anterior cruciate ligament reconstruction, comprising:
   a body comprising a cross section projected along a longitudinal axis from a leading end to a trailing end, wherein a leading surface of the leading end comprises a cutout in connection with an aperture extending at least partially through the body transverse to the longitudinal axis; wherein the body cross section comprises a pair of open crescent-like portions formed in back-to-back relationship forming a pair of concave indentations having concave surfaces, wherein the pair of concave indentations have two convex portions on either side of the pair of concave indentations, the body further comprising a pair of grooves interposed and parallel with the pair of indentations, the pair of grooves having concave surfaces, wherein the areas of the concave surfaces of the pair of grooves are greater than the areas of the concave surfaces of the pair of concave indentations;

wherein, the leading end of the body is adapted to be inserted into a hole comprising a cross section projected along the axis from a first end to a second end, wherein the hole cross section comprises a figure-eight shape having two enlarged portions arranged on opposite sides of a constricted middle portion, wherein, when the leading end of the body is inserted into the hole the body congruently engages the constricted middle portion and the crescent-like portions open toward the enlarged portions.

9. The implant of claim 8, wherein the body comprises a porous material.

10. The implant of claim 9, wherein the porous material comprises porous polyetheretherketone.

11. The implant of claim 8, wherein the body comprises a therapeutic agent.

12. The implant of claim 8, further comprising an aperture through the common central portion.

13. The implant of claim 8, wherein a pair of chambers are formed between the crescent-like portions and the enlarged portions.

14. The implant of claim 13, wherein, when the hole is formed in a bone so as to substantially occupy a natural attachment area of a natural anterior cruciate ligament to the bone, each chamber corresponds to a natural attachment area of a bundle of the anterior cruciate ligament to the bone.

* * * * *